United States Patent [19]

Kuhajda et al.

[11] Patent Number: 5,665,874
[45] Date of Patent: Sep. 9, 1997

[54] CANCER RELATED ANTIGEN

[75] Inventors: Francis P. Kuhajda, Lutherville; Gary R. Pasternack, Baltimore, both of Md.

[73] Assignee: John Hopkins University, Baltimore, Md.

[21] Appl. No.: 469,005

[22] Filed: Jun. 5, 1995

Related U.S. Application Data

[60] Division of Ser. No. 188,426, Jan. 24, 1994, which is a continuation-in-part of Ser. No. 96,908, Jul. 26, 1993, abandoned, which is a continuation-in-part of Ser. No. 917,716, Jul. 24, 1992, abandoned, and a continuation-in-part of Ser. No. 735,522, Jul. 26, 1991, abandoned, which is a continuation-in-part of Ser. No. 622,407, Dec. 4, 1990, abandoned, which is a continuation of Ser. No. 297,722, Jan. 17, 1989, abandoned.

[51] Int. Cl.$^6$ ............... C07H 21/02; C07H 21/04; C12P 19/34; C12Q 1/68
[52] U.S. Cl. ............ 536/24.3; 536/22.1; 536/23.1; 536/24.31; 536/24.32; 536/24.33; 435/6; 435/912; 435/320.1; 435/325
[58] Field of Search ............... 536/22.1, 23.1, 536/24.3, 24.32, 24.33; 435/240.2, 91.2, 520.1, 6

[56] References Cited

U.S. PATENT DOCUMENTS

| | | |
|---|---|---|
| 3,535,509 | 10/1970 | Hata et al. |
| 3,630,846 | 12/1971 | Hata et al. |
| 3,897,428 | 7/1975 | Omura et al. |
| 3,909,361 | 9/1975 | Hata et al. |
| 4,000,164 | 12/1976 | Parker . |
| 4,011,334 | 3/1977 | Parker . |
| 4,032,647 | 6/1977 | Parker . |
| 4,110,351 | 8/1978 | Parker . |
| 4,328,246 | 5/1982 | Gold . |
| 4,602,099 | 7/1986 | Parker . |
| 4,738,984 | 4/1988 | Parker . |
| 4,789,630 | 12/1988 | Block et al. |
| 4,946,774 | 8/1990 | Oh . |
| 4,968,494 | 11/1990 | Claremon et al. |
| 5,143,907 | 9/1992 | Spielvogel . |
| 5,185,149 | 2/1993 | Baldwin et al. |
| 5,188,830 | 2/1993 | Atkinson et al. |
| 5,190,969 | 3/1993 | Blumenstein et al. |

FOREIGN PATENT DOCUMENTS

| | | |
|---|---|---|
| 0 246 734 | 11/1987 | European Pat. Off. |
| 0 374 886 | 6/1990 | European Pat. Off. |
| 252 616 | 12/1987 | Germany . |
| 59-255115 | 12/1984 | Japan . |
| 60-058917 | 4/1985 | Japan . |
| 01/132542 | 5/1989 | Japan . |
| 02/113850 | 4/1990 | Japan . |
| 02/247125 | 10/1990 | Japan . |
| WO 89/04963 | 6/1989 | WIPO . |

OTHER PUBLICATIONS

Bacchi, et al., "Effects of Some Antitumor Agents on Growth and Glycolytic Enzymes of the Flagellate Crithidia," Journal of Bacteriology. 98:23–28 (1969).

Furnica, et al., "Mecanismes Biochimiques Impliques Dans La Sensibilisation Des Organismes Vivants Par Des Agents Chimiques A L'Action Des Radiations et Des Cytostatiques," Rev. Roum. Bioshim., 8:117–122 (1971).

"Vivants Par Des Agents Chimiques A L'Action Des Radiations et Des Cytostatiques," Rev. Roum. Biochim., 8:117–122 (1971).

Omura, et al., "Relationship Between the Structures of Fatty Acid Amide Derivatives and Their Antimicrobial Activities," Antimicrobial Agents and Chemotherapy, 6:207–215 (1974).

Nery et al., "Isolation and Partial Characterization of Macromolecular Urinary Aggregates Containing Carcinoembryonic Antigen–Like Activity," British Jour. of Cancer (1974) 413–424.

Schroering, et al., "Fatty Acid Synthetase In Chemically Induced Mammary Carcinomas", Res. Communications In Chem. Path. and Pharmacology, (1974) 9:775–778.

Lin, et al., "Fatty Acid Synthetase from a Mouse Mammary Adenocarcinoma", Cancer Research, (1975) 35:3094–3099.

Abraham, et al., "Lipids and Lipogenesis in a Murine Mammary Neoplastic System", in Control Mechanisms in Cancer, Criss, et al eds., pp. 363–378, Raven Press, NY (1976).

Omura, Satoshi, "The Antibiotic Cerulenin, a Novel Tool for Biochemistry as an Inhibitor of Fatty Acid Synthesis," Bacteriological Reviews, 40:681–697 (1976).

Pitot, et al., "Contribution of the Morris Hepatomas to the Biochemistry of Cancer—Establishment of the Phenotypic Heterogeneity of Neoplasms In Vivo", Progress In Cancer Res. And Therapy, (1976) 1:21–37.

Partida, et al., "Comparative Effects of Diphenylglioxal and its Superoxide on Experimental Tumors," Arch. de Farmacol. y Toxicol., III:231–240 (1977).

Javid et al., "Human Haptoglobins," Curr. Topics in Hematology, (1978), 1:151–192.

Cooper et al., "Acute Phase Reactant Proteins in Cancer," Advances in Cancer Research, (1979), 30:1–44.

Ahmad, et al., "Increase in Fatty Acid Synthetase Content of 3T3-L Cells Undergoing Spontaneous and Chemically Induced Differentiation to Adipocytes", Biochem. J. (1979) 182:509–514.

(List continued on next page.)

Primary Examiner—George C. Elliott
Assistant Examiner—Jeffrey Fredman
Attorney, Agent, or Firm—Baker & Botts, L.L.P.

[57] ABSTRACT

A method of determining the prognosis of a solid tumor is provided, in which a sample from a patient bearing a tumor is assayed for the presence of a protein which is immunologically cross-reactive with the hpr gene product, but not with haptoglobin 1 or haptoglobin 2. Also provided is a method for preparing antibodies specific for this diagnostic marker which correlates with early relapse and metastasis of breast and other cancers. The marker can be detected using immunological methods employing antibodies specific for Hpr protein and not cross-reactive with haptoglobins 1 or 2.

10 Claims, 27 Drawing Sheets

(1 of 27 Drawing(s) in color)

OTHER PUBLICATIONS

Folkersen et al., "Affinity Chromatographic Purification of a New High Molecular Weight Pregnancy Specific Protein–SP–4," Carcino–Embryonic Proteins (1979), 2:503–508.

Davis et al., "Reactions with Simple Haptens," Microbiology, 3rd Ed., Harper & Row, pp. 298–306 (1980).

Sutcliffe et al., "Studies on Human Pregnancy–Associated Plasma Protein A," Biochem. Jour. (1980), 191:799–809.

Smith, et al., "Thioesterase II, a New Marker Enzyme for Human Cells of Breast Epithelial Origin," JNCI, 73:323–328 (1981).

Thompson, et al., "Purification and Properties Of Fatty Acid Synthetase From A Human Breast Cell Line", Biochim. Biophys. Acta, 662:125–130 (1981).

Omura, Satoshi, Chapter 39 "Cerulenin" in Methods in Enzymology, 72:520–532, 1981.

Ahmad, et al., "Inactivation of Rat Mammary Gland Fatty Acid Synthetase By S–(4–bromo–2,3–dioxobutyl)–Coenzyme", Fed. Proc. (1981) 40:1794 Abstract 1463.

Thompson, et al., "Lack of Coordinated Regulation Of Lipogenic Enzymes In A Human Breast Cell Line SKBr3", Biochim. Biophys. Acta, 712:217–220 (1982).

Clements, et al., "Irreversible Inhibition of Fatty Acid Synthase from Rat Mammary Gland with S–(4–bromo–2,3–dioxobutyl)–CoA", Biochem. J. (1982) 207:291–296.

Ahmad, et al., "Studies on Acetyl–CoA Carboxylase and Fatty Acid Synthase from Rat Mammary Gland and Mammary Tumors", Biochem. J. (1982) 208:443–452.

Baseler et al., "Purification of Haptoglobin and Its Effects on Lymphocyte and Alveolar Macrophage Responses," Inflammation, (1983), 7:387–400.

Haram et al., "Serum Protein Pattern in Normal Pregnancy with Special Reference to Acute–Phase Reactants," British Jour. of Obstetrics and Gynaecology (1983), 90:139–145.

Kuhajda et al., "The Distribution of Carcinoembryonic Antigen in Breast Carcinoma," Cancer (1983), 52:1257–1264.

Mendoza, et al., "Thermal Regulation of Membrane Fluidity in *Escherichia coli*," J. Biol. Chem., 258:2098–2101 (1983).

Spiegelman, et al., "Fibronectin Modulation of Cell Shape and Lipogenic Gene Expression in 3T2–Adipocytes", Cell (1983) 35:657–666.

Bischof, "Placental Proteins," Contributions to Gynecology and Obstetrics (1984), 12:1–5 and 41–74.

Maeda et al., "Duplication Within the Haptoglobin $Hp^2$ Gene," Nature, (1984),309:131–135.

Schindler et al., "Histochemical Localization of Pregnancy–Associated Plasma A in Fetal, Infant, and Adult Organs and Comparison Between Antisera," Gynecol. Obstet. Invest. (1984), 18:88–94.

Bischof, "Placenta Proteins," Contributions to Gynecology and Obstetrics (1984), 12:46–55.

Kuhajda et al., "Pregnancy–Specific Beta–1 Glycoprotein (SP–1) in Breast Carcinoma," Cancer (1984), 54:1392–1396.

Maeda, "Nucleotide Sequence of the Haptoglobin and Haptoglobin–Related Gene Pair," Jour. of Biol. Chem., (1985), 260:6698–6709.

Bensi et al., "Structure and Expression of the Human Haptoglobin Locus," The EMBO Journal, (1985) 4:119–126.

Kuhajda et al., "Pregnancy–Associated Plasma Protein A:A Clinically Significant Predictor of Early Recurrence in Stage I Breast Carcinoma is Independent of Estrogen Receptor Status", Am. J. Pathol. (1985), 121:342–348.

Kuhajda et al., "Pregnancy–Associated Plasma Protein A:A Clinically Significant Predictor of Early Recurrence in State II Breast Carcinoma," Hum. Pathol. (1985), 16:228–235.

Ceriani, et al., "Immunohistochemical Studies In Breast Cancer Using Monoclonal Antibodies Against Breast Epithelial Cell Components and With Lectins", Devel. Oncol., (1985) 34:233–63.

Hait, et al., "Inhibition of Growth of Leukemic Cells by Inhibitors Of Calmodulin: Phenothiazines and Melittin," Cancer Chemother. Pharmacol., 14:202–205 (1985).

Pawlak, et al., "Evaluation of Thioesterase II as a Serum Marker for Rat Mammary Cancer," Cancer Research, 46:4712–4719 (1986).

Mowles et al., "A Two–Site Immunoradiometric Assay for Human Pregnancy–Associated Plasma Protein A (PAPP–A) Using Monoclonal Antibodies", Journal of Immunological Methods, (1986) 95:129–133.

Maeda et al., "Polymorphisms in the Human Haptoglobin Gene Cluster: Chromosomes with Multiple Haptoglobin–Related (Hpr) Genes," Proc. Natl. Acad. Sci. USA (1986), 83:7395 7399.

Chemnitz et al., "Comparison of Different Antibody Preparations Against Pregnancy–Associated Plasma Protein–A (PAPP–A) for Use in Localization and Inmunoassay Studies," Br. Jour. of Obstetrics and Gynaecology (1986), 93:916–923.

Fujii, et al., "Effect of Cerulenin, an Inhibitor of Fatty Acid Synthesis, on the Immune Cytolysis of Tumor Cells", Jap. Jap. J. Exp. Med., 56:99–106 (1986).

Chalbos, et al., "Cloning of cDNA Sequences of a Progestin–Regulated mRNA from MCF7 Human Breast Cancer Cells", Nucl. Acids Res., 14:965–981 (1986).

Abraham, et al., "Lipid Metabolism and Enzyme Activities In Hormone–Dependent and Hormone–Independent Mammary Adenocarcinoma in GR Mice", JNCI (1986) 77:233–239.

Weiss, et al., "Fatty–Acid Biosynthesis in Man, a Pathway of Minor Importance", Biol. Chem. Hoppe–Seyler, (1986) 367:905–912.

Oh et al., "An Analogy Between Fetal Haptoglobin and a Potent Immunosuppressant in Cancer," Cancer Res., (1987), 47:5120–5126.

Thompson et al., "Elevated Levels of Abnormally–Fucosylated Haptoglobins in Cancer Sera," British Journ. of Cancer, (1987), 56:605–610.

Kuhajda et al., "Molecular Characterization of a Human Breast Cancer Antigen Predicting Early Relapse," Lab. Invest. (1987) vol. 56, Abstract 236.

Chalbos, et al., "Fatty Acid Synthetase and Its mRNA Are Induced By Progestins in Breast Cancer Cells", (1987) J. Biol. Chem., 262:9923–9926.

DAKO Corporation, Technical Information and Product List regarding anti–PAPP–A antiserum (1988).

McAllister, et al., "The Effect of Tumour Growth on Liver Pantothenate, CoA, and Fatty Acid Synthetase Activity in the Mouse", Br. J. Cancer (1988) 57:83–86.

Tisdale, et al., "Changes in Host Liver Fatty Acid Synthase in Tumour–Bearing Mice", Cancer Letters (1988) 42:231–235.

Wilder, et al., "Altered Rate and Fatty Acid Distribution in Adriamycin (P388A) Cells", Proceedings of AACR, (1988) 29:318 Abstr. 1265.

Joyeux, et al., "Progestin Increases Gene Transcription and Messenger Ribonucleic Acid Stability of Fatty Acid Synthetase in Breast Cancer Cells," Molecular Endocrinology, 4:681–686 (1989).

Bueler et al., "Antiserum to Pregnancy–Associated Plasma Protein A (PAPP–A) Recognizes Human Haptoglobin", Br. J. Ob. Gyn., (1989), 96:867–869.

Pasternack, et al., "Expression of Haptoglobin–related Protein (Hpr) Epitomes In Human Breast Carcinoma Correlates With Increased Phenotypic Malignancy", J. Cell. Biochem., 13B:137, Abstr. E410 (1989).

Shurbaji, et al., "Immunohistochemical Expression of Hpr In Primary And Metastatic Breast Carcinoma", Lab. Invest., 60:1, Abstr. 525 (1989).

Spydevold, et al., "Activities of Enzymes of Lipid Metabolism in Morris Hepatoma", Biochimica et Biophysica Acta (1989) 1003:80–83.

Funabashi, et al., "Binding Site of Cerulenin in Fatty Acid Synthetase," (1989) J. Biochem., 105:751–755.

Oh, et al., "Monoclonal Antibody to SER Immune Suppressor Detects Polymeric Forms of Haptoglobin," (1989) Hybridoma, 8:449–466.

Romanens, et al., "Cac'ing Safer with Cac'ing Spawning," Der Champignon, 1989, pp. 22–30.

Chambon, et al., "Progestins and Androgens Stimulate Lipid Accumulation In T47D Breast Cancer Cells Via Their Own Receptors", J. Steriod Biochem., 33:915–922 (1989).

Kuhajda et al., "Expression of Haptoglobin–Related Protein and its Potential Role as a Tumor Antigen", Proc. Natl. Acad. Sci. USA (1989), 86:1188–1192.

Kuhajda et el., "Haptoglobin–Related Protein (Hpr) Epitopes in Breast Cancer as a Predictor of Recurrence of the Disease", N. Eng. J. Med. (1989) 321:636–641.

Hourdou, et al., "Specific Inhibition of Iturin Biosynthesis by Cerulenin," Can. J. Microbiol., 36:164–168 (1990).

Amy, et al "Molecular Cloning of the Mammalian Fatty Acid Synthase Gene and Identification of the Promoter Region," Biochem. J., 271:675–679 (1990).

Chalbos, et al., "Expression of the Progestin–Induced Fatty Acid Synthetase in Benign Mastopathies and Breast Cancer as Measured by RNA in Situ Hybridiazation", JNCI, 82:602–606 (1990).

Escot, et al., "Regulation of Fatty Acid Synthetase Ribonucleic Acid In The Human Endometrium During the Menstrual Cycle", J. Clin. Endocrinol. Metab. 70:1319–1324 (1990).

Joyeux, et al., "Effects of Progestins and Menstrual Cycle on Fatty Acid Synthetase And Progesterone Receptor in Human Mammary Glands", J. Clin. Endocrinol. Metab., 70:1438–1444 (1990).

Chalbos, et al., "Progestin–Induced Fatty Acid Synthetase in Breast Cancer", Ann. N. Y. Acad. Sci., 1990, vol. 595, pp. 67–73

Fawcett, et al., "Identification of the Products of the Haptoglobin–Related Gene," Biochim Biophys. Acta, (1990) 1048:187–193.

Shurbaji, et al., "Expression of Haptoglobin Related Protein (Hpr) Epitopes By Prostate Carcinoma: A Potential Prognostic Indicator", Intl. Acad. Pathol. Mtg., Mar. 1991, Abstr. 300.

Ziegler, et al., "Current Status of Adjuvant Therapy of Early Breast Cancer", Am. J Clin. Oncol., 14:101–110 (1991) (Abstract only).

Corrigan, et al., "Prognostic Value of the Immunohistochemical Demonstration of Haptoglobin–Related Protein in Breast Cancer", A.J.C.P. Sep. 1991, p. 406 Abstr. 19.

Shurbaji, et al., "Expression of Oncogenic Antigen 519 (OA–519) in Prostate Cancer Is A Potential Prognostic Indicator", Am. J. Clin. Pathol., 97:686–691 (1992).

"Cancer Test Nearing Market", The Daily Record, Oct. 3 1991, pp. 3, 5.

"In Vitro Cancer Diagnostics", BioWorld Today, Oct. 7, 1991, p. 3.

"New Cancer Analytes: Finally, the Silver Bullet?", The Genesis Report, Dec. 1991/Jan. 1972, pp. 10–12.

Chalbos, et al., "The Anti–progestin RU486 Stabilizes the Progestin–induced Fatty Acid Synthetase mRNA but Does Not Stimulate Its Transcription", J. Biol. Chem., 266:8220–8224 (1991).

Redston, et al., "Expression of OA519 (Haptoglobin–Related Protein Epitopes) In Colorectal Carcinomas: Comparison With Molecular Genetic Alterations and Metastsis", Lab. Invest., 66:13A (1992), Abstr. 66.

Cote, et al., "Prognostic Features In Breast Carcinoma: Detection Of Occult Axillary Lymph Node Micrometastases (LNM), Expression of Haptoglobin Related Binding Protein (OA519) And Progesterone Receptor (PR) in Primary Tumors", Lab. Invest., 66:47A (1992), 77 Abstr. 272.

Redston, et al., "Expression of OA519 (Haptoglobin–Related Protein Epitopes) In Cotorectal and Carcinomas: Comparison With Molecular Genetic Alterations and Metastasis", Lab Invest., 66:47A (1992), Abst. 272.

Martin, et al., "Immunohistochemical Expression of OA–519 In Pre–Neoplastic and Neoplastic Lesion Polyps of the Colon," American Society for Clinical Oncology, (Abstract).

Maniatis et al, Molecular Cloning: A Laboratory Manual, Cold Spring Harbor laboratory Press, Cold Spring Harbor, New York, pp. 403–433. 1982

O'Brien et al., "Qualitative Analysis of Proteinuria Associated with Bladder Cancer," Investigative Urology, (1979), 17:28–32.

FIG. 3

| SOURCE OF SEQUENCE | | |
|---|---|---|
| EXPERIMENTAL | | ILGGHLDAKGSFPWQAKMVS |
| HpR | 93 | KPKNPANPVQRILGGHLDAKGSFPWQAKMVSHHNLTTGATLI |
| Hp-1 | 73 | PKPKNPANPVQILGGHLDAKGSFPWQAKMVSHHNLTTGATLI |
| Hp-2 | 151 | KPKNPANPVQRILGGHLDAKGSFPWQAKMVSHHNLTTGATLI |

FIG. 10A
FIG. 10B
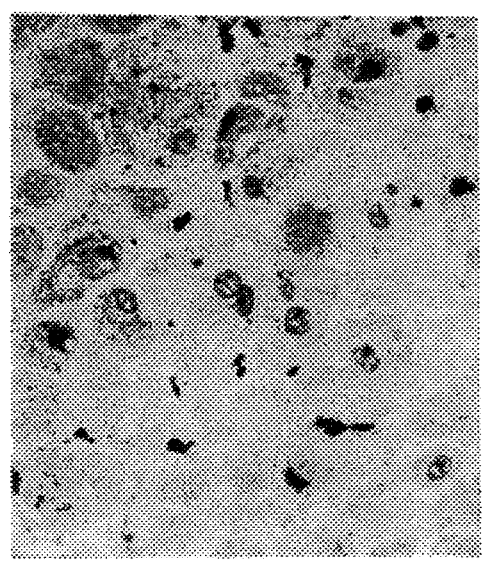

FIG. 12B

Sequence 1: Analysis of 134 kD OA-519 peptide sequence homology.

OA-519 peptide sequence:  LQQHDVAQEQWXP
                          ||||||| ||:|
Rat fatty acid synthase (EC 2.3.1.85): TKLQQHDVAQGQWDPSGPAPTNLGALD
                                         1290         1300

84.6% identity in 13 amino acid overlap.

Sequence 2: Analysis of OA-519 peptide sequence from Example 12 of the Continuation-In-Part of U.S. Serial No. 07/735522 filed July 26, 1991.

OA-519 peptide sequence:  HAVVLE
                          ||||||
Rat fatty acid synthase (EC 2.3.1.85): HAVVLE 100% identity in 6 amino acid overlap.

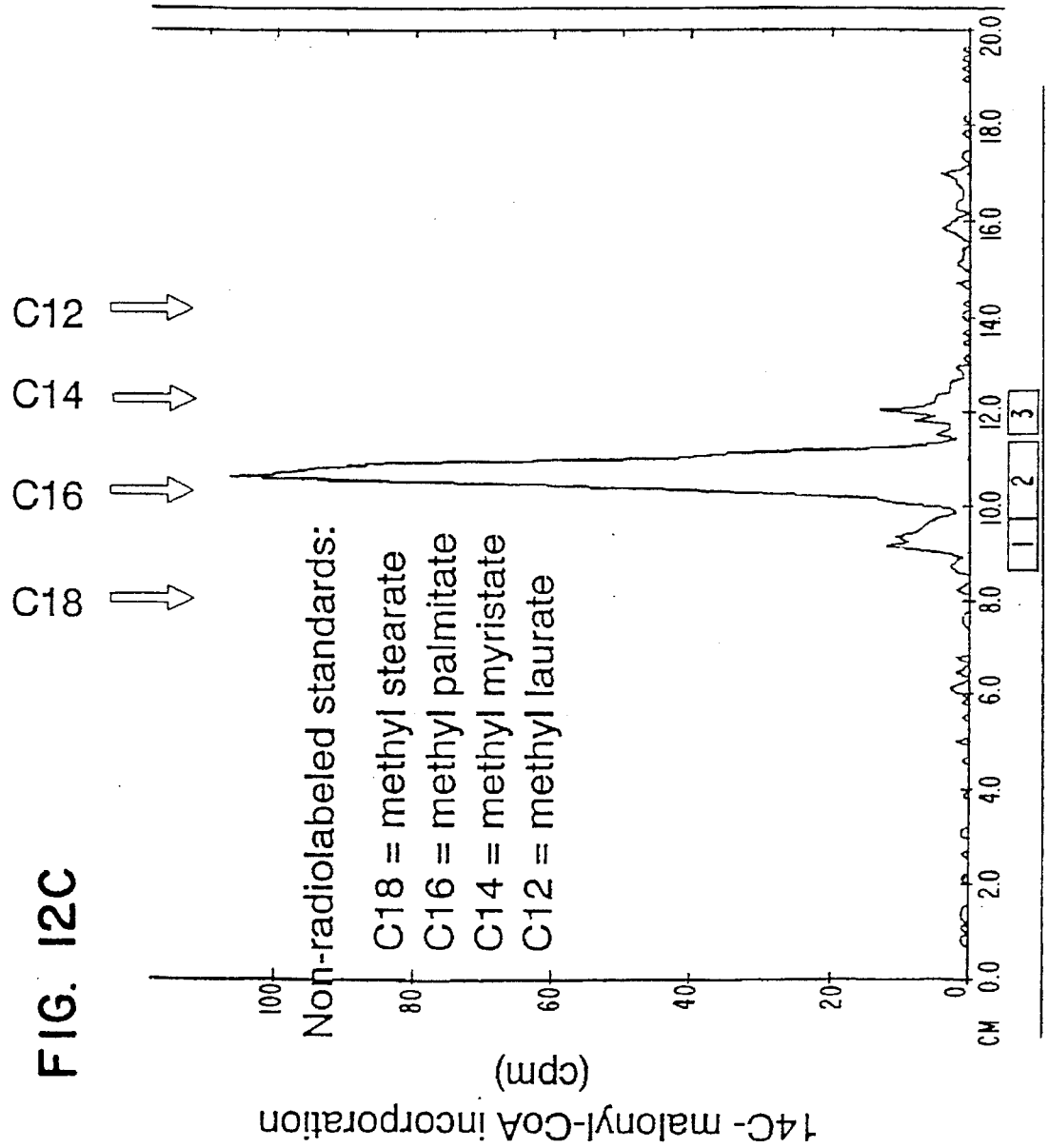

FIG. 15A
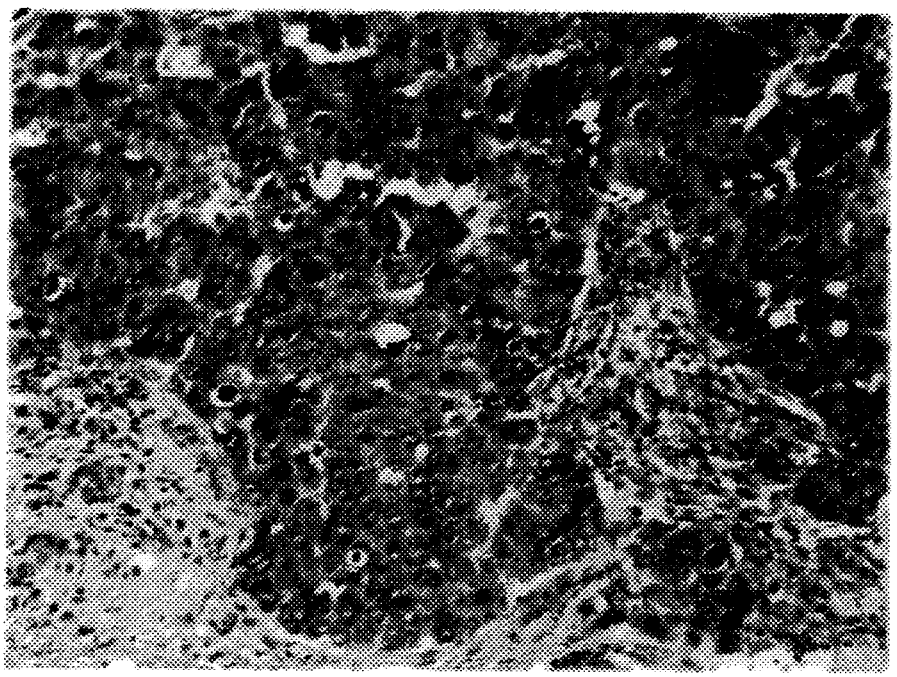
FIG. 15B

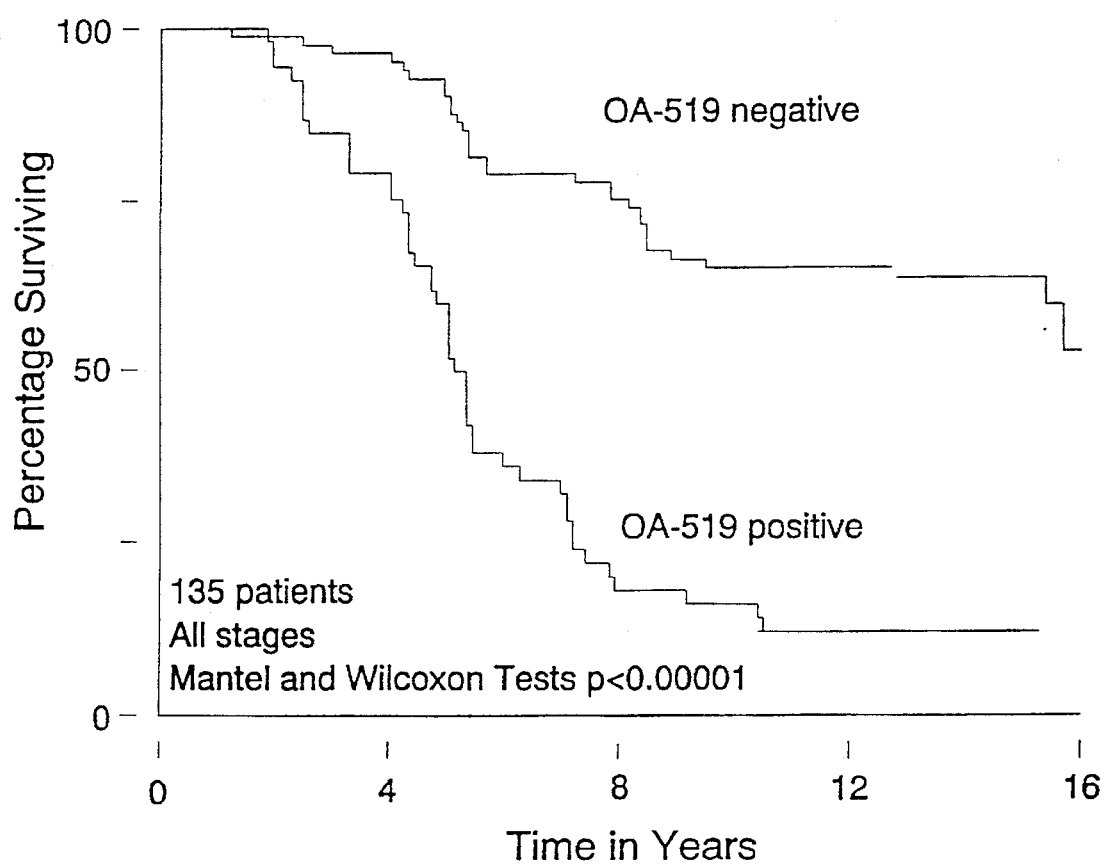

FIG. 21
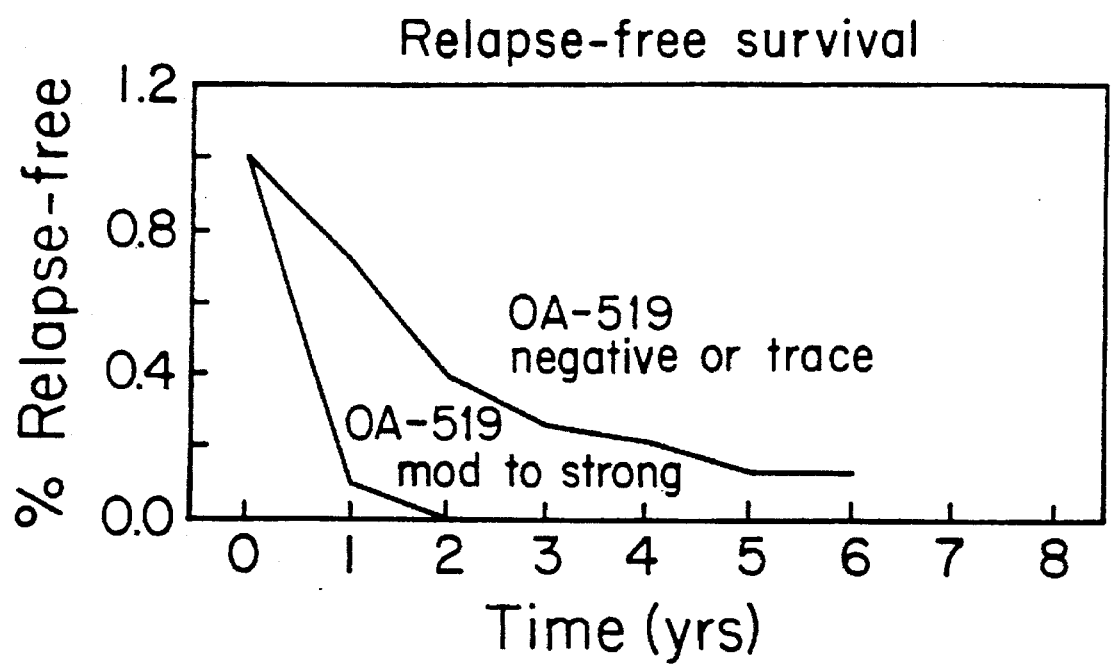
p-value less than .05
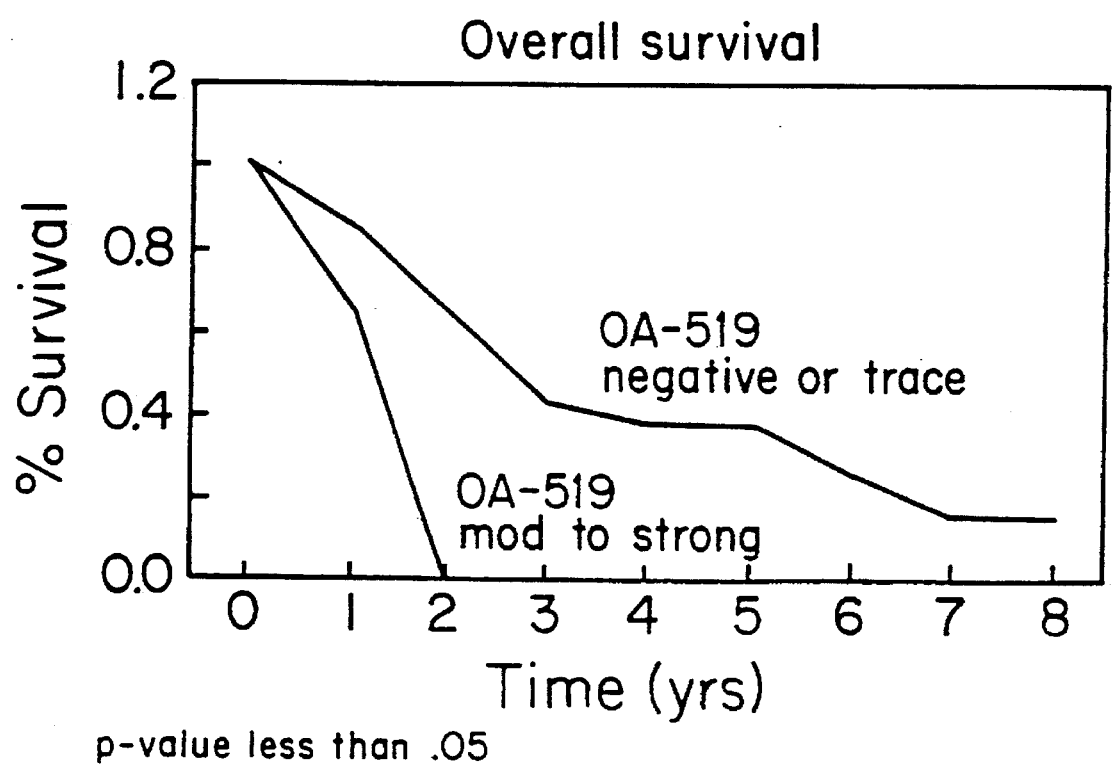
p-value less than .05

NED = No Clinical Evidence of Disease at Time of Measurement

SEQUENCE LISTING ( 1 ) GENERAL INFORMATION:

( i i i ) NUMBER OF SEQUENCES: 14

( 2 ) INFORMATION FOR SEQ ID NO:1:

( i ) SEQUENCE CHARACTERISTICS:
        ( A ) LENGTH: 34 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:1:

```
Leu Tyr Ser Gly Asn Asp Val Thr Asp Ile Ser Asp Asp Arg Phe Pro
 1               5                  10                  15
Lys Pro Pro Glu Ile Ala Asn Gly Tyr Val Glu Lys Leu Phe Arg Tyr
                20                  25                  30
Gln Cys
```

( 2 ) INFORMATION FOR SEQ ID NO:2:

( i ) SEQUENCE CHARACTERISTICS:
    ( A ) LENGTH: 7 amino acids
    ( B ) TYPE: amino acid
    ( C ) STRANDEDNESS: single
    ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( v i ) ORIGINAL SOURCE:

( x i ) SEQUENCE DESCRIPTION: SEQ ID NO:2:

```
Phe  Ala  Ala  Leu  Gln  Glu  Glu
 1                    5
```

( 2 ) INFORMATION FOR SEQ ID NO:3:

( i ) SEQUENCE CHARACTERISTICS:
        ( A ) LENGTH: 19 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( v i ) ORIGINAL SOURCE:

( x i ) SEQUENCE DESCRIPTION: SEQ ID NO:3:

```
His  Pro  Glu  Ser  Pro  Thr  Pro  Asn  Pro  Thr  Glu  Pro  Leu  Phe  Leu  Ala
 1                    5                        10                        15
Gln  Ala  Glu
```

( 2 ) INFORMATION FOR SEQ ID NO:4:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( v i ) ORIGINAL SOURCE:

( x i ) SEQUENCE DESCRIPTION: SEQ ID NO:4:

```
His  Ala  Val  Val  Leu  Glu
 1                    5
```

( 2 ) INFORMATION FOR SEQ ID NO:5:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear (ii) MOLECULE TYPE: peptide (iii) HYPOTHETICAL: NO (iv) ANTI-SENSE: NO (v) FRAGMENT TYPE: N-terminal (vi) ORIGINAL SOURCE:

(xi) SEQUENCE DESCRIPTION: SEQ ID NO:5:

Arg Ala Ala Leu Gln Glu
1               5

(2) INFORMATION FOR SEQ ID NO:6:

(i) SEQUENCE CHARACTERISTICS:
    (A) LENGTH: 58 base pairs
    (B) TYPE: nucleic acid
    (C) STRANDEDNESS: single
    (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:6:

GGGCCTGGAG TCTATCATCA ACATCATCCA CAGCTCCCTG GCTGAGCCTC GAGTGAGT    58

(2) INFORMATION FOR SEQ ID NO:7:

(i) SEQUENCE CHARACTERISTICS:
    (A) LENGTH: 35 base pairs
    (B) TYPE: nucleic acid
    (C) STRANDEDNESS: single
    (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:7:

AACAACCACC CTCTGGGCAT GGCCATCTTC TTGAA    35

(2) INFORMATION FOR SEQ ID NO:8:

(i) SEQUENCE CHARACTERISTICS:
    (A) LENGTH: 25 base pairs
    (B) TYPE: nucleic acid
    (C) STRANDEDNESS: single
    (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

( x i ) SEQUENCE DESCRIPTION: SEQ ID NO:8:

AGAACTCCAT ACCTAGCAGG CTGTC                                                                 25

( 2 ) INFORMATION FOR SEQ ID NO:9:

( i ) SEQUENCE CHARACTERISTICS:
        ( A ) LENGTH: 8460 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( i x ) FEATURE:
        ( A ) NAME/KEY: Coding Sequence
        ( B ) LOCATION: 124...7650
        ( D ) OTHER INFORMATION:

( x i ) SEQUENCE DESCRIPTION: SEQ ID NO:9:

```
CGGCCGTCGA CACGGCAGCG GCCCCGGCCT CCCTCTCCGC CGCGCTTCAG CCTCCCGCTC        60

CGCCGCGCTC CAGCCTCGCT CTCCGCCGCC CGCACCGCCG CCCGCGCCCT CACCAGAGCA       120

GCC ATG GAG GAG GTG GTG ATT GCC GGC ATG TCC GGG AAG CTG CCA GAG         168
    Met Glu Glu Val Val Ile Ala Gly Met Ser Gly Lys Leu Pro Glu
    1               5                   10                  15

TCG GAG AAC TTG CAG GAG TTC TGG GAC AAC CTC ATC GGC GGT GTG GAC         216
Ser Glu Asn Leu Gln Glu Phe Trp Asp Asn Leu Ile Gly Gly Val Asp
                20                  25                  30

ATG GTC ACG GAC GAT GAC CGT CGC TGG AAG GCG GGC CTC TAC GGC CTG         264
Met Val Thr Asp Asp Asp Arg Arg Trp Lys Ala Gly Leu Tyr Gly Leu
            35                  40                  45

CCC CGG CGG TCC GGC AAG CTG AAG GAC CTG TCT AGG TTT GAT GCC TCC         312
Pro Arg Arg Ser Gly Lys Leu Lys Asp Leu Ser Arg Phe Asp Ala Ser
        50                  55                  60

TTC TTC GGA GTC CAC CCC AAG CAG GCA CAC ACG ATG GAC CCT CAG CTG         360
Phe Phe Gly Val His Pro Lys Gln Ala His Thr Met Asp Pro Gln Leu
    65                  70                  75

CGG CTG CTG CTG GAA GTC ACC TAT GAA GCC ATC GTG GAC GGA GGC ATC         408
Arg Leu Leu Leu Glu Val Thr Tyr Glu Ala Ile Val Asp Gly Gly Ile
80                  85                  90                  95

AAC CCA GAT TCA CTC CGA GGA ACA CAC ACT GGC GTC TGG GTG GGC GTG         456
Asn Pro Asp Ser Leu Arg Gly Thr His Thr Gly Val Trp Val Gly Val
                100                 105                 110

AGC GGC TCT GAG ACC TCG GAG GCC CTG AGC CGA GAC CCC GAG ACA CTC         504
Ser Gly Ser Glu Thr Ser Glu Ala Leu Ser Arg Asp Pro Glu Thr Leu
            115                 120                 125

GTG GGC TAC AGC ATG GTG GGC TGC CAG CGA GCG ATG ATG GCC AAC CGG         552
Val Gly Tyr Ser Met Val Gly Cys Gln Arg Ala Met Met Ala Asn Arg
        130                 135                 140

CTC TCC TTC TTC TTC GAC TTC AGA GGG CCC AGC ATC GCA CTG GAC ACA         600
Leu Ser Phe Phe Phe Asp Phe Arg Gly Pro Ser Ile Ala Leu Asp Thr
    145                 150                 155

GCC TGC TCC TCC AGC CTG ATG GCC CTG CAG AAC GCC TAC CAG GCC ATC         648
Ala Cys Ser Ser Ser Leu Met Ala Leu Gln Asn Ala Tyr Gln Ala Ile
160                 165                 170                 175

CAC AGC GGG CAG TGC CCT GCC GCC ATC GTG GGG GGC ATC AAT GTC CTG         696
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| His | Ser | Gly | Gln | Cys | Pro | Ala | Ala | Ile | Val | Gly | Gly | Ile | Asn | Val | Leu |      |
|     |     |     |     | 180 |     |     |     | 185 |     |     |     |     |     | 190 |     |      |
| CTG | AAG | CCC | AAC | ACC | TCC | GTG | CAG | TTC | TTG | AGG | CTG | GGG | ATG | CTC | AGC | 744  |
| Leu | Lys | Pro | Asn | Thr | Ser | Val | Gln | Phe | Leu | Arg | Leu | Gly | Met | Leu | Ser |      |
|     |     |     | 195 |     |     |     | 200 |     |     |     |     | 205 |     |     |     |      |
| CCC | GAG | GGC | ACC | TGC | AAG | GCC | TTC | GAC | ACA | GCG | GGG | AAT | GGG | TAC | TGC | 792  |
| Pro | Glu | Gly | Thr | Cys | Lys | Ala | Phe | Asp | Thr | Ala | Gly | Asn | Gly | Tyr | Cys |      |
|     |     | 210 |     |     |     |     | 215 |     |     |     |     | 220 |     |     |     |      |
| CGC | TCG | GAG | GGT | GTG | GTG | GCC | GTC | CTG | CTG | ACC | AAG | AAG | TCC | CTG | GCC | 840  |
| Arg | Ser | Glu | Gly | Val | Val | Ala | Val | Leu | Leu | Thr | Lys | Lys | Ser | Leu | Ala |      |
|     | 225 |     |     |     | 230 |     |     |     |     | 235 |     |     |     |     |     |      |
| CGG | CGG | GTG | TAC | GCC | ACC | ATC | CTG | AAC | GCC | GGC | ACC | AAT | ACA | GAT | GGC | 888  |
| Arg | Arg | Val | Tyr | Ala | Thr | Ile | Leu | Asn | Ala | Gly | Thr | Asn | Thr | Asp | Gly |      |
| 240 |     |     |     | 245 |     |     |     |     | 250 |     |     |     |     | 255 |     |      |
| TTC | AAG | GAG | CAA | GGC | GTG | ACC | TTC | CCC | TCA | GGG | GAT | ATC | CAG | GAG | CAG | 936  |
| Phe | Lys | Glu | Gln | Gly | Val | Thr | Phe | Pro | Ser | Gly | Asp | Ile | Gln | Glu | Gln |      |
|     |     |     |     | 260 |     |     |     |     | 265 |     |     |     |     | 270 |     |      |
| CTC | ATC | CGC | TCG | TTG | TAC | CAG | TCG | GCC | GGA | GTG | GCC | CCT | GAG | TCA | TTT | 984  |
| Leu | Ile | Arg | Ser | Leu | Tyr | Gln | Ser | Ala | Gly | Val | Ala | Pro | Glu | Ser | Phe |      |
|     |     |     | 275 |     |     |     |     | 280 |     |     |     |     | 285 |     |     |      |
| GAA | TAC | ATC | GAA | GCC | CAC | GGC | ACA | GGC | ACC | AAG | GTG | GGC | GAC | CCC | CAG | 1032 |
| Glu | Tyr | Ile | Glu | Ala | His | Gly | Thr | Gly | Thr | Lys | Val | Gly | Asp | Pro | Gln |      |
|     |     | 290 |     |     |     |     | 295 |     |     |     |     | 300 |     |     |     |      |
| GAG | CTG | AAT | GGC | ATC | ACC | CGA | GCC | CTG | TGC | GCC | ACC | CGC | CAG | GAG | CCG | 1080 |
| Glu | Leu | Asn | Gly | Ile | Thr | Arg | Ala | Leu | Cys | Ala | Thr | Arg | Gln | Glu | Pro |      |
|     | 305 |     |     |     |     | 310 |     |     |     |     | 315 |     |     |     |     |      |
| CTG | CTC | ATC | GGC | TCC | ACC | AAG | TCC | AAC | ATG | GGG | CAC | CCG | GAG | CCA | GCC | 1128 |
| Leu | Leu | Ile | Gly | Ser | Thr | Lys | Ser | Asn | Met | Gly | His | Pro | Glu | Pro | Ala |      |
| 320 |     |     |     |     | 325 |     |     |     |     | 330 |     |     |     |     | 335 |      |
| TCG | GGG | CTG | GCA | GCC | CTG | GCC | AAG | GTG | CTG | CTG | TCC | CTG | GAG | CAC | GGG | 1176 |
| Ser | Gly | Leu | Ala | Ala | Leu | Ala | Lys | Val | Leu | Leu | Ser | Leu | Glu | His | Gly |      |
|     |     |     |     | 340 |     |     |     |     | 345 |     |     |     |     | 350 |     |      |
| CTC | TGG | GCC | CCC | AAC | CTG | CAC | TTC | CAT | AGC | CCC | AAC | CCT | GAG | ATC | CCA | 1224 |
| Leu | Trp | Ala | Pro | Asn | Leu | His | Phe | His | Ser | Pro | Asn | Pro | Glu | Ile | Pro |      |
|     |     |     | 355 |     |     |     |     | 360 |     |     |     |     | 365 |     |     |      |
| GCG | CTG | TTG | GAT | GGG | CGG | CTG | CAG | GTG | GTG | GAC | CAG | CCC | CTG | CCC | GTC | 1272 |
| Ala | Leu | Leu | Asp | Gly | Arg | Leu | Gln | Val | Val | Asp | Gln | Pro | Leu | Pro | Val |      |
|     |     | 370 |     |     |     | 375 |     |     |     |     | 380 |     |     |     |     |      |
| CGT | GGC | GGC | AAC | GTG | GGC | ATC | AAC | TCC | TTT | GGC | TTC | GGG | GGC | TCC | AAC | 1320 |
| Arg | Gly | Gly | Asn | Val | Gly | Ile | Asn | Ser | Phe | Gly | Phe | Gly | Gly | Ser | Asn |      |
| 385 |     |     |     |     | 390 |     |     |     |     | 395 |     |     |     |     |     |      |
| GTG | CAC | ATC | ATC | CTG | AGG | CCC | AAC | ACG | CAG | CCG | CCC | CCA | GCA | CCC | GCC | 1368 |
| Val | His | Ile | Ile | Leu | Arg | Pro | Asn | Thr | Gln | Pro | Pro | Pro | Ala | Pro | Ala |      |
| 400 |     |     |     |     | 405 |     |     |     |     | 410 |     |     |     |     | 415 |      |
| CCA | CAT | GCC | ACC | CTG | CCC | CGT | CTG | CTG | CGG | GCC | AGC | GGA | CGC | ACC | CCT | 1416 |
| Pro | His | Ala | Thr | Leu | Pro | Arg | Leu | Leu | Arg | Ala | Ser | Gly | Arg | Thr | Pro |      |
|     |     |     |     | 420 |     |     |     |     | 425 |     |     |     |     | 430 |     |      |
| GAG | GCC | GTG | CAG | AAG | CTG | CTG | GAG | CAG | GGC | CTC | CGG | CAC | AGC | CAG | GAC | 1464 |
| Glu | Ala | Val | Gln | Lys | Leu | Leu | Glu | Gln | Gly | Leu | Arg | His | Ser | Gln | Asp |      |
|     |     |     | 435 |     |     |     |     | 440 |     |     |     |     | 445 |     |     |      |
| CTG | GCT | TTC | CTG | AGC | ATG | CTG | AAC | GAC | ATC | GCG | CTG | TCC | CCG | ACC | ACC | 1512 |
| Leu | Ala | Phe | Leu | Ser | Met | Leu | Asn | Asp | Ile | Ala | Leu | Ser | Pro | Thr | Thr |      |
|     |     |     | 450 |     |     |     |     | 455 |     |     |     |     | 460 |     |     |      |
| GCC | ATG | CCC | TTC | CGT | GGC | TAC | GCT | GTG | CTG | GGT | GGT | GAG | CGC | GGT | GGC | 1560 |
| Ala | Met | Pro | Phe | Arg | Gly | Tyr | Ala | Val | Leu | Gly | Gly | Glu | Arg | Gly | Gly |      |
|     | 465 |     |     |     |     | 470 |     |     |     |     | 475 |     |     |     |     |      |
| CCA | GAG | GTG | CAG | CAG | GTG | CCC | GCT | GGC | GAG | CGC | CCG | CTC | TGG | TTC | ATC | 1608 |
| Pro | Glu | Val | Gln | Gln | Val | Pro | Ala | Gly | Glu | Arg | Pro | Leu | Trp | Phe | Ile |      |
| 480 |     |     |     |     | 485 |     |     |     |     | 490 |     |     |     |     | 495 |      |
| TGC | TCT | GGG | ATG | GGC | ACA | CAG | TGG | CGC | GGG | ATG | GGG | CTG | AGC | CTC | ATG | 1656 |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| Cys | Ser | Gly | Met | Gly 500 | Thr | Gln | Trp | Arg | Gly 505 | Met | Gly | Leu | Ser | Leu 510 | Met |      |
| CGC | CTG | GAC | CGC | TTC | CGA | GAT | TCC | ATC | CTA | CGC | TCC | GAT | GAG | GCT | GTG | 1704 |
| Arg | Leu | Asp | Arg 515 | Phe | Arg | Asp | Ser | Ile 520 | Leu | Arg | Ser | Asp | Glu 525 | Ala | Val |      |
| AAC | CGA | TTC | GGC | CTG | AAG | GTG | TCA | CAG | CTG | CTG | CTG | AGC | ACA | GAC | GAG | 1752 |
| Asn | Arg | Phe 530 | Gly | Leu | Lys | Val | Ser 535 | Gln | Leu | Leu | Leu | Ser 540 | Thr | Asp | Glu |      |
| AGC | ACC | TTT | GAT | GAC | ATC | GTC | CAT | TCG | TTT | GTG | AGC | CTG | ACT | GCC | ATC | 1800 |
| Ser | Thr | Phe | Asp | Asp 545 | Ile | Val | His | Ser 550 | Phe | Val | Ser | Leu 555 | Thr | Ala | Ile |      |
| CAG | ATA | GGC | CTC | ATA | GAC | CTG | CTG | AGC | TGC | ATG | GGG | CTG | AGG | CCA | GAT | 1848 |
| Gln 560 | Ile | Gly | Leu | Ile | Asp 565 | Leu | Leu | Ser | Cys | Met 570 | Gly | Leu | Arg | Pro | Asp 575 |      |
| GGC | ATC | GTC | GGC | CAC | TCC | CTG | GGG | GAG | GTG | GCC | TGT | GGC | TAC | GCC | GAC | 1896 |
| Gly | Ile | Val | Gly | His 580 | Ser | Leu | Gly | Glu | Val 585 | Ala | Cys | Gly | Tyr | Ala 590 | Asp |      |
| GGC | TGC | CTG | TCC | CAG | GAG | GAG | GCC | GTC | CTC | GCT | GCC | TAC | TGG | AGG | GGA | 1944 |
| Gly | Cys | Leu | Ser 595 | Gln | Glu | Glu | Ala | Val 600 | Leu | Ala | Ala | Tyr | Trp 605 | Arg | Gly |      |
| CAG | TGC | ATC | AAA | GAA | GCC | CAT | CTC | CCG | CCG | GGC | GCC | ATG | GCA | GCC | GTG | 1992 |
| Gln | Cys | Ile 610 | Lys | Glu | Ala | His | Leu 615 | Pro | Pro | Gly | Ala | Met 620 | Ala | Ala | Val |      |
| GGC | TTG | TCC | TGG | GAG | GAG | TGT | AAA | CAG | CGC | TGC | CCC | CCG | GCG | GTG | GTG | 2040 |
| Gly | Leu 625 | Ser | Trp | Glu | Glu | Cys 630 | Lys | Gln | Arg | Cys | Pro 635 | Pro | Ala | Val | Val |      |
| CCC | GCC | TGC | CAC | AAC | TCC | AAG | GAC | ACA | GTC | ACC | ATC | TCG | GGA | CCT | CAG | 2088 |
| Pro | Ala | Cys | His | Asn 645 | Ser | Lys | Asp | Thr | Val 650 | Thr | Ile | Ser | Gly | Pro 655 | Gln |      |
| Pro 640 |     |     |     |     |     |     |     |     |     |     |     |     |     |     |     |      |
| GCC | CCG | GTG | TTT | GAG | TTC | GTG | GAG | CAG | CTG | AGG | AAG | GAG | GGT | GTG | TTT | 2136 |
| Ala | Pro | Val | Phe | Glu 660 | Phe | Val | Glu | Gln | Leu 665 | Arg | Lys | Glu | Gly | Val 670 | Phe |      |
| GCC | AAG | GAG | GTG | CGG | ACC | GGC | GGT | ATG | GCC | TTC | CAC | TCC | TAC | TTC | ATG | 2184 |
| Ala | Lys | Glu | Val 675 | Arg | Thr | Gly | Gly | Met 680 | Ala | Phe | His | Ser | Tyr 685 | Phe | Met |      |
| GAG | GCC | ATC | GCA | CCC | CCA | CTG | CTG | CAG | GAG | CTC | AAG | AAG | GTG | ATC | CGG | 2232 |
| Glu | Ala | Ile | Ala 690 | Pro | Pro | Leu | Leu | Gln 695 | Glu | Leu | Lys | Lys | Val 700 | Ile | Arg |      |
| GAG | CCG | AAG | CCA | CGT | TCA | GCC | CGC | TGG | CTC | AGC | ACC | TCT | ATC | CCC | GAG | 2280 |
| Glu | Pro | Lys 705 | Pro | Arg | Ser | Ala | Arg 710 | Trp | Leu | Ser | Thr | Ser 715 | Ile | Pro | Glu |      |
| GCC | CAG | TGG | CAC | AGC | AGC | CTG | GCA | CGC | ACG | TCC | TCC | GCC | GAG | TAC | AAT | 2328 |
| Ala 720 | Gln | Trp | His | Ser | Ser 725 | Leu | Ala | Arg | Thr | Ser 730 | Ser | Ala | Glu | Tyr | Asn 735 |      |
| GTC | AAC | AAC | CTG | GTG | AGC | CCT | GTG | CTG | TTC | CAG | GAG | GCC | CTG | TGG | CAC | 2376 |
| Val | Asn | Asn | Leu | Val 740 | Ser | Pro | Val | Leu | Phe 745 | Gln | Glu | Ala | Leu | Trp 750 | His |      |
| GTG | CCT | GAG | CAC | GCG | GTG | GTG | CTG | GAG | ATC | GCG | CCC | CAC | GCC | CTG | CTG | 2424 |
| Val | Pro | Glu | His 755 | Ala | Val | Val | Leu | Glu 760 | Ile | Ala | Pro | His | Ala 765 | Leu | Leu |      |
| CAG | GCT | GTC | CTG | AAG | CGT | GGC | CTG | AAG | CCG | AGC | TGC | ACC | ATC | ATC | CCC | 2472 |
| Gln | Ala | Val 770 | Leu | Lys | Arg | Gly | Leu 775 | Lys | Pro | Ser | Cys | Thr 780 | Ile | Ile | Pro |      |
| CTG | ATG | AAG | AAG | GAT | CAC | AGG | GAC | AAC | CTG | GAG | TTC | TTC | CTG | GCC | GGC | 2520 |
| Leu | Met | Lys 785 | Lys | Asp | His | Arg | Asp 790 | Asn | Leu | Glu | Phe | Phe 795 | Leu | Ala | Gly |      |
| ATC | CGG | AGG | CTG | CAC | CTC | TCA | GGC | ATC | GAC | GCC | AAC | CCC | AAT | GCC | TTG | 2568 |
| Ile 800 | Arg | Arg | Leu | His | Leu 805 | Ser | Gly | Ile | Asp | Ala 810 | Asn | Pro | Asn | Ala | Leu 815 |      |
| TTC | CCA | CCT | GTG | GAG | TTC | CCA | GCT | CCC | CGA | GGA | ACT | CCC | CTC | ATC | TCC | 2616 |

|     |     |     |     |     |     |     |     |     |     |     |     |     |     |     |     |
| --- | --- | --- | --- | --- | --- | --- | --- | --- | --- | --- | --- | --- | --- | --- | --- |
| Phe | Pro | Pro | Val | Glu | Phe | Pro | Ala | Pro | Arg | Gly | Thr | Pro | Leu | Ile | Ser |
|     |     |     |     | 820 |     |     |     | 825 |     |     |     |     |     | 830 |     |
| CCA | CTC | ATC | AAG | TGG | GAC | CAC | AGC | CTG | GCC | TGG | GAC | GTG | CCG | GCC | GCC | 2664 |
| Pro | Leu | Ile | Lys | Trp | Asp | His | Ser | Leu | Ala | Trp | Asp | Val | Pro | Ala | Ala |
|     |     |     | 835 |     |     |     | 840 |     |     |     |     | 845 |     |     |     |
| GAG | GAC | TTC | CCC | AAC | GGT | TCA | GGT | TCC | CCC | TCA | GCC | GCC | ATC | TAC | AAC | 2712 |
| Glu | Asp | Phe | Pro | Asn | Gly | Ser | Gly | Ser | Pro | Ser | Ala | Ala | Ile | Tyr | Asn |
|     |     | 850 |     |     |     |     | 855 |     |     |     |     | 860 |     |     |     |
| ATC | GAC | ACC | AGC | TCC | GAG | TCT | CCT | GAC | CAC | TAC | CTG | GTG | GAC | CAC | ACC | 2760 |
| Ile | Asp | Thr | Ser | Ser | Glu | Ser | Pro | Asp | His | Tyr | Leu | Val | Asp | His | Thr |
|     | 865 |     |     |     |     | 870 |     |     |     |     | 875 |     |     |     |     |
| CTC | GAC | GGT | CGC | GTC | CTC | TTC | CCC | GCC | ACT | GGC | TAC | CTG | AGC | ATA | GTG | 2808 |
| Leu | Asp | Gly | Arg | Val | Leu | Phe | Pro | Ala | Thr | Gly | Tyr | Leu | Ser | Ile | Val |
| 880 |     |     |     |     | 885 |     |     |     |     | 890 |     |     |     |     | 895 |
| TGG | AAG | ACG | CTG | GCC | CGA | CCC | CTG | GGC | CTG | GGC | GTC | GAG | CAG | CTG | CCT | 2856 |
| Trp | Lys | Thr | Leu | Ala | Arg | Pro | Leu | Gly | Leu | Gly | Val | Glu | Gln | Leu | Pro |
|     |     |     |     | 900 |     |     |     |     | 905 |     |     |     |     | 910 |     |
| GTG | GTG | TTT | GAG | GAT | GTG | GTG | CTG | CAC | CAG | GCC | ACC | ATC | CTG | CCC | AAG | 2904 |
| Val | Val | Phe | Glu | Asp | Val | Val | Leu | His | Gln | Ala | Thr | Ile | Leu | Pro | Lys |
|     |     |     | 915 |     |     |     | 920 |     |     |     |     | 925 |     |     |     |
| ACT | GGG | ACA | GTG | TCC | CTG | GAG | GTA | CGG | CTC | CTG | GAG | GCC | TCC | CGT | GCC | 2952 |
| Thr | Gly | Thr | Val | Ser | Leu | Glu | Val | Arg | Leu | Leu | Glu | Ala | Ser | Arg | Ala |
|     |     | 930 |     |     |     |     | 935 |     |     |     |     | 940 |     |     |     |
| TTC | GAG | GTG | TCA | GAG | AAC | GGC | AAC | CTG | GTA | GTG | AGT | GGG | AAG | GTG | TAC | 3000 |
| Phe | Glu | Val | Ser | Glu | Asn | Gly | Asn | Leu | Val | Val | Ser | Gly | Lys | Val | Tyr |
|     | 945 |     |     |     |     | 950 |     |     |     |     | 955 |     |     |     |     |
| CAG | TGG | GAT | GAC | CCT | GAC | CCC | AGG | CTC | TTC | GAC | CAC | CCG | GAA | AGC | CCC | 3048 |
| Gln | Trp | Asp | Asp | Pro | Asp | Pro | Arg | Leu | Phe | Asp | His | Pro | Glu | Ser | Pro |
| 960 |     |     |     |     | 965 |     |     |     |     | 970 |     |     |     |     | 975 |
| ACC | CCC | AAC | CCC | ACG | GAG | CCC | CTC | TTC | CTG | GCC | CAG | GCT | GAA | GTT | TAC | 3096 |
| Thr | Pro | Asn | Pro | Thr | Glu | Pro | Leu | Phe | Leu | Ala | Gln | Ala | Glu | Val | Tyr |
|     |     |     |     | 980 |     |     |     |     | 985 |     |     |     |     | 990 |     |
| AAG | GAG | CTG | CGT | CTG | CGT | GGC | TAC | GAC | TAC | GGC | CCT | CAT | TTC | CAG | GGC | 3144 |
| Lys | Glu | Leu | Arg | Leu | Arg | Gly | Tyr | Asp | Tyr | Gly | Pro | His | Phe | Gln | Gly |
|     |     |     | 995 |     |     |     |     | 1000 |     |     |     |     | 1005 |     |     |
| ATC | CTG | GAG | GCC | AGC | CTG | GAA | GGT | GAC | TCG | GGG | AGG | CTG | CTG | TGG | AAG | 3192 |
| Ile | Leu | Glu | Ala | Ser | Leu | Glu | Gly | Asp | Ser | Gly | Arg | Leu | Leu | Trp | Lys |
|     |     | 1010 |     |     |     |     | 1015 |     |     |     |     | 1020 |     |     |     |
| GAT | AAC | TGG | GTG | AGC | TTC | ATG | GAC | ACC | ATG | CTG | CAG | ATG | TCC | ATC | CTG | 3240 |
| Asp | Asn | Trp | Val | Ser | Phe | Met | Asp | Thr | Met | Leu | Gln | Met | Ser | Ile | Leu |
|     | 1025 |     |     |     |     | 1030 |     |     |     |     | 1035 |     |     |     |     |
| GGC | TCG | GCC | AAG | CAC | GGC | CTG | TAC | CTG | CCC | ACC | CGT | GTC | ACC | GCC | ATC | 3288 |
| Gly | Ser | Ala | Lys | His | Gly | Leu | Tyr | Leu | Pro | Thr | Arg | Val | Thr | Ala | Ile |
| 1040 |     |     |     | 1045 |     |     |     | 1050 |     |     |     |     | 1055 |     |     |
| CAC | ATC | GAC | CCT | GCC | ACC | CAC | AGG | CAG | AAG | CTG | TAC | ACA | CTG | CAG | GAC | 3336 |
| His | Ile | Asp | Pro | Ala | Thr | His | Arg | Gln | Lys | Leu | Tyr | Thr | Leu | Gln | Asp |
|     |     |     |     | 1060 |     |     |     |     | 1065 |     |     |     |     | 1070 |     |
| AAG | GCC | CAA | GTG | GCT | GAC | GTG | GTG | GTG | AGC | AGG | TGG | CTG | AGG | GTC | ACA | 3384 |
| Lys | Ala | Gln | Val | Ala | Asp | Val | Val | Val | Ser | Arg | Trp | Leu | Arg | Val | Thr |
|     |     |     | 1075 |     |     |     |     | 1080 |     |     |     |     | 1085 |     |     |
| GTG | GCC | GGA | GGC | GTC | CAC | ATC | TCC | GGG | CTC | CAC | ACT | GAG | TCG | GCC | CCG | 3432 |
| Val | Ala | Gly | Gly | Val | His | Ile | Ser | Gly | Leu | His | Thr | Glu | Ser | Ala | Pro |
|     |     | 1090 |     |     |     |     | 1095 |     |     |     |     | 1100 |     |     |     |
| CGG | CGG | CAG | CAG | GAG | CAG | CAG | GTG | CCC | ATC | CTG | GAG | AAG | TTT | TGC | TTC | 3480 |
| Arg | Arg | Gln | Gln | Glu | Gln | Gln | Val | Pro | Ile | Leu | Glu | Lys | Phe | Cys | Phe |
| 1105 |     |     |     |     | 1110 |     |     |     |     | 1115 |     |     |     |     |     |
| ACT | TCC | CAC | ACG | GAG | GAG | GGG | TGC | CTG | TCT | GAG | CGC | GCT | GCC | CTG | CAG | 3528 |
| Thr | Ser | His | Thr | Glu | Glu | Gly | Cys | Leu | Ser | Glu | Arg | Ala | Ala | Leu | Gln |
| 1120 |     |     |     | 1125 |     |     |     |     | 1130 |     |     |     |     | 1135 |     |
| GAG | GAG | CTG | CAA | CTG | TGC | AAG | GGG | CTG | GTG | CAG | GCA | CTG | CAG | ACC | AAG | 3576 |

```
                    Glu Glu Leu Gln Leu Cys Lys Gly Leu Val Gln Ala Leu Gln Thr Lys
                        1140                    1145                    1150

GTG ACC CAG CAG GGG CTG AAG ATG GTG GTG CCC GGA CTG GAT GGG GCC              3624
Val Thr Gln Gln Gly Leu Lys Met Val Val Pro Gly Leu Asp Gly Ala
        1155                    1160                    1165

CAG ATC CCC CGG GAC CCC TCA CAG CAG GAA CTG CCC CGG CTG TTG TCG              3672
Gln Ile Pro Arg Asp Pro Ser Gln Gln Glu Leu Pro Arg Leu Leu Ser
        1170                    1175                    1180

GCT GCC TGC AGG CTT CAG CTC AAC GGG AAC CTG CAG CTG GAG CTG GCG              3720
Ala Ala Cys Arg Leu Gln Leu Asn Gly Asn Leu Gln Leu Glu Leu Ala
        1185                    1190                    1195

CAG GTG CTG GCC CAG GAG AGG CCC AAG CTG CCA GAG GAC CCT CTG CTC              3768
Gln Val Leu Ala Gln Glu Arg Pro Lys Leu Pro Glu Asp Pro Leu Leu
1200                    1205                    1210                    1215

AGC GGC CTC CTG GAC TCC CCG GCA CTC AAG GCC TGC CTG GAC ACT GCC              3816
Ser Gly Leu Leu Asp Ser Pro Ala Leu Lys Ala Cys Leu Asp Thr Ala
        1220                    1225                    1230

GTG GAG AAC ATG CCC AGC CTG AAG ATG AAG GTG GTG GAG GTG CTG GCC              3864
Val Glu Asn Met Pro Ser Leu Lys Met Lys Val Val Glu Val Leu Ala
        1235                    1240                    1245

GGC CAC GGT CAC CTG TAT TCC CGC ATC CCA GGC CTG CTC AGC CCC CAT              3912
Gly His Gly His Leu Tyr Ser Arg Ile Pro Gly Leu Leu Ser Pro His
        1250                    1255                    1260

CCC CTG CTG CAG CTG AGC TAC ACG GCC ACC GAC CGC CAC CCC CAG GCC              3960
Pro Leu Leu Gln Leu Ser Tyr Thr Ala Thr Asp Arg His Pro Gln Ala
        1265                    1270                    1275

CTG GAG GCT GCC CAG GCC GAG CTG CAG CAG CAC GAC GTT GCC CAG GGC              4008
Leu Glu Ala Ala Gln Ala Glu Leu Gln Gln His Asp Val Ala Gln Gly
1280                    1285                    1290                    1295

CAG TGG GAT CCC GCA GAC CCT GCC CCC AGC GCC CTG GGC AGC GCC GAC              4056
Gln Trp Asp Pro Ala Asp Pro Ala Pro Ser Ala Leu Gly Ser Ala Asp
        1300                    1305                    1310

CTC CTG GTG TGC AAC TGT GCT GTG GCT GCC CTC GGG GAC CCG GCC TCA              4104
Leu Leu Val Cys Asn Cys Ala Val Ala Ala Leu Gly Asp Pro Ala Ser
        1315                    1320                    1325

GCT CTC AGC AAC ATG GTG GCT GCC CTG AGA GAA GGG GGC TTT CTG CTC              4152
Ala Leu Ser Asn Met Val Ala Ala Leu Arg Glu Gly Gly Phe Leu Leu
        1330                    1335                    1340

CTG CAC ACA CTG CTC CGG GGG CAC CCC TCG GGA CAT GTG GCC TTC CTC              4200
Leu His Thr Leu Leu Arg Gly His Pro Ser Gly His Val Ala Phe Leu
        1345                    1350                    1355

ACC TCC ACT GAG CCG CAG TAT GGC CAG GGC ATC CTG AGC CAG GAC GCG              4248
Thr Ser Thr Glu Pro Gln Tyr Gly Gln Gly Ile Leu Ser Gln Asp Ala
1360                    1365                    1370                    1375

TGG GAG AGC CTC TTC TCC AGG GTG TCC GTG CGC CTG GTG GGC CTG AAG              4296
Trp Glu Ser Leu Phe Ser Arg Val Ser Val Arg Leu Val Gly Leu Lys
        1380                    1385                    1390

AAG TCC TTC TAC GGC TCC ACG CTC TTC CTG TGC CGC CGG CCC ACC CCG              4344
Lys Ser Phe Tyr Gly Ser Thr Leu Phe Leu Cys Arg Arg Pro Thr Pro
        1395                    1400                    1405

CAG GAC AGC CCC ATC TTC CTG CCG GTG GAC GAT ACC AGC TTC CGC TGG              4392
Gln Asp Ser Pro Ile Phe Leu Pro Val Asp Asp Thr Ser Phe Arg Trp
        1410                    1415                    1420

GTG GAG TCT CTG AAG GGC ATC CTG GCT GAC GAA GAC TCT TCC CGG CCT              4440
Val Glu Ser Leu Lys Gly Ile Leu Ala Asp Glu Asp Ser Ser Arg Pro
        1425                    1430                    1435

GTG TGG CTG AAG GCC ATC AAC TGT GCC ACC TCG GGC GTG GTG GGC TTG              4488
Val Trp Leu Lys Ala Ile Asn Cys Ala Thr Ser Gly Val Val Gly Leu
1440                    1445                    1450                    1455

GTG AAC TGT CTC CGC CGA GAG CCC GGC GGA ACG CTC CGG TGT GTG CTG              4536
```

|  |  |  |  |  |  |  |  |  |  |  |  |  |  |  |  |
|---|---|---|---|---|---|---|---|---|---|---|---|---|---|---|---|
| Val | Asn | Cys | Leu | Arg | Arg | Glu | Pro | Gly | Gly | Thr | Leu | Arg | Cys | Val | Leu |
|  |  |  |  | 1460 |  |  |  | 1465 |  |  |  |  | 1470 |  |  |

```
CTC TCC AAC CTC AGC AGC ACC TCC CAC GTC CCG GAG GTG GAC CCG GGC    4584
Leu Ser Asn Leu Ser Ser Thr Ser His Val Pro Glu Val Asp Pro Gly
        1475                1480                    1485

TCC GCA GAA CTG CAG AAG GTG TTG CAG GGA GAC CTG GTG ATG AAC GTC    4632
Ser Ala Glu Leu Gln Lys Val Leu Gln Gly Asp Leu Val Met Asn Val
    1490                1495                1500

TAC CGC GAC GGG GCC TGG GGG GCT TTC CGC CAC TTC CTG CTG GAG GAG    4680
Tyr Arg Asp Gly Ala Trp Gly Ala Phe Arg His Phe Leu Leu Glu Glu
    1505                1510                1515

GAC AAG CCT GAG GAG CCG ACG GCA CAT GCC TTT GTG AGC ACC CTC ACC    4728
Asp Lys Pro Glu Glu Pro Thr Ala His Ala Phe Val Ser Thr Leu Thr
1520            1525                1530                    1535

CGG GGG GAC CTG TCC TCC ATC CGC TGG GTC TGC TCC TCG CTG CGC CAT    4776
Arg Gly Asp Leu Ser Ser Ile Arg Trp Val Cys Ser Ser Leu Arg His
            1540                1545                1550

GCC CAG CCC ACC TGC CCT GGC GCC CAG CTC TGC ACG GTC TAC TAC GCC    4824
Ala Gln Pro Thr Cys Pro Gly Ala Gln Leu Cys Thr Val Tyr Tyr Ala
            1555                1560                1565

TCC CTC AAC TTC CGC GAC ATC ATG CTG GCC ACT GGC AAG CTG TCC CCT    4872
Ser Leu Asn Phe Arg Asp Ile Met Leu Ala Thr Gly Lys Leu Ser Pro
        1570                1575                1580

GAT GCC ATC CCA GGG AAG TGG ACC TCC CAG GAC AGC CTG CTA GGT ATG    4920
Asp Ala Ile Pro Gly Lys Trp Thr Ser Gln Asp Ser Leu Leu Gly Met
    1585                1590                1595

GAG TTC TCG GGC CGA GAC GCC AGC GGC AAG CGT GTG ATG GGA CTG GTG    4968
Glu Phe Ser Gly Arg Asp Ala Ser Gly Lys Arg Val Met Gly Leu Val
1600            1605                1610                    1615

CCT GCC AAG GGC CTG GCC ACC TCT GTC CTG CTG TCA CCG GAC TTC CTC    5016
Pro Ala Lys Gly Leu Ala Thr Ser Val Leu Leu Ser Pro Asp Phe Leu
            1620                1625                1630

TGG GAT GTG CCT TCC AAC TGG ACG CTG GAG GAG GCG GCC TCG GTG CCT    5064
Trp Asp Val Pro Ser Asn Trp Thr Leu Glu Glu Ala Ala Ser Val Pro
            1635                1640                1645

GTC GTC TAC AGC ACG GCC TAC TAC GCG CTG GTG GTG CGT GGG CGG GTG    5112
Val Val Tyr Ser Thr Ala Tyr Tyr Ala Leu Val Val Arg Gly Arg Val
        1650                1655                1660

CGC CCC GGG GAG ACG CTG CTC ATC CAC TCG GGC TCG GGC GGC GTG GGC    5160
Arg Pro Gly Glu Thr Leu Leu Ile His Ser Gly Ser Gly Gly Val Gly
    1665                1670                1675

CAG GCC GCC ATC GCC ATC GCC CTC AGT CTG GGC TGC CGC GTC TTC ACC    5208
Gln Ala Ala Ile Ala Ile Ala Leu Ser Leu Gly Cys Arg Val Phe Thr
1680            1685                1690                    1695

ACC GTG GGG TCG GCT GAG AAG CGG GCG TAC CTC CAG GCC AGG TTC CCC    5256
Thr Val Gly Ser Ala Glu Lys Arg Ala Tyr Leu Gln Ala Arg Phe Pro
            1700                1705                1710

CAG CTC GAC AGC ACC AGC TTC GCC AAC TCC CGG GAC ACA TCC TTC GAG    5304
Gln Leu Asp Ser Thr Ser Phe Ala Asn Ser Arg Asp Thr Ser Phe Glu
            1715                1720                1725

CAG CAT GTG CTG TGG CAC ACG GGC GGG AAG GGC GTT GAC CTG GTC TTG    5352
Gln His Val Leu Trp His Thr Gly Gly Lys Gly Val Asp Leu Val Leu
            1730                1735                1740

AAC TCC TTG GCG GAA GAG AAG CTG CAG GCC AGC GTG AGG TGC TTG GCT    5400
Asn Ser Leu Ala Glu Glu Lys Leu Gln Ala Ser Val Arg Cys Leu Ala
        1745                1750                1755

ACG CAC GGT CGC TTC CTG GAA ATT GGC AAA TTC GAC CTT TCT CAG AAC    5448
Thr His Gly Arg Phe Leu Glu Ile Gly Lys Phe Asp Leu Ser Gln Asn
1760            1765                1770                    1775

CAC CCG CTC GGC ATG GCT ATC TTC CTG AAG AAC GTG ACA TTC CAC GGG    5496
```

-continued

| | | | | | | | | | | | | | | | | |
|---|---|---|---|---|---|---|---|---|---|---|---|---|---|---|---|---|
| His | Pro | Leu | Gly | Met | Ala | Ile | Phe | Leu | Lys | Asn | Val | Thr | Phe | His | Gly | |
| | | | | 1780 | | | | 1785 | | | | | 1790 | | | |

```
GTC CTA CTG GAT GCG TTC TTC AAC GAG AGC AGT GCT GAC TGG CGG GAG      5544
Val Leu Leu Asp Ala Phe Phe Asn Glu Ser Ser Ala Asp Trp Arg Glu
        1795                1800                1805

GTG TGG GCG CTT GTG CAG GCC GGC ATC CGG GAT GGG GTG GTA CGG CCC      5592
Val Trp Ala Leu Val Gln Ala Gly Ile Arg Asp Gly Val Val Arg Pro
    1810                1815                1820

CTC AAG TGC ACG GTG TTC CAT GGG GCC CAG GTG GAG GAC GCC TTC CGC      5640
Leu Lys Cys Thr Val Phe His Gly Ala Gln Val Glu Asp Ala Phe Arg
1825                1830                1835

TAC ATG GCC CAA GGG AAG CAC ATT GGC AAA GTC GTC GTG CAG GTG CTT      5688
Tyr Met Ala Gln Gly Lys His Ile Gly Lys Val Val Val Gln Val Leu
1840                1845                1850                1855

GCG GAG GAG CCG GAG GCA GTG CTG AAG GGG GCC AAA CCC AAG CTG ATG      5736
Ala Glu Glu Pro Glu Ala Val Leu Lys Gly Ala Lys Pro Lys Leu Met
        1860                1865                1870

TCG GCC ATC TCC AAG ACC TTC TGC CCG GCC CAC AAG AGC TAC ATC ATC      5784
Ser Ala Ile Ser Lys Thr Phe Cys Pro Ala His Lys Ser Tyr Ile Ile
            1875                1880                1885

GCT GGT GGT CTG GGT GGC TTC GGC CTG GAG TTG GCG CAG TGG CTG ATA      5832
Ala Gly Gly Leu Gly Gly Phe Gly Leu Glu Leu Ala Gln Trp Leu Ile
    1890                1895                1900

CAG CGT GGG GTG CAG AAG CTC GTG TTG ACT TCT CGC TCC GGG ATC CGG      5880
Gln Arg Gly Val Gln Lys Leu Val Leu Thr Ser Arg Ser Gly Ile Arg
1905                1910                1915

ACA GGC TAC CAG GCC AAG CAG GTC CGC CGG TGG AGG GCC CAG GGC GTA      5928
Thr Gly Tyr Gln Ala Lys Gln Val Arg Arg Trp Arg Ala Gln Gly Val
1920                1925                1930                1935

CAG GTG CAG GTG TCC ACC AGC AAC ATC AGC TCA CTG GAG GGG GCC CGG      5976
Gln Val Gln Val Ser Thr Ser Asn Ile Ser Ser Leu Glu Gly Ala Arg
        1940                1945                1950

GGC CTC ATT GCC GAG GCG GCG CAG CTT GGG CCC GTG GGC GGC GTC TTC      6024
Gly Leu Ile Ala Glu Ala Ala Gln Leu Gly Pro Val Gly Gly Val Phe
        1955                1960                1965

AAC CTG GCC GTG GTC TTG AGA GAT GGC TTG CTG GAG AAC CAG ACC CCA      6072
Asn Leu Ala Val Val Leu Arg Asp Gly Leu Leu Glu Asn Gln Thr Pro
    1970                1975                1980

GAG TTC TTC CAG GAC GTC TGC AAG CCC AAG TAC AGC GGC ACC CTG AAC      6120
Glu Phe Phe Gln Asp Val Cys Lys Pro Lys Tyr Ser Gly Thr Leu Asn
    1985                1990                1995

CTG GAC AGG GTG ACC CGA GAG GCG TGC CCT GAG CTG GAC TAC TTT GTG      6168
Leu Asp Arg Val Thr Arg Glu Ala Cys Pro Glu Leu Asp Tyr Phe Val
2000                2005                2010                2015

GTC TTC TCC TCT GTG AGC TGC GGG CGT GGC AAT GCG GGA CAG AGC AAC      6216
Val Phe Ser Ser Val Ser Cys Gly Arg Gly Asn Ala Gly Gln Ser Asn
            2020                2025                2030

TAC GGC TTT GCC AAT TCC GCC ATG GAG CGT ATC TGT GAG AAA CGC CGG      6264
Tyr Gly Phe Ala Asn Ser Ala Met Glu Arg Ile Cys Glu Lys Arg Arg
            2035                2040                2045

CAC GAA GGC CTC CCA GGC CTG GCC GTG CAG TGG GGC GCC ATC GGC GAC      6312
His Glu Gly Leu Pro Gly Leu Ala Val Gln Trp Gly Ala Ile Gly Asp
        2050                2055                2060

GTG GGC ATT TTG GTG GAG ACG ATG AGC ACC AAC GAC ACG ATC GTC AGT      6360
Val Gly Ile Leu Val Glu Thr Met Ser Thr Asn Asp Thr Ile Val Ser
    2065                2070                2075

GGC ACG CTG CCC CAG GCC ATG GCG TCC TGC CTG GAG GTG CTG GAC CTC      6408
Gly Thr Leu Pro Gln Ala Met Ala Ser Cys Leu Glu Val Leu Asp Leu
2080                2085                2090                2095

TTC CTG AAC CAG CCC CAC ATG GTC CTG AGC AGC TTT GTG CTG GCT GAG      6456
```

```
                Phe  Leu  Asn  Gln  Pro  His  Met  Val  Leu  Ser  Ser  Phe  Val  Leu  Ala  Glu
                               2100                     2105                     2110

AAG  GCT  GCG  GCC  TAT  AGG  GAC  AGG  GAC  AGC  CAG  CGG  GAC  CTG  GTG  GAG                 6504
Lys  Ala  Ala  Ala  Tyr  Arg  Asp  Arg  Asp  Ser  Gln  Arg  Asp  Leu  Val  Glu
               2115                     2120                     2125

GCC  GTG  GCA  CAC  ATC  CTG  GGC  ATC  CGC  GAC  TTG  GCT  GCT  GTC  AAC  CTG                 6552
Ala  Val  Ala  His  Ile  Leu  Gly  Ile  Arg  Asp  Leu  Ala  Ala  Val  Asn  Leu
               2130                     2135                     2140

GAC  AGC  TCA  CTG  GCG  GAC  CTG  GGC  CTG  GAC  TCG  CTC  ATG  AGC  GTG  GAG                 6600
Asp  Ser  Ser  Leu  Ala  Asp  Leu  Gly  Leu  Asp  Ser  Leu  Met  Ser  Val  Glu
          2145                     2150                     2155

GTG  CGC  CAG  ACG  CTG  GAG  CGT  GAG  CTC  AAC  CTG  GTG  CTG  TCC  GTG  CGC                 6648
Val  Arg  Gln  Thr  Leu  Glu  Arg  Glu  Leu  Asn  Leu  Val  Leu  Ser  Val  Arg
2160                     2165                     2170                     2175

GAG  GTG  CGG  CAA  CTC  ACG  CTC  CGG  AAA  CTG  CAG  GAG  CTG  TCC  TCA  AAG                 6696
Glu  Val  Arg  Gln  Leu  Thr  Leu  Arg  Lys  Leu  Gln  Glu  Leu  Ser  Ser  Lys
                              2180                     2185                     2190

GCG  GAT  GAG  GCC  AGC  GAG  CTG  GCA  TGC  CCC  ACG  CCC  AAG  GAG  GAT  GGT                 6744
Ala  Asp  Glu  Ala  Ser  Glu  Leu  Ala  Cys  Pro  Thr  Pro  Lys  Glu  Asp  Gly
               2195                     2200                     2205

CTG  GCC  CAG  CAG  CAG  ACT  CAG  CTG  AAC  CTG  CGC  TCC  CTG  CTG  GTG  AAC                 6792
Leu  Ala  Gln  Gln  Gln  Thr  Gln  Leu  Asn  Leu  Arg  Ser  Leu  Leu  Val  Asn
               2210                     2215                     2220

CCG  GAG  GGC  CCC  ACC  CTG  ATG  CGG  CTC  AAC  TCC  GTG  CAG  AGC  TCG  GAG                 6840
Pro  Glu  Gly  Pro  Thr  Leu  Met  Arg  Leu  Asn  Ser  Val  Gln  Ser  Ser  Glu
     2225                     2230                     2235

CGG  CCC  CTG  TTC  CTG  GTG  CAC  CCA  ATC  GAG  GGC  TCC  ACC  ACC  GTG  TTC                 6888
Arg  Pro  Leu  Phe  Leu  Val  His  Pro  Ile  Glu  Gly  Ser  Thr  Thr  Val  Phe
2240                     2245                     2250                     2255

CAC  AGC  CTG  GCC  TCC  CGG  CTC  AGC  ATC  CCC  ACC  TAT  GGC  CTG  CAG  TGC                 6936
His  Ser  Leu  Ala  Ser  Arg  Leu  Ser  Ile  Pro  Thr  Tyr  Gly  Leu  Gln  Cys
                              2260                     2265                     2270

ACC  CGA  GCT  GCG  CCC  CTT  GAC  AGC  ATC  CAC  AGC  CTG  GCT  GCC  TAC  TAC                 6984
Thr  Arg  Ala  Ala  Pro  Leu  Asp  Ser  Ile  His  Ser  Leu  Ala  Ala  Tyr  Tyr
                         2275                     2280                     2285

ATC  GAC  TGC  ATC  AGG  CAG  GTG  CAG  CCC  GAG  GGC  CCC  TAC  CGC  GTG  GCC                 7032
Ile  Asp  Cys  Ile  Arg  Gln  Val  Gln  Pro  Glu  Gly  Pro  Tyr  Arg  Val  Ala
               2290                     2295                     2300

GGC  TAC  TCC  TAC  GGG  GCC  TGC  GTG  GCC  TTT  GAA  ATG  TGC  TCC  CAG  CTG                 7080
Gly  Tyr  Ser  Tyr  Gly  Ala  Cys  Val  Ala  Phe  Glu  Met  Cys  Ser  Gln  Leu
     2305                     2310                     2315

CAG  GCC  CAG  CAG  AGC  CCA  GCC  CCC  ACC  CAC  AAC  AGC  CTC  TTC  CTG  TTC                 7128
Gln  Ala  Gln  Gln  Ser  Pro  Ala  Pro  Thr  His  Asn  Ser  Leu  Phe  Leu  Phe
2320                     2325                     2330                     2335

GAC  GGC  TCG  CCC  ACC  TAC  GTA  CTG  GCC  TAC  ACC  CAG  AGC  TAC  CGG  GCA                 7176
Asp  Gly  Ser  Pro  Thr  Tyr  Val  Leu  Ala  Tyr  Thr  Gln  Ser  Tyr  Arg  Ala
                         2340                     2345                     2350

AAG  CTG  ACC  CCA  GGC  TGT  GAG  GCT  GAG  GCT  GAG  ACG  GAG  GCC  ATA  TGC                 7224
Lys  Leu  Thr  Pro  Gly  Cys  Glu  Ala  Glu  Ala  Glu  Thr  Glu  Ala  Ile  Cys
               2355                     2360                     2365

TTC  TTC  GTG  CAG  CAG  TTC  ACG  GAC  ATG  GAG  CAC  AAC  AGG  GTG  CTG  GAG                 7272
Phe  Phe  Val  Gln  Gln  Phe  Thr  Asp  Met  Glu  His  Asn  Arg  Val  Leu  Glu
          2370                     2375                     2380

GCG  CTG  CTG  CCG  CTG  AAG  GGC  CTA  GAG  GAG  CGT  GTG  GCA  GCC  GCC  GTG                 7320
Ala  Leu  Leu  Pro  Leu  Lys  Gly  Leu  Glu  Glu  Arg  Val  Ala  Ala  Ala  Val
     2385                     2390                     2395

GAC  CTG  ATC  ATC  AAG  AGC  CAC  CAG  GGC  CTG  GAC  CGC  CAG  GAG  CTG  AGC                 7368
Asp  Leu  Ile  Ile  Lys  Ser  His  Gln  Gly  Leu  Asp  Arg  Gln  Glu  Leu  Ser
2400                     2405                     2410                     2415

TTT  GCG  GCC  CGG  TCC  TTC  TAC  TAC  AAG  CTC  GGT  GCC  GCT  GAG  CAG  TAC                 7416
```

| | | | | | | | | | | | | | | |
|---|---|---|---|---|---|---|---|---|---|---|---|---|---|---|
|Phe|Ala|Ala|Arg|Ser|Phe|Tyr|Tyr|Lys|Leu|Gly|Ala|Ala|Glu|Gln|Tyr|
| | | |2420| | | |2425| | | | |2430| | |

```
ACA CCC AAG GCC AAG TAC CAT GGC AAC GTG ATG CTA CTG CGC GCC AAG       7464
Thr Pro Lys Ala Lys Tyr His Gly Asn Val Met Leu Leu Arg Ala Lys
        2435                2440                2445

ACG GGT GGC GCC TAC GGC GAG GAC CTG GGC GCG GAT TAC AAC CTC TCC       7512
Thr Gly Gly Ala Tyr Gly Glu Asp Leu Gly Ala Asp Tyr Asn Leu Ser
        2450                2455                2460

CAG GTA TGC GAC GGG AAA GTA TCC GTC CAC GTC ATC GAG GGT GAC CAC       7560
Gln Val Cys Asp Gly Lys Val Ser Val His Val Ile Glu Gly Asp His
        2465                2470                2475

CGC ACG CTG CTG GAG GGC AGC GGC CTG GAG TCC ATC ATC AGC ATC ATC       7608
Arg Thr Leu Leu Glu Gly Ser Gly Leu Glu Ser Ile Ile Ser Ile Ile
2480                2485                2490                2495

CAC AGC TCC CTG GCT GAG CCA CGC GTG AGC GTG CGG GAG GGC TAGGCCGTG     7660
His Ser Ser Leu Ala Glu Pro Arg Val Ser Val Arg Glu Gly
        2500                2505                2

CCCCGCCTG  CCACCGGAGG  TCACTCCACC  ATCCCCACCC  CACCCCACCC  CACCCCGCC    7720
ATGCAACGGG  ATTGAAGGGT  CCTGCCGGTG  GGACCCTGTC  CGGCCCAGTG  CCACTGCCCC   7780
CCGAGGCTGC  TAGATGTAGG  TGTTAGGCAT  GTCCCACCCA  CCCGCCGCCT  CCCACGGCAC   7840
CTCGGGGACA  CCAGAGCTGC  CGACTTGGAG  ACTCCTGGTC  TGTGAAGAGC  CGGTGGTGCC   7900
CGTTCCCGCA  GGAACTGGGC  TGGGCCTCGT  GCGCCCGTGG  GGTCTGCGCT  TGGTCTTTCT   7960
GTGCTTGGAT  TTGCATATTT  ATTGCATTGC  TGGTAGAGAC  CCCCAGGCCT  GTCCACCCTG   8020
CCAAGACTCC  TCAGGCAGCG  TGTGGGTCCC  GCACTCTGCC  CCCATTTCCC  CGATGTCCCC   8080
TGCGGGCGCG  GGCAGCCACC  CAAGCCTGCT  GGCTGCGGCC  CCCTCTCGGC  CAGGCATTGG   8140
CTCAGCCNGC  TGAGTGGGGG  GTCGTGGGCC  AGTCCCCGAG  GAGCTGGGCC  CCTGCACAGG   8200
CACACAGGGC  CCGGCCACAC  CCAGCGGCCC  CCCGCACAGC  CACCCGTGGG  GTGCTGCCCT   8260
TATCGCCCGG  CGCCGGGCAC  CAACTCCATG  TTTGGTGTTT  GTCTGTGTTT  GTTTTCAAG    8320
AAATGATTCA  AATTGCTGCT  TGGATTTTGA  AATTTACTGT  AACTGTCAGT  GTACACGTCT   8380
GGACCCCGTT  TCATTTTTAC  ACCAATTTGG  TAAAAATGCT  GCTCTCAGCC  TCCCACAATT   8440
AAACCGCATG  TGATCTCCCC                                                   8460
```

( 2 ) INFORMATION FOR SEQ ID NO:10:

( i ) SEQUENCE CHARACTERISTICS:
        ( A ) LENGTH: 2509 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:10:

```
Met Glu Glu Val Val Ile Ala Gly Met Ser Gly Lys Leu Pro Glu Ser
 1               5                  10                  15

Glu Asn Leu Gln Glu Phe Trp Asp Asn Leu Ile Gly Gly Val Asp Met
                20                  25                  30

Val Thr Asp Asp Asp Arg Arg Trp Lys Ala Gly Leu Tyr Gly Leu Pro
            35                  40                  45
```

-continued

```
Arg  Arg  Ser  Gly  Lys  Leu  Lys  Asp  Leu  Ser  Arg  Phe  Asp  Ala  Ser  Phe
     50             55                       60

Phe  Gly  Val  His  Pro  Lys  Gln  Ala  His  Thr  Met  Asp  Pro  Gln  Leu  Arg
65             70                       75                            80

Leu  Leu  Leu  Glu  Val  Thr  Tyr  Glu  Ala  Ile  Val  Asp  Gly  Gly  Ile  Asn
               85                  90                            95

Pro  Asp  Ser  Leu  Arg  Gly  Thr  His  Thr  Gly  Val  Trp  Val  Gly  Val  Ser
               100                 105                 110

Gly  Ser  Glu  Thr  Ser  Glu  Ala  Leu  Ser  Arg  Asp  Pro  Glu  Thr  Leu  Val
          115                 120                      125

Gly  Tyr  Ser  Met  Val  Gly  Cys  Gln  Arg  Ala  Met  Met  Ala  Asn  Arg  Leu
     130                 135                 140

Ser  Phe  Phe  Phe  Asp  Phe  Arg  Gly  Pro  Ser  Ile  Ala  Leu  Asp  Thr  Ala
145                      150                 155                           160

Cys  Ser  Ser  Ser  Leu  Met  Ala  Leu  Gln  Asn  Ala  Tyr  Gln  Ala  Ile  His
                    165                 170                      175

Ser  Gly  Gln  Cys  Pro  Ala  Ala  Ile  Val  Gly  Gly  Ile  Asn  Val  Leu  Leu
               180                 185                      190

Lys  Pro  Asn  Thr  Ser  Val  Gln  Phe  Leu  Arg  Leu  Gly  Met  Leu  Ser  Pro
          195                 200                      205

Glu  Gly  Thr  Cys  Lys  Ala  Phe  Asp  Thr  Ala  Gly  Asn  Gly  Tyr  Cys  Arg
210                      215                 220

Ser  Glu  Gly  Val  Val  Ala  Val  Leu  Leu  Thr  Lys  Lys  Ser  Leu  Ala  Arg
225                 230                 235                           240

Arg  Val  Tyr  Ala  Thr  Ile  Leu  Asn  Ala  Gly  Thr  Asn  Thr  Asp  Gly  Phe
               245                 250                      255

Lys  Glu  Gln  Gly  Val  Thr  Phe  Pro  Ser  Gly  Asp  Ile  Gln  Glu  Gln  Leu
          260                 265                      270

Ile  Arg  Ser  Leu  Tyr  Gln  Ser  Ala  Gly  Val  Ala  Pro  Glu  Ser  Phe  Glu
          275                 280                      285

Tyr  Ile  Glu  Ala  His  Gly  Thr  Gly  Thr  Lys  Val  Gly  Asp  Pro  Gln  Glu
290                      295                 300

Leu  Asn  Gly  Ile  Thr  Arg  Ala  Leu  Cys  Ala  Thr  Arg  Gln  Glu  Pro  Leu
305                 310                 315                           320

Leu  Ile  Gly  Ser  Thr  Lys  Ser  Asn  Met  Gly  His  Pro  Glu  Pro  Ala  Ser
               325                 330                      335

Gly  Leu  Ala  Ala  Leu  Ala  Lys  Val  Leu  Leu  Ser  Leu  Glu  His  Gly  Leu
          340                 345                      350

Trp  Ala  Pro  Asn  Leu  His  Phe  His  Ser  Pro  Asn  Pro  Glu  Ile  Pro  Ala
          355                 360                      365

Leu  Leu  Asp  Gly  Arg  Leu  Gln  Val  Val  Asp  Gln  Pro  Leu  Pro  Val  Arg
370                      375                 380

Gly  Gly  Asn  Val  Gly  Ile  Asn  Ser  Phe  Gly  Phe  Gly  Gly  Ser  Asn  Val
385                 390                 395                           400

His  Ile  Ile  Leu  Arg  Pro  Asn  Thr  Gln  Pro  Pro  Ala  Pro  Ala  Pro
                    405                 410                      415

His  Ala  Thr  Leu  Pro  Arg  Leu  Leu  Arg  Ala  Ser  Gly  Arg  Thr  Pro  Glu
               420                 425                      430

Ala  Val  Gln  Lys  Leu  Leu  Glu  Gln  Gly  Leu  Arg  His  Ser  Gln  Asp  Leu
          435                 440                      445

Ala  Phe  Leu  Ser  Met  Leu  Asn  Asp  Ile  Ala  Leu  Ser  Pro  Thr  Thr  Ala
450                      455                 460

Met  Pro  Phe  Arg  Gly  Tyr  Ala  Val  Leu  Gly  Gly  Glu  Arg  Gly  Gly  Pro
```

-continued

```
465                       470                       475                       480
Glu  Val  Gln  Gln  Val  Pro  Ala  Gly  Glu  Arg  Pro  Leu  Trp  Phe  Ile  Cys
                    485                      490                      495

Ser  Gly  Met  Gly  Thr  Gln  Trp  Arg  Gly  Met  Gly  Leu  Ser  Leu  Met  Arg
                    500                      505                      510

Leu  Asp  Arg  Phe  Arg  Asp  Ser  Ile  Leu  Arg  Ser  Asp  Glu  Ala  Val  Asn
               515                      520                      525

Arg  Phe  Gly  Leu  Lys  Val  Ser  Gln  Leu  Leu  Leu  Ser  Thr  Asp  Glu  Ser
          530                      535                      540

Thr  Phe  Asp  Asp  Ile  Val  His  Ser  Phe  Val  Ser  Leu  Thr  Ala  Ile  Gln
545                      550                      555                      560

Ile  Gly  Leu  Ile  Asp  Leu  Leu  Ser  Cys  Met  Gly  Leu  Arg  Pro  Asp  Gly
                    565                      570                      575

Ile  Val  Gly  His  Ser  Leu  Gly  Glu  Val  Ala  Cys  Gly  Tyr  Ala  Asp  Gly
                    580                      585                      590

Cys  Leu  Ser  Gln  Glu  Glu  Ala  Val  Leu  Ala  Ala  Tyr  Trp  Arg  Gly  Gln
               595                      600                      605

Cys  Ile  Lys  Glu  Ala  His  Leu  Pro  Pro  Gly  Ala  Met  Ala  Ala  Val  Gly
          610                      615                      620

Leu  Ser  Trp  Glu  Glu  Cys  Lys  Gln  Arg  Cys  Pro  Ala  Val  Val  Pro
625                      630                      635                      640

Ala  Cys  His  Asn  Ser  Lys  Asp  Thr  Val  Thr  Ile  Ser  Gly  Pro  Gln  Ala
                    645                      650                      655

Pro  Val  Phe  Glu  Phe  Val  Glu  Gln  Leu  Arg  Lys  Glu  Gly  Val  Phe  Ala
                    660                      665                      670

Lys  Glu  Val  Arg  Thr  Gly  Gly  Met  Ala  Phe  His  Ser  Tyr  Phe  Met  Glu
               675                      680                      685

Ala  Ile  Ala  Pro  Pro  Leu  Leu  Gln  Glu  Leu  Lys  Lys  Val  Ile  Arg  Glu
          690                      695                      700

Pro  Lys  Pro  Arg  Ser  Ala  Arg  Trp  Leu  Ser  Thr  Ser  Ile  Pro  Glu  Ala
705                      710                      715                      720

Gln  Trp  His  Ser  Ser  Leu  Ala  Arg  Thr  Ser  Ser  Ala  Glu  Tyr  Asn  Val
                    725                      730                      735

Asn  Asn  Leu  Val  Ser  Pro  Val  Leu  Phe  Gln  Glu  Ala  Leu  Trp  His  Val
                    740                      745                      750

Pro  Glu  His  Ala  Val  Val  Leu  Glu  Ile  Ala  Pro  His  Ala  Leu  Leu  Gln
               755                      760                      765

Ala  Val  Leu  Lys  Arg  Gly  Leu  Lys  Pro  Ser  Cys  Thr  Ile  Ile  Pro  Leu
          770                      775                      780

Met  Lys  Lys  Asp  His  Arg  Asp  Asn  Leu  Glu  Phe  Phe  Leu  Ala  Gly  Ile
785                      790                      795                      800

Arg  Arg  Leu  His  Leu  Ser  Gly  Ile  Asp  Ala  Asn  Pro  Asn  Ala  Leu  Phe
                    805                      810                      815

Pro  Pro  Val  Glu  Phe  Pro  Ala  Pro  Arg  Gly  Thr  Pro  Leu  Ile  Ser  Pro
                    820                      825                      830

Leu  Ile  Lys  Trp  Asp  His  Ser  Leu  Ala  Trp  Asp  Val  Pro  Ala  Ala  Glu
               835                      840                      845

Asp  Phe  Pro  Asn  Gly  Ser  Gly  Ser  Pro  Ser  Ala  Ala  Ile  Tyr  Asn  Ile
          850                      855                      860

Asp  Thr  Ser  Ser  Glu  Ser  Pro  Asp  His  Tyr  Leu  Val  Asp  His  Thr  Leu
865                      870                      875                      880

Asp  Gly  Arg  Val  Leu  Phe  Pro  Ala  Thr  Gly  Tyr  Leu  Ser  Ile  Val  Trp
                    885                      890                      895
```

```
Lys  Thr  Leu  Ala  Arg  Pro  Leu  Gly  Leu  Gly  Val  Glu  Gln  Leu  Pro  Val
               900                 905                 910

Val  Phe  Glu  Asp  Val  Val  Leu  His  Gln  Ala  Thr  Ile  Leu  Pro  Lys  Thr
               915                 920                 925

Gly  Thr  Val  Ser  Leu  Glu  Val  Arg  Leu  Leu  Glu  Ala  Ser  Arg  Ala  Phe
               930                 935                 940

Glu  Val  Ser  Glu  Asn  Gly  Asn  Leu  Val  Val  Ser  Gly  Lys  Val  Tyr  Gln
945                      950                 955                           960

Trp  Asp  Asp  Pro  Asp  Pro  Arg  Leu  Phe  Asp  His  Pro  Glu  Ser  Pro  Thr
                    965                 970                 975

Pro  Asn  Pro  Thr  Glu  Pro  Leu  Phe  Leu  Ala  Gln  Ala  Glu  Val  Tyr  Lys
               980                 985                 990

Glu  Leu  Arg  Leu  Arg  Gly  Tyr  Asp  Tyr  Gly  Pro  His  Phe  Gln  Gly  Ile
               995                1000                1005

Leu  Glu  Ala  Ser  Leu  Glu  Gly  Asp  Ser  Gly  Arg  Leu  Leu  Trp  Lys  Asp
          1010                1015                1020

Asn  Trp  Val  Ser  Phe  Met  Asp  Thr  Met  Leu  Gln  Met  Ser  Ile  Leu  Gly
025                      1030                1035                     1040

Ser  Ala  Lys  His  Gly  Leu  Tyr  Leu  Pro  Thr  Arg  Val  Thr  Ala  Ile  His
               1045                1050                     1055

Ile  Asp  Pro  Ala  Thr  His  Arg  Gln  Lys  Leu  Tyr  Thr  Leu  Gln  Asp  Lys
               1060                1065                1070

Ala  Gln  Val  Ala  Asp  Val  Val  Val  Ser  Arg  Trp  Leu  Arg  Val  Thr  Val
          1075                1080                1085

Ala  Gly  Gly  Val  His  Ile  Ser  Gly  Leu  His  Thr  Glu  Ser  Ala  Pro  Arg
     1090                1095                1100

Arg  Gln  Gln  Glu  Gln  Gln  Val  Pro  Ile  Leu  Glu  Lys  Phe  Cys  Phe  Thr
105                 1110                1115                1120

Ser  His  Thr  Glu  Glu  Gly  Cys  Leu  Ser  Glu  Arg  Ala  Ala  Leu  Gln  Glu
               1125                1130                1135

Glu  Leu  Gln  Leu  Cys  Lys  Gly  Leu  Val  Gln  Ala  Leu  Gln  Thr  Lys  Val
               1140                1145                1150

Thr  Gln  Gln  Gly  Leu  Lys  Met  Val  Val  Pro  Gly  Leu  Asp  Gly  Ala  Gln
          1155                1160                1165

Ile  Pro  Arg  Asp  Pro  Ser  Gln  Gln  Glu  Leu  Pro  Arg  Leu  Leu  Ser  Ala
     1170                1175                1180

Ala  Cys  Arg  Leu  Gln  Leu  Asn  Gly  Asn  Leu  Gln  Leu  Glu  Leu  Ala  Gln
185                      1190                1195                     1200

Val  Leu  Ala  Gln  Glu  Arg  Pro  Lys  Leu  Pro  Glu  Asp  Pro  Leu  Leu  Ser
               1205                1210                1215

Gly  Leu  Leu  Asp  Ser  Pro  Ala  Leu  Lys  Ala  Cys  Leu  Asp  Thr  Ala  Val
               1220                1225                1230

Glu  Asn  Met  Pro  Ser  Leu  Lys  Met  Lys  Val  Val  Glu  Val  Leu  Ala  Gly
               1235                1240                1245

His  Gly  His  Leu  Tyr  Ser  Arg  Ile  Pro  Gly  Leu  Leu  Ser  Pro  His  Pro
     1250                1255                1260

Leu  Leu  Gln  Leu  Ser  Tyr  Thr  Ala  Thr  Asp  Arg  His  Pro  Gln  Ala  Leu
265                      1270                1275                     1280

Glu  Ala  Ala  Gln  Ala  Glu  Leu  Gln  Gln  His  Asp  Val  Ala  Gln  Gly  Gln
               1285                1290                1295

Trp  Asp  Pro  Ala  Asp  Pro  Ala  Pro  Ser  Ala  Leu  Gly  Ser  Ala  Asp  Leu
               1300                1305                1310

Leu  Val  Cys  Asn  Cys  Ala  Val  Ala  Ala  Leu  Gly  Asp  Pro  Ala  Ser  Ala
     1315                1320                1325
```

```
Leu  Ser  Asn  Met  Val  Ala  Ala  Leu  Arg  Glu  Gly  Gly  Phe  Leu  Leu  Leu
         1330                    1335                    1340

His  Thr  Leu  Leu  Arg  Gly  His  Pro  Ser  Gly  His  Val  Ala  Phe  Leu  Thr
345                      1350                    1355                    1360

Ser  Thr  Glu  Pro  Gln  Tyr  Gly  Gln  Gly  Ile  Leu  Ser  Gln  Asp  Ala  Trp
              1365                    1370                    1375

Glu  Ser  Leu  Phe  Ser  Arg  Val  Ser  Val  Arg  Leu  Val  Gly  Leu  Lys  Lys
         1380                    1385                    1390

Ser  Phe  Tyr  Gly  Ser  Thr  Leu  Phe  Leu  Cys  Arg  Arg  Pro  Thr  Pro  Gln
         1395                    1400                    1405

Asp  Ser  Pro  Ile  Phe  Leu  Pro  Val  Asp  Asp  Thr  Ser  Phe  Arg  Trp  Val
         1410                    1415                    1420

Glu  Ser  Leu  Lys  Gly  Ile  Leu  Ala  Asp  Glu  Asp  Ser  Ser  Arg  Pro  Val
425                      1430                    1435                    1440

Trp  Leu  Lys  Ala  Ile  Asn  Cys  Ala  Thr  Ser  Gly  Val  Val  Gly  Leu  Val
                   1445                    1450                    1455

Asn  Cys  Leu  Arg  Arg  Glu  Pro  Gly  Gly  Thr  Leu  Arg  Cys  Val  Leu  Leu
         1460                    1465                    1470

Ser  Asn  Leu  Ser  Ser  Thr  Ser  His  Val  Pro  Glu  Val  Asp  Pro  Gly  Ser
         1475                    1480                    1485

Ala  Glu  Leu  Gln  Lys  Val  Leu  Gln  Gly  Asp  Leu  Val  Met  Asn  Val  Tyr
         1490                    1495                    1500

Arg  Asp  Gly  Ala  Trp  Gly  Ala  Phe  Arg  His  Phe  Leu  Leu  Glu  Glu  Asp
505                      1510                    1515                    1520

Lys  Pro  Glu  Glu  Pro  Thr  Ala  His  Ala  Phe  Val  Ser  Thr  Leu  Thr  Arg
              1525                    1530                    1535

Gly  Asp  Leu  Ser  Ser  Ile  Arg  Trp  Val  Cys  Ser  Ser  Leu  Arg  His  Ala
         1540                    1545                    1550

Gln  Pro  Thr  Cys  Pro  Gly  Ala  Gln  Leu  Cys  Thr  Val  Tyr  Tyr  Ala  Ser
         1555                    1560                    1565

Leu  Asn  Phe  Arg  Asp  Ile  Met  Leu  Ala  Thr  Gly  Lys  Leu  Ser  Pro  Asp
         1570                    1575                    1580

Ala  Ile  Pro  Gly  Lys  Trp  Thr  Ser  Gln  Asp  Ser  Leu  Leu  Gly  Met  Glu
585                      1590                    1595                    1600

Phe  Ser  Gly  Arg  Asp  Ala  Ser  Gly  Lys  Arg  Val  Met  Gly  Leu  Val  Pro
              1605                    1610                    1615

Ala  Lys  Gly  Leu  Ala  Thr  Ser  Val  Leu  Leu  Ser  Pro  Asp  Phe  Leu  Trp
              1620                    1625                    1630

Asp  Val  Pro  Ser  Asn  Trp  Thr  Leu  Glu  Glu  Ala  Ala  Ser  Val  Pro  Val
         1635                    1640                    1645

Val  Tyr  Ser  Thr  Ala  Tyr  Tyr  Ala  Leu  Val  Val  Arg  Gly  Arg  Val  Arg
         1650                    1655                    1660

Pro  Gly  Glu  Thr  Leu  Leu  Ile  His  Ser  Gly  Ser  Gly  Gly  Val  Gly  Gln
665                      1670                    1675                    1680

Ala  Ala  Ile  Ala  Ile  Ala  Leu  Ser  Leu  Gly  Cys  Arg  Val  Phe  Thr  Thr
                   1685                    1690                    1695

Val  Gly  Ser  Ala  Glu  Lys  Arg  Ala  Tyr  Leu  Gln  Ala  Arg  Phe  Pro  Gln
              1700                    1705                    1710

Leu  Asp  Ser  Thr  Ser  Phe  Ala  Asn  Ser  Arg  Asp  Thr  Ser  Phe  Glu  Gln
         1715                    1720                    1725

His  Val  Leu  Trp  His  Thr  Gly  Gly  Lys  Gly  Val  Asp  Leu  Val  Leu  Asn
         1730                    1735                    1740

Ser  Leu  Ala  Glu  Glu  Lys  Leu  Gln  Ala  Ser  Val  Arg  Cys  Leu  Ala  Thr
```

|     | 1745 | 1750 | 1755 | 1760 |

His Gly Arg Phe Leu Glu Ile Gly Lys Phe Asp Leu Ser Gln Asn His
                1765                1770                1775

Pro Leu Gly Met Ala Ile Phe Leu Lys Asn Val Thr Phe His Gly Val
                1780                1785                1790

Leu Leu Asp Ala Phe Phe Asn Ser Ser Ala Asp Trp Arg Glu Val
            1795                1800                1805

Trp Ala Leu Val Gln Ala Gly Ile Arg Asp Gly Val Val Arg Pro Leu
    1810                1815                1820

Lys Cys Thr Val Phe His Gly Ala Gln Val Glu Asp Ala Phe Arg Tyr
1825                1830                1835                1840

Met Ala Gln Gly Lys His Ile Gly Lys Val Val Gln Val Leu Ala
                1845                1850                1855

Glu Glu Pro Glu Ala Val Leu Lys Gly Ala Lys Pro Lys Leu Met Ser
            1860                1865                1870

Ala Ile Ser Lys Thr Phe Cys Pro Ala His Lys Ser Tyr Ile Ile Ala
            1875                1880                1885

Gly Gly Leu Gly Gly Phe Gly Leu Glu Leu Ala Gln Trp Leu Ile Gln
    1890                1895                1900

Arg Gly Val Gln Lys Leu Val Leu Thr Ser Arg Ser Gly Ile Arg Thr
1905                1910                1915                1920

Gly Tyr Gln Ala Lys Gln Val Arg Arg Trp Arg Ala Gln Gly Val Gln
                1925                1930                1935

Val Gln Val Ser Thr Ser Asn Ile Ser Ser Leu Glu Gly Ala Arg Gly
            1940                1945                1950

Leu Ile Ala Glu Ala Ala Gln Leu Gly Pro Val Gly Gly Val Phe Asn
            1955                1960                1965

Leu Ala Val Val Leu Arg Asp Gly Leu Leu Glu Asn Gln Thr Pro Glu
1970                1975                1980

Phe Phe Gln Asp Val Cys Lys Pro Lys Tyr Ser Gly Thr Leu Asn Leu
1985                1990                1995                2000

Asp Arg Val Thr Arg Glu Ala Cys Pro Glu Leu Asp Tyr Phe Val Val
            2005                2010                2015

Phe Ser Ser Val Ser Cys Gly Arg Gly Asn Ala Gly Gln Ser Asn Tyr
            2020                2025                2030

Gly Phe Ala Asn Ser Ala Met Glu Arg Ile Cys Glu Lys Arg Arg His
    2035                2040                2045

Glu Gly Leu Pro Gly Leu Ala Val Gln Trp Gly Ala Ile Gly Asp Val
2050                2055                2060

Gly Ile Leu Val Glu Thr Met Ser Thr Asn Asp Thr Ile Val Ser Gly
2065                2070                2075                2080

Thr Leu Pro Gln Ala Met Ala Ser Cys Leu Glu Val Leu Asp Leu Phe
                2085                2090                2095

Leu Asn Gln Pro His Met Val Leu Ser Ser Phe Val Leu Ala Glu Lys
                2100                2105                2110

Ala Ala Ala Tyr Arg Asp Arg Asp Ser Gln Arg Asp Leu Val Glu Ala
            2115                2120                2125

Val Ala His Ile Leu Gly Ile Arg Asp Leu Ala Ala Val Asn Leu Asp
    2130                2135                2140

Ser Ser Leu Ala Asp Leu Gly Leu Asp Ser Leu Met Ser Val Glu Val
2145                2150                2155                2160

Arg Gln Thr Leu Glu Arg Glu Leu Asn Leu Val Leu Ser Val Arg Glu
                2165                2170                2175

```
Val  Arg  Gln  Leu  Thr  Leu  Arg  Lys  Leu  Gln  Glu  Leu  Ser  Ser  Lys  Ala
          2180                2185                          2190

Asp  Glu  Ala  Ser  Glu  Leu  Ala  Cys  Pro  Thr  Pro  Lys  Glu  Asp  Gly  Leu
          2195                2200                          2205

Ala  Gln  Gln  Gln  Thr  Gln  Leu  Asn  Leu  Arg  Ser  Leu  Leu  Val  Asn  Pro
          2210                2215                          2220

Glu  Gly  Pro  Thr  Leu  Met  Arg  Leu  Asn  Ser  Val  Gln  Ser  Ser  Glu  Arg
225                      2230                2235                          2240

Pro  Leu  Phe  Leu  Val  His  Pro  Ile  Glu  Gly  Ser  Thr  Thr  Val  Phe  His
                    2245                2250                          2255

Ser  Leu  Ala  Ser  Arg  Leu  Ser  Ile  Pro  Thr  Tyr  Gly  Leu  Gln  Cys  Thr
          2260                2265                          2270

Arg  Ala  Ala  Pro  Leu  Asp  Ser  Ile  His  Ser  Leu  Ala  Ala  Tyr  Tyr  Ile
          2275                2280                          2285

Asp  Cys  Ile  Arg  Gln  Val  Gln  Pro  Glu  Gly  Pro  Tyr  Arg  Val  Ala  Gly
          2290                2295                          2300

Tyr  Ser  Tyr  Gly  Ala  Cys  Val  Ala  Phe  Glu  Met  Cys  Ser  Gln  Leu  Gln
305                      2310                2315                          2320

Ala  Gln  Gln  Ser  Pro  Ala  Pro  Thr  His  Asn  Ser  Leu  Phe  Leu  Phe  Asp
          2325                2330                          2335

Gly  Ser  Pro  Thr  Tyr  Val  Leu  Ala  Tyr  Thr  Gln  Ser  Tyr  Arg  Ala  Lys
          2340                2345                          2350

Leu  Thr  Pro  Gly  Cys  Glu  Ala  Ala  Glu  Thr  Glu  Ala  Ile  Cys  Phe
          2355                2360                          2365

Phe  Val  Gln  Gln  Phe  Thr  Asp  Met  Glu  His  Asn  Arg  Val  Leu  Glu  Ala
          2370                2375                          2380

Leu  Leu  Pro  Leu  Lys  Gly  Leu  Glu  Glu  Arg  Val  Ala  Ala  Ala  Val  Asp
385                      2390                2395                          2400

Leu  Ile  Ile  Lys  Ser  His  Gln  Gly  Leu  Asp  Arg  Gln  Glu  Leu  Ser  Phe
                    2405                2410                          2415

Ala  Ala  Arg  Ser  Phe  Tyr  Tyr  Lys  Leu  Gly  Ala  Ala  Glu  Gln  Tyr  Thr
          2420                2425                          2430

Pro  Lys  Ala  Lys  Tyr  His  Gly  Asn  Val  Met  Leu  Leu  Arg  Ala  Lys  Thr
          2435                2440                          2445

Gly  Gly  Ala  Tyr  Gly  Glu  Asp  Leu  Gly  Ala  Asp  Tyr  Asn  Leu  Ser  Gln
          2450                2455                          2460

Val  Cys  Asp  Gly  Lys  Val  Ser  Val  His  Val  Ile  Glu  Gly  Asp  His  Arg
465                      2470                2475                          2480

Thr  Leu  Leu  Glu  Gly  Ser  Gly  Leu  Glu  Ser  Ile  Ile  Ser  Ile  Ile  His
                    2485                2490                          2495

Ser  Ser  Leu  Ala  Glu  Pro  Arg  Val  Ser  Val  Arg  Glu  Gly
          2500                2505                       2
```

( 2 ) INFORMATION FOR SEQ ID NO:11:

( i ) SEQUENCE CHARACTERISTICS:
        ( A ) LENGTH: 42 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( v i ) ORIGINAL SOURCE:

( x i ) SEQUENCE DESCRIPTION: SEQ ID NO:11:

Pro Lys Pro Lys Asn Pro Ala Asn Pro Val Gln Ile Leu Gly Gly His
1               5                   10                  15

Leu Asp Ala Lys Gly Ser Phe Pro Trp Gln Ala Lys Met Val Ser His
            20              25                  30

His Asn Leu Thr Thr Gly Ala Thr Leu Ile
            35              40

( 2 ) INFORMATION FOR SEQ ID NO:12:

( i ) SEQUENCE CHARACTERISTICS:
        ( A ) LENGTH: 42 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( v i ) ORIGINAL SOURCE:

( x i ) SEQUENCE DESCRIPTION: SEQ ID NO:12:

Lys Pro Lys Asn Pro Ala Asn Pro Val Gln Arg Ile Leu Gly Gly His
1               5                   10                  15

Leu Asp Ala Lys Gly Ser Phe Pro Trp Gln Ala Lys Met Val Ser His
            20              25                  30

His Asn Leu Thr Thr Gly Ala Thr Leu Ile
            35              40

( 2 ) INFORMATION FOR SEQ ID NO:13:

( i ) SEQUENCE CHARACTERISTICS:
        ( A ) LENGTH: 13 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( v i ) ORIGINAL SOURCE:

( x i ) SEQUENCE DESCRIPTION: SEQ ID NO:13:

Leu Gln Gln His Asp Val Ala Gln Glu Gln Trp Xaa Pro
1               5                   10

( 2 ) INFORMATION FOR SEQ ID NO:14:

( i ) SEQUENCE CHARACTERISTICS:
        ( A ) LENGTH: 27 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO (iv) ANTI-SENSE: NO (v) FRAGMENT TYPE: N-terminal (vi) ORIGINAL SOURCE:

(xi) SEQUENCE DESCRIPTION: SEQ ID NO:14:

```
Thr Lys Leu Gln Gln His Asp Val Ala Gln Gly Gln Trp Asp Pro Ser
 1               5                  10                  15
Gly Pro Ala Pro Thr Asn Leu Gly Ala Leu Asp
             20                  25
```

CANCER RELATED ANTIGEN

This application is a Division of U.S. Ser. No. 08/188, 426, filed Jan. 24, 1994, which is a Continuation-In-Part of U.S. Ser. No. 08/096,908, filed Jul. 26, 1993, now abandoned, which is a Continuation-In-Part of U.S. Ser. No. 07/917,716, filed Jul. 24, 1992, now abandoned, and a Continuation-In-Part of U.S. Ser. No. 07/735,522, filed Jul. 26, 1991, now abandoned, which is a Continuation-In-Part of U.S. Ser. No. 07/622,407, filed Dec. 4, 1990, now abandoned, which is in turn a Continuation of U.S. Ser. No. 07/297,722, filed Jan. 17, 1989, now abandoned, which are incorporated herein in their entirety by reference.

The work leading to this invention was supported in part by Grant No. RO1 CA 46143 from the National Institutes of Health. The U.S. Government retains certain rights in this invention.

BACKGROUND OF THE INVENTION

1. Field of the Invention

This invention relates to the field of human proteins which are expressed by neoplastic tissues and not by most normal tissues.

2. Summary of Related Art

Some carcinoma cells are slow to grow, resulting in tumors that do not pose severe short term risk to a patient having such cells. For instance, many prostate cancers progress so slowly that they are only detected after the patient dies from another cause. Such carcinomas are Safely left untreated. Other carcinomas metastasize and grow rapidly, resulting in death of the patient. Any treatment that can slow down the growth of these latter, more virulent carcinomas is desired.

At the time of diagnosis, at least 25 percent of patients with early breast cancer have clinically undetectable metastases. If patients with this status could be identified at the time of diagnosis, one could apply early, intensive chemotherapy to women with clinically occult systemic breast cancer. Conversely, toxic and expensive treatment may be delayed or withheld from patients with favorable prognosis. Traditional associations between the histopathological features and clinical course of the disorder cannot be used to differentiate between clinically aggressive and clinically indolent disease (Hunter, Cancer, 1980, 46:Suppl. 4:961–76). In contrast, several recent studies have demonstrated a relation between changes in oncogenes and prognosis. For example, in some studies, amplification of the HER-2/neu oncogene in patients with breast cancer correlated with overall survival and the disease-free interval between primary therapy and relapse (Slamon, et al., Science, 1987, 235:177–82; Varley, et al., Oneogene, 1987, 1:423–30; and van de Vijver, et al., N, Engl. 1. Med., 1988, 319:1239–45). Similarly, changes in both c-myc and c-myb are often identified in aggressive breast cancers (Yokota, et al., Science, 1986, 231:261–5), as is the loss of c-Ha-ras alleles (Theillet, et al., Cancer Res., 1986, 46:4776–81). The molecular genetic approach is promising both clinically, as a potential diagnostic and prognostic aid, and scientifically, as a means to explore the biology of neoplasia.

SUMMARY OF THE INVENTION

It is an object of the invention to provide a method of determining the prognosis of a solid tumor-bearing patient.

It is yet an additional object of the invention to provide a kit and method for breast cancer prognostication.

It is yet another object of the invention to provide a method to aid in detecting an increase in the number of tumor cells in a patient.

It is another object of the invention to provide a preparation of antibodies which is immunoreactive with a protein whose presence is correlated with a worsened prognosis in a solid tumor bearing patient but not immunoreactive with haptoglobin 1 or 2.

It is an object of the invention to provide a substantially pure preparation of a polypeptide having an amino acid sequence corresponding to the nucleotide sequence of the hpr gene and having the ability to stimulate the production of antibodies in a mammal which are immunoreactive with epitopes found on the hpr gene product but not found on haptoglobin 1 or 2.

These and other objects of the invention are provided by one or more of the embodiments described below.

A gene encoding a theoretical protein, whose sequence is highly homologous to but distinct from that of haptoglobin, was reported in the literature, and the gene was designated hpr (for haptoglobin related protein). The present inventors first discovered that a protein corresponding to this gene was actually expressed in humans, and further that the protein reacted with antibodies that were not immunoreactive with haptoglobin. These antibodies were designated "anti-Hpr" antibodies. Despite the fact that, unlike haptoglobin, synthesis of the hpr gene product has not been found in the liver, the present invention provides four different sources which do contain material reactive with Hpr-specific antibodies. Human breast carcinoma cells, human decidua, human placenta, and human pregnancy serum have all been found to contain material specifically cross-reactive with Hpr-specific antibodies.

In the parent application, U.S. Ser. No. 07/297,722, the protein found in the cytoplasm of breast carcinoma cells which was reactive with anti-Hpr antibodies was called Hpr protein. However, as shown herein, the protein from tumor cells differs in sequence and physical properties, and so the inventors now refer to this cytoplasmic protein as OA-519. OA-519 has been found to be an especially useful diagnostic marker in human solid tumors for predicting the propensity for tumor invasion and early metastasis. The inventor's new terminology, OA-519, is used generally in this disclosure in place of "Hpr protein" to refer to the cytoplasmic protein from tumor cells which is cross-reactive with the hpr gene product but not with haptoglobin 1 or haptoglobin 2 (Hp1 or Hp2).

In one embodiment a substantially pure preparation of polypeptide is provided having an amino acid sequence corresponding to the nucleotide sequence of the hpr gene. When the preparation of the polypeptide is administered to a mammal, it stimulates the production of antibodies which are immunoreactive with epitopes found on the hpr gene product but which are not found on haptoglobin 1 or 2. In another embodiment of the invention a preparation of such antibodies is provided.

In yet another embodiment of the invention a preparation of Hpr protein is provided which is substantially purified from Hp1 and Hp2.

In still another embodiment of the invention, a method of producing a preparation of a protein cross-reactive with the hpr gene product but not with haptoglobin 1 or 2 is provided. Human breast carcinoma cells are tested for immunoreactivity with antibodies which are reactive with epitopes present on the hpr gene product but not present on Hp1 or 2. Immunoreactive breast cancer cells are cultured and a cytoplasmic fraction containing a protein cross-reactive with the hpr gene product but not with haptoglobin 1 or 2 is harvested from the cultured cells. The cross-reactive protein (OA-519) may be purified by physicochemical or immunoaffinity methods, and antibodies may be produced by immunizing a mammal with the protein. In yet another embodiment, the invention provides a preparation of antibodies which immunologically bind OA-519, the cross-reactive protein from the cytoplasm of breast carcinoma cells.

In still another embodiment of the invention a method is provided for detecting proliferation of tumor cells in a patient. A sample is collected from a patient bearing a tumor. The mount of material cross-reactive with the hpr gene product but not with Hp1 or 2 in the sample is quantitated. The mount of the cross-reactive protein found in the sample is compared to the mount found in a control sample collected from a patient with no detectable tumor. An elevated mount of the cross-reactive protein in the tumor-beating patient's sample indicates proliferation of the tumor cells.

In another embodiment a kit for determining the prognosis of breast carcinoma is provided. The kit comprises a preparation of antibodies which is immunoreactive with epitopes present on a protein cross-reactive with the hpr gene product but not present on haptoglobin 1 or 2 and a means for detecting the antibodies. A method of prognosticating the course of a solid tumor is also provided wherein histological sections are contacted with a preparation of antibodies which is immunoreactive with a protein cross-reactive with the hpr gene product but not with haptoglobin 1 or 2. Antibody binding to the sections is determined.

In yet another embodiment of the invention a method is provided for assaying a biological fluid for the presence of a protein which is cross-reactive with the hpr gene product but not with haptoglobin 1 or haptoglobin 2. Antibodies immunoreactive with an epitope found on a protein cross-reactive with the hpr gene product but not found on Hp1 and Hp2 are attached to a solid support which is then contacted with a biological fluid containing an unknown quantity of the cross-reactive protein under conditions where antibody-antigen complexes form and are stable. The solid support is then contacted with a polypeptide which shares an epitope with the protein cross-reactive with the hpr gene product but not with Hp1 and Hp2, under conditions where antibody-antigen complexes form and are stable. The polypeptide also bears a detectable moiety so that the mount of polypeptide bound to the solid support can be quantitated by detecting and quantitating the detectable moiety. A control is performed wherein no biological fluid is contacted with the solid support, to determine 100% binding of the polypeptide to the support. The mount of binding reduction observed in the presence of biological fluid is correlated to the mount of the protein cross-reactive with the hpr gene product in the biological fluid.

These and other embodiments are disclosed below in the detailed description of the invention.

BRIEF DESCRIPTION OF THE FIGURES

The file of this patent contains at least one drawing executed in color. Copies of this patent with color drawings will be provided by the Patent and Trademark Office upon request and payment of the necessary fee.

FIG. 3 depicts sequences of: (1) protein predicted from the hpr gene sequence; (2)haptoglobin 1; and (3) haptoglobin 2, each of which aligns with the N-terminal beta chain sequence of the protein isolated from pregnancy serum.

FIGS. 10A and B show the staining of decidua with polyclonal antibodies raised against the synthetic peptide made according to the predicted sequence from the hpr gene.

FIG. 12B shows the peptide sequence analysis of OA-519.

FIG. 12C shows that OA-519 synthesizes fatty acids from acetyl- and malonyl-CoA.

FIG. 15 shows immunohistochemical staining of human breast carcinoma using antibodies raised against the synthetic peptide.

FIG. 18 shows the correlation between OA-519 expression and survival in breast carcinoma.

FIG. 21 shows the correlation between OA-519 expression and prognosis in ovarian carcinoma. The upper panel of FIG. 21 shows relapse free survival and the lower panel of FIG. 21 shows overall survival.

DETAILED DESCRIPTION OF THE INVENTION

Figure 1:
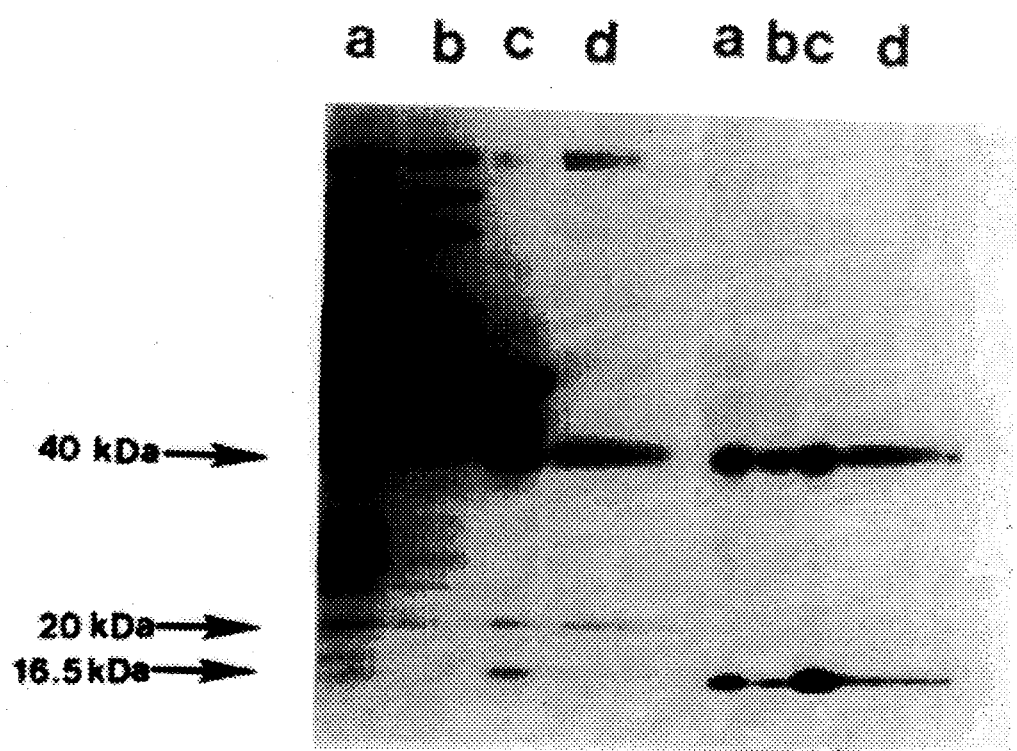
FIG. 1 shows the progressive purification of the hpr gene product. Polyacrylamide gel electrophoresis and corresponding western blots are shown of sequential chromatographic purification of plasma proteins reactive with anti-PAPP-A poly specific antibodies to pregnancy-associated plasma protein A, obtained from DAKO Laboratories.

In 1985, Maeda (*J. Biol. Chem.*, vol. 260, pp. 6698–6709, which is expressly incorporated herein), described a stretch of DNA located 2.2 kb downstream from the conventional haptoglobin locus. The DNA sequence indicated that the locus contained an intact gene coding for a theoretical protein whose alpha and beta chains are distinct from, but highly homologous to, conventional haptoglobins. Maeda called this locus hpr for "haptoglobin related." Several investigators failed to detect expression of this gene. (Oh, et al., Cancer Research, vol. 47, pp. 5120–5126, 1987; Maeda, *Journal of Biological Chemistry*, vol. 260, pp. 6698–6709, 1985; and Bensi et al., The EMBO Journal, vol. 4, pp. 119–126, 1985.)

A synthetic polypeptide has been made having the following amino acid sequence: leu-tyr-ser-gly-asn-asp-val-thr-asp-ile-ser-asp-asp-arg-phe-pro-lys-pro-pro-glu-ile-ala-asn-gly-tyr-val-glu-lys-leu-phe-arg-tyr-gln-cys which is identified as SEQ ID NO. 1. This polypeptide generally corresponds to the 34 N-terminal amino acids predicted from the nucleotide sequence of the hpr gene as identified by Maeda. This peptide is able to stimulate the production of antibodies in a mammal which are immunoreactive with epitopes found on the hpr gene product but which are not found on either haptoglobins 1 or 2. These antibodies can be used to reliably detect expression of the hpr gene in any human tissue as well as to purify the gene product using immunoaffinity techniques, which are well known in the art.

Conventional human haptoglobins have been well studied; they were discovered over 40 years ago and their role is thought to be in the plasma transport of free hemoglobin. Haptoglobin synthesis occurs mainly in the liver, although in some cases lymphocyte cultures and brain have been reported to synthesize haptoglobins. All haptoglobins contain two classes of polypeptide chains, beta chains and alpha chains. Beta chains are almost identical in all haptoglobins, whereas the alpha chains have been found in three forms. Two of the alpha chain forms (Hp1$^f$ and Hp1$^s$) differ only in a single amino acid residue at position 54. The third form (Hp2) is longer than either of the other two alpha chains, apparently having arisen by an unequal crossing over to partially duplicate the alpha chain.

It is a finding of the present invention that proteins, which are cross-reactive with a peptide according to SEQ ID NO. 1 which has hitherto been undetected, can be found in various human cells and tissues. These include: human breast carcinoma tissue, human decidua and placenta, serum from pregnant women, and cultured human breast carcinoma cell lines. The cross-reactive protein from pregnancy serum has been purified using physicochemical methods to be substantially pure of Hp1 and Hp2. The protein from pregnancy serum has an amino acid sequence corresponding to the nucleotide sequence of the hpr gene, and as predicted from its nucleotide sequence, it is very similar to haptoglobins 1 and 2, although there are a number of amino acid differences which cluster at the N-terminus of the alpha chain. This protein is called Hpr protein hereinafter.

The cross-reactive protein from the cytoplasm of cultured human breast carcinoma cell lines has also been purified by physiochemical methods to be substantially pure. cDNA encoding this cross-reactive protein has been cloned and the nucleotide sequence determined. Cloned plasmids pFAS 1.6, pFAS 3.0, pFAS 2.2, and pFAS 4.6 were deposited under ATCC Accession Nos. 75643, 75645, 75644, and 75646, respectively (see clone map in FIG. 12D). The sequence of this cytoplasmic protein is substantially unrelated to the sequence of the hpr gene, and the cytoplasmic protein is called OA-519 hereinafter. The sequence of OA-519 is highly homologous with rat fatty acid synthase.

The substantially pure preparation of polypeptide having an amino acid sequence corresponding to the nucleotide sequence of the hpr gene can be made using any of the techniques which are known in the art. For example, the Merrifield technique (*Journal of the American Chemical Society*, vol. 85, pp. 2149–2154, 1968), can be used. Substantial purity means that the preparation is almost totally free of haptoglobins 1 and 2. Polypeptides may be designed by comparing the amino acid sequences of Hpr protein, haptoglobin 1 and haptoglobin 2, and utilizing those regions of sequence which have the maximum amount of differences. The hpr gene sequence can be obtained from the publication of Maeda, *Journal of Biological Chemistry*, vol. 260, pp. 6698–6709, 1985, and the haptoglobin 1 and 2 sequences can be obtained from the database of the National Biomedical Research Foundation as well as from Kurosky, *Proceedings of the National Academy of Sciences USA*, vol. 77, pp. 3388–3392, 1980; Black et al., *Nature*, vol. 218, pp. 736–741, 1968; Black et al. *Canadian Journal of Biochemistry*, vol. 48, pp. 123–132, 1970; and Black et al. *Canadian Journal of Biochemistry*, vol. 48, pp. 133–146, 1970.

Although a sequence which corresponds to the 34 N-terminal amino acids of the predicted Hpr protein has been used, other polypeptides can be used as well. Other polypeptides may be made which are longer or shorter or have conservative amino acid changes which do not change the epitope(s) found on proteins cross-reactive with the hpr gene product but not found on Hp1 or Hp2. Preferred polypeptides for immunizing will have the sequence of OA-519, or a fragment of the sequence of OA-519 which is able to stimulate antibody production. Such fragments will usually contain at least 6 amino acids of the OA-519 sequence and frequently more than 10 amino acids of the sequence. The peptide fragments from the OA-519 sequence will usually be hydrophilic and represent a mobile sequence (not conformationally constrained). Preferably, the fragment of OA-519 will contain a sequence which is unique to human fatty acid synthase.

Polypeptides can be tested to determine if they are able to stimulate mammals to produce antibodies which are immunoreactive with epitopes found on proteins cross-reactive with the hpr gene product but not found on Hp1 or Hp2.

Methods of immunizing mammals to stimulate antibody production are well known in the art. Methods for testing the immunoreactivity of antibodies for known antigens are also well known.

A substantially pure preparation of a polypeptide of the present invention can be used to affinity purify antibodies specific for the proteins cross-reactive with the hpr gene product. In addition, the preparation of polypeptide of the present invention can be used to stimulate production of antibodies in a mammal by immunizing the mammal with the preparation. Usually, such immunization will employ coupling of the polypeptide to a larger immunogenic substance such as keyhole limpet hemocyanin. For affinity purification purposes, the polypeptide can be coupled to an inert matrix, such as agarose beads. Techniques for such coupling are well known in the art. The preparation of the polypeptide can also be used to quantitate Hpr-specific antibodies in an antibody preparation. In such a case, the synthetic peptide will usually be coupled to a larger inert proteinaceous substance such as bovine serum albumin. Once again, the techniques for coupling polypeptides to such matrices are well known in the art.

Purification of Cross-Reactive Protein

Applicants have found proteins cross-reactive with the hpr gene product in four different human cell types. Three of these cell types can practically be used to produce amounts of proteins cross-reactive with the hpr gene product for biochemical studies as well as studies to determine the biological effect of these proteins under physiological conditions. One particularly useful source is human breast carcinoma cell lines, which can be obtained from the American Type Culture Collection in Rockville, Md. One such cell line is called MDA-MB-231, and is an estrogen receptor negative cell line. Other such cell lines include ZR-75-1 and SK-Br-3. Hpr epitopes have been detected in the cytoplasm of about 50% of such breast carcinoma cell lines. Those cell lines readily can be identified, e.g., by use of antibodies immunoreactive with the polypeptide described above, having the 34 amino acid in SEQ ID NO. 1.

One means of preparing an Hpr-reactive protein preparation is to culture the human breast carcinoma cells which produce such a protein using culture conditions which are well-known in the art. The cells are then harvested and the cell membrane disrupted to obtain a cell lysate. The nuclei and membrane fractions can be removed and a cytoplasmic fraction containing proteins cross-reactive with the hpr gene product is obtained. Means of separating various cellular fractions, such as differential centrifugation, are indeed well-known in the art. Similarly, histological sections of breast tumors contain proteins cross-reactive with the hpr gene product, but this is a difficult tissue source to obtain in a quantity and manner permitting purification of the proteins.

Proteins cross-reactive with the hpr gene product have also been found in human decidua tissue and placenta. Such tissue can be collected from different sources and homogenized according to techniques well-known in the art. The cell membrane of the homogenized cells of the tissue can then be lysed to obtain a cytoplasmic fraction containing proteins cross-reactive with the hpr gene product. Serum from pregnant women has also been shown to contain proteins cross-reactive with the hpr gene product in recoverable amounts.

Once a cytoplasmic fraction containing proteins cross-reactive with the hpr gene product is obtained, purification the protein of can be accomplished according to techniques which are well-known in the protein purification art. For example, various types of chromatography may be used. Columns which have been found to be particularly useful include a CIBACRON F3GA SEPHAROSE column, a DEAE cellulose column, an anion exchange column, as well as a gel permeation column.

Proteins cross-reactive with the hpr gene product but not with haptoglobin 1 or haptoglobin 2 can also be purified using immunoaffinity techniques. Antibodies are provided herein which are specific for epitopes found on proteins cross-reactive with a peptide according to SEQ ID NO. 1 but not found on haptoglobin 1 or haptoglobin 2, and the cross-reactive proteins can be positively selected from a mixture of many proteins by binding to these antibodies. The use of the antibodies of the present invention to purify the proteins allows good separation from the proteins which are most similar to Hpr protein, namely haptoglobins 1 and 2. Of course, other techniques of purification are known in the art and can be used to purify the proteins of this invention.

The protein preparations which are obtained according to the present invention are substantially pure and probably homogeneous. This conclusion is based on visualization of proteins electrophoretically separated on polyacrylamide gels. In gels of Hpr protein purified from pregnancy plasma, no haptoglobin 2 is detected. Generally, substantially pure preparations are free of Hp1 and Hp2 and will have greater than 75% of the haptoglobin-type protein present being Hpr protein. More preferably, the preparations will contain greater than 90% of the haptoglobin type protein as Hpr protein. Gels of OA-519 purified from the cytoplasm of tumor cells or cell lines also show substantially pure protein.

Recombinant Production of Cross-Reactive Protein

It is possible to purify a cross-reactive protein from an appropriate tissue/fluid source; however, a cross-reactive protein or polypeptide may also be produced by recombinant methods from a DNA sequence encoding such a protein or polypeptide, which DNA sequence can be synthesized chemically or isolated by one of several approaches. The complete sequence may be assembled from overlapping oligonucleotides prepared by standard methods and assembled into a complete coding sequence. See, e.g., Edge (1981) *Nature* 292:756; Nambair, et al. (1984) *Science* 223:1299; Jay, et al. (1984) *J. Biol. Chem.*, 259:6311. The isolation methods will rely in part on nucleic acid hybridization using appropriate single stranded or double stranded nucleotide or oligonucleotide probes. Such probes can be constructed synthetically, based on the DNA or amino acid sequences disclosed herein, or isolated from genomic or cDNA clones also described herein.

The basic strategies for preparing oligonucleotide probes and DNA libraries, as well as their screening by nucleic acid hybridization, are well known to those of ordinary skill in the art. See, e.g., Sambrook, et al., "Molecular Cloning: a Laboratory Manual" (1989); B. Perbal, "A Practical Guide To Molecular Cloning" (1984). First, a DNA library is prepared. The library can consist of a genomic DNA library from a human source. Human genomic libraries are known in the art. More preferred are DNA libraries constructed of cDNA, prepared from poly-A-plus RNA (mRNA) by reverse transcription. The mRNA is isolated from a cell line or tissue believed to express the protein cross-reactive with a peptide according to SEQ ID NO. 1, such as a human breast carcinoma cell line. A suitable source of mRNA for cDNA library constructions is the cell line ZR-75-1. The genomic DNA or cDNA is cloned into a vector suitable for construction of a library. The construction of an appropriate library is within the skill of the art. See, e.g., B. Perbal, supra. Once the library is constructed, oligonucleotides are used to probe the library to identify the segment carrying a sequence encoding a cross-reactive protein, such as OA-519.

Nucleic Acid Probes

Oligonucleotides can be designed and produced for use as hybridization probes to locate the other coding sequences. In general, the probes are synthesized chemically, preferably based upon known nucleic acid sequences, such as the sequences of the clones shown in FIG. 12D. Ultimately, the isolated segments of DNA are ligated together in such a way that the correct mature protein is encoded.

However, it may become necessary to obtain internal sequences from the protein. This can be done, for example, by Staph-V8 proteolysis of protein purified in the usual way, which may be followed by reductive alkylation and separation by HPLC of the digestion products. Elution peaks corresponding to discrete enzyme fragments can then be sequenced by standard methods. Nucleotide sequences encoding portions of the protein can be predicted from the amino acid sequence. Nucleotide sequences are selected so as to correspond to codons encoding the amino acid sequence. Since the genetic code is redundant, it will usually be necessary to synthesize several oligonucleotides to cover all, or a reasonable number, of the possible nucleotide sequences which encode a particular amino acid sequence. Thus, it is generally preferred, in selecting a region of the sequence upon which to base the probes, that the region not contain amino acids whose codons are highly degenerate. It may not be necessary, however, to prepare probes containing codons whose usage is rare in humans (from which the library was prepared). Alternative methods using a long probe (greater than 35 bp) which is not degenerate may also be used as described by Lathe, R. (1985), J. Mol. Biol., 183:1–12 (discussed in Sambrook, et al.).

One of skill in the art may find it desirable to prepare probes that are fairly long and/or encompass regions of the amino acid sequence which would have a high degree of redundancy in the corresponding nucleic acid sequences. In other cases, it may be desirable to use two sets of probes simultaneously, each to a different region of the gene. While the exact length of any probe employed is not critical, typical probe sequences are no greater than 1000 nucleotides in length, more typically they are not greater than 500 nucleotides, even more typically they are no greater than 250 nucleotides; they may be no greater than 100 nucleotides, and also may be no greater than 75 nucleotides in length. Generally it is recognized in the art that probes from about 14 to about 20 base pairs are usually effective. Longer probe sequences may be necessary to encompass unique polynucleotide regions with differences sufficient to allow related target sequences to be distinguished. For this reason, probes are preferably from about 10 to about 100 nucleotides in length and more preferably from about 20 to about 50 nucleotides.

Selection of Clones

As is known in the art, oligonucleotide probes are usually labeled with a marker, such as a radionucleotide or biotin, using standard procedures. The labeled set of probes is then used in the screening step, which consists of allowing the single-stranded probe to hybridize to isolated ssDNA from the library, according to standard techniques. Either stringent or permissive hybridization conditions could be appropriate, depending upon several factors including, but not limited to, the length of the probe, whether the probe and library are from the same species, and whether the species are evolutionarily close or distant. It is within the skill of the art to optimize hybridization conditions so that homologous sequences are isolated and detectable above background hybridizations. The basic requirement is that hybridization conditions be of sufficient stringency so that selective hybridization occurs; i.e., hybridization is due to a minimum degree of nucleic acid homology (e.g., at least about 75%), as opposed to non-specific binding or hybridization due to a lower degree of homology. See generally, "Nucleic Acid Hybridization," (1985) B. D. Hames and S. J. Higgins, eds.

Where the library is an expression library, selection may be accomplished by expressing the library sequences and detecting the expressed peptides immunologically. Clones which express peptides which bind the antibodies of this invention are selected. These selection procedures are well known to those of ordinary skill in the art (see, e.g., Sambrook, et al.).

Alternatively, a nucleic acid whose sequence corresponds to the sequence of OA-519 may be used to detect chromosomal alterations such as amplifications, translocations, deletions and mutations using fluorescent in situ hybridization, Southern blot analysis, dot blot analysis, the polymerase chain reaction, or semi-quantitative modifications of the polymerase chain reaction. A nucleic acid whose sequence corresponds to the sequence of OA-519 may be used to select genomic clones corresponding to the OA-519 gene. Nucleic acids corresponding to the OA-519 gene may be characterized by standard sequencing techniques and may also be used in any of the foregoing assays.

Cloning for Expression

Once a coding sequence for the desired polypeptide sequence has been prepared or isolated, it can be cloned into any suitable vector or replicon and thereby maintained in a composition which is substantially free of vectors that do not contain the coding sequence (e.g., free of other clones from the library). Numerous cloning vectors are known to those of skill in the art, and the selection of an appropriate cloning vector is a matter of choice (see, e.g., Sambrook, et al., incorporated herein by reference). The DNA sequences and DNA molecules of the present invention may be expressed using a wide variety of host/vector combinations. According to the present invention, the coding sequence for the polypeptide which is cross-reactive with the hpr gene product is placed under the control of a promoter, ribosome binding site (for bacterial expression) and, optionally, an operator (collectively referred to herein as "control" elements), so that the DNA sequence is transcribed into RNA in the host cell transformed by a vector containing this expression construct. The coding sequence may or may not contain a signal peptide or leader sequence.

Of course, not all host/expression vector combinations function with equal efficiency in expressing the DNA sequences of this invention or in producing the polypeptides of this invention. However, a particular selection of a host/expression vector combination may be made by those skilled in the art. For example, the selection should be based on a balancing of a number of factors. These include compatibility of the host and vector, toxicity of the proteins encoded by the DNA sequence to the host, ease of recovery of the desired protein, expression characteristics of the DNA sequences and the expression control sequences operatively linked to them, biosafety, costs and the folding, form or any other necessary post-expression modifications of the desired protein. Preferably, the host cell will not express proteases which degrade the recombinant polypeptide of this invention.

Depending on the expression system and host selected, the protein is produced by growing host cells transformed by an expression vector containing the coding sequence for a polypeptide cross-reactive with the hpr gene product under conditions whereby the protein is expressed. The protein is then isolated from the host cells and purified. The selection of the appropriate growth conditions and recovery methods are within the skill of the art.

Production of Antibodies

Mammals immunized with the hpr gene product, with a peptide whose sequence is listed as SEQ ID NO. 1, or with a protein cross-reactive with a peptide whose sequence corresponds to SEQ ID NO. 1, will produce polyclonal antibodies contemplated by this invention. As mentioned above, antibodies which are specific for the Hpr protein in that they are immunoreactive with Hpr protein but not with either haptoglobins 1 or 2 can be made using a synthetic polypeptide of the present invention. Preferred polypeptides for use in immunizing mammals to obtain antibodies according to this invention will have all or part of the amino acid sequence of OA-519. Immunization of mammals such as rabbits, mice, goats, etc. to produce antibodies is well known in the art. Polyclonal antibody preparations can be partially purified using immunoaffinity techniques employing a synthetic polypeptide of the present invention. Immunoaffinity purification of polyclonal antibodies may also employ proteins purified according to this invention, or polypeptide fragments of such proteins. Such purification methods are well-known in the art.

Monoclonal antibodies can also be raised which are specific for Hpr epitopes and do not cross-react with haptoglobin 1 or 2. Generally, a rat or mouse will be immunized with the synthetic polypeptide of the present invention (or a protein cross-reactive with a peptide according to SEQ ID NO. 1) and the rodent will later be sacrificed and spleen cells recovered for fusion with myeloma cells. Hybrid cells can be selected according to techniques known in the art, for example, selections involving complementation of two phenotypes, one from each parental cell. Antibody production of each hybrid cell can be screened individually. Antibodies which bind to epitopes on proteins cross-reactive with Hpr protein but not on Hp1 or Hp2 may bind Hpr or any other protein expressing these epitopes. In one embodiment of this invention, monoclonal antibodies are selected which bind to OA-519, but do not bind to Hpr.

In order to screen for antibodies which are immunoreactive with epitopes found on proteins cross-reactive with the hpr gene product but not found on Hp1 or Hp2, a simple battery of tests can be performed. (1) Antibodies can be tested for immunoreactivity with proteins cross-reactive with Hpr protein using a substantially pure preparation of Hpr protein or a cross-reactive protein, or with the preparation of polypeptide of the present invention conjugated to a larger moiety such as bovine serum albumin. The desired specific antibodies should be positive in either or both of these tests. (2) The antibodies should also be tested for immunoreactivity with Hp1 and Hp2. Desired antibodies having absolute specificity for Hpr protein or a cross-reactive protein should be negative in both such tests.

Antibodies can also be detected using this battery of tests which have relative specificity for Hpr protein relative to Hp1 and Hp2. That is, some monoclonal antibodies can be found which react more strongly with Hpr protein than with Hp1 and Hp2. These antibodies of relative specificity for Hpr protein may also be useful. Means for using them are discussed below.

Antibodies that are immuno-reactive with OA-519 but not Hpr can be selected using similar tests. In particular, these antibodies are positive in tests for binding to purified OA-519 and negative in tests for binding to purified Hpr. These antibodies are preferred for use in assays of serum or blood for the presence of OA-519.

Immunoaffinity techniques can be used to purify mono-specific polyclonal antibodies specifically reactive with a protein cross-reactive with a peptide according to SEQ ID NO. 1 but not with Hp1 or Hp2. Similar binding properties are employed as in the tests described for monoclonal antibodies above. That is to say that antibodies which immunoreact with Hpr protein or a cross-reactive protein will be positively selected, while those that immunoreact with Hp1 and Hp2 will be removed from the desired antibody preparation.

Antibodies which show relative or preferential specificity for Hpr protein relative to Hp1 and Hp2 can be rendered absolutely specific by altering the conditions under which immunoreactivity is assayed. Conditions in the assay medium which can be altered include, but are not limited to: the ionic strength; the detergent concentration; the concentration of chaotropic agents, such as urea, guanidine, and potassium thiocyanate; and the pH. Alteration of these conditions leads to destabilization of the various bonding forces which contribute to antibody-antigen binding. Titration of reagents altering each of these conditions allows determination of a set of conditions where relatively or preferentially specific antibodies immunoreact with Hpr protein but not with Hp1 or Hp2. Suitable ranges in which to vary the destabilizing agent concentrations can readily be determined. For example, in order to alter ionic strength, potassium chloride can be titrated from about 0.05M to 2M. Detergents, either ionic or non-ionic, can be titrated from about 0.05% to 2%. Chaotropic agents can be titrated from about 0.5M to 8M. The range of pH can be titrated from about 2 to 10. Such conditions can be useful both to screen for monoclonal antibodies immunoreactive with Hpr epitopes and to assay for proteins containing such epitopes in various biological sources. The above-described method of tinting various destabilizing agents can also be used with other antibody-antigen pairs to enhance the specificity of reaction.

Diagnostic Assays

Detection of proteins cross-reactive with the hpr gene product but not with haptoglobin 1 or 2, and their expression, may be on the nucleotide or peptide level. Antibodies can be prepared by immunizing mammals with peptides expressed from nucleic acid sequences corresponding to cross-reactive polypeptides, as indicated above, and selecting those antibodies specific to the cross-reactive polypeptides using techniques that are well known to those skilled in the art. These antibodies can detect the presence of cross-reactive protein by a variety of immunoassay techniques. The nucleotide probe sequences provided by the invention can be used to detect expression of mRNA corresponding to cross-reactive proteins in accordance with any of the standard techniques. Expression may be detected either by in situ hybridization or by extraction and detection of mRNA. The particular procedures for gene probe assays and immunoassays will be well-known to those skilled in the art.

Immunoassays

The antibodies of the present invention can be used to detect epitopes found on proteins cross-reactive with a peptide according to SEQ ID NO. 1 but not found on haptoglobin 1 or haptoglobin 2 in histological sections of breast cancer tissue as well as in other solid tumors such as, lung cancer tissue, genito-urinary tumor tissue and gastrointestinal tumor tissue. It has been found that the presence of such epitopes in breast cancer tissue correlates with a worsened prognosis; it indicates that the cancer will probably recur early and metastasize early, compared to those whose tissues are negative for Hpr epitopes. Breast tissues in which such epitopes are found are characterized by three qualifies: the immunoreactivity is present in infiltrating breast carcinoma; granular cytoplasmic immunoreactivity is observed without nuclear staining; and the staining is heterogeneous, i.e., there is cell-to-cell or region-to-region variability.

One can detect antibody binding to tissue sections by any detection means known in the art for example, a radiolabel or a stain. A particularly useful stain employs peroxidase, hydrogen peroxide and a chromogenic substance such as aminoethyl carbazole. The peroxidase (a well known enzyme available from many sources) can be coupled to an anti-Hpr antibody or merely complexed via one or more antibodies to an antibody which specifically binds a protein which is cross-reactive with a peptide according to SEQ ID NO. 1. For example, a goat anti-peroxidase antibody and a goat anti-Hpr antibody can be complexed via an anti-goat IgG. Such techniques are well known in the art. Other chromogenic substances and enzymes may also be used. Radiolabeling of antibodies may also be used to detect antibody binding to sections. Labeled antibodies may be anti-Hpr or second antibodies immunoreactive with anti-Hpr antibodies. Again, such techniques are well known.

The precise technique by which a protein cross-reactive with the hpr gene product is detected in breast cancer patients is not critical to the invention. Biochemical or immunological techniques can now be used which do not employ immunohistochemistry, although that is the preferred method of the present invention. Solution assay methods, including colorimetric, chemiluminescent or fluorescent immunoassays such as ELISA, sandwich and competitive immunoassays, immuno-diffusion, radio immunoassay, immunoelectrophoresis, Western blot and other techniques, may be used to detect and quantitate proteins cross-reactive with a peptide according to SEQ ID NO. 1 in a patient by preparing an extract of a tissue sample from the patient and assaying the extract.

A protein cross-reactive with the hpr gene product can be quantitated in a biological fluid, such as serum, plasma, effusions, ascites, urine, cerebrospinal fluid, semen, breast aspirates and fluids of ovarian origin, using any protein detection means known in the art. Preferred methods employ immunological detection means. These include: radioimmunoassay, enzyme linked immunoadsorbent assay, complement fixation, nephelometric assay, immunodiffusion or immunoelectrophoretic assay and the like. Plasma should be anti-coagulated before use, as is known in the art. Cellular elements and lipid may be removed from fluids, e.g., by centrifugation. For dilute fluids, such as urine, protein may be concentrated, e.g., by ultra-filtration or salting-out.

One preferred method of detecting and/or quantitating a protein cross-reactive with the hpr gene product in fluid samples employs a competitive assay. An antibody immunoreactive with an epitope found on a protein cross-reactive with Hpr protein but not found on Hp1 and Hp2 is attached to a solid support such as a polystyrene microtiter dish or nitrocellulose paper, using techniques known in the art. The solid support is then incubated in the presence of the fluid to be analyzed under conditions where antibody-antigen complexes form and are stable. Excess and unbound components of the fluid are removed and the solid support is washed so that antibody-antigen complexes are retained on the solid support. A fixed amount of a polypeptide containing an epitope bound by the antibody attached to the solid support is then incubated with the solid support. The polypeptide binds to any unbound antibody which is attached to the solid support. The polypeptide has been conjugated to a detectable moiety, such as biotin, peroxidase or radiolabel, by means well known in the art. Excess and unbound polypeptide is removed and the solid support is washed, as above. The detectable moiety attached to the solid support is quantitated. Since any cross-reactive protein in the sample and the polypeptide have competed for the same antibody binding sites, the cross-reactive protein in the fluid can be quantitated by its diminution of the binding of the polypeptide to the solid support. Antibodies employed in this assay may have absolute immunoreactive specificity for a protein cross-reactive with a peptide according to SEQ ID NO. 1 but not react with Hp1 or Hp2. Alternatively, relatively specific antibodies may be used under conditions which destabilize immunoreactivity with Hp1 and Hp2. Polyclonal antibodies which contain an antibody species immunoreactive with an epitope on Hpr protein but not on Hp1 or Hp2, may also be used.

Although this assay has been described with particularity to the hpr system, it can also be used to quantitate other protein analytes in biological fluids. That is, a detectably labeled polypeptide which shares an epitope with a protein analyte can be used to quantitate the analyte. A monospecific antibody is not required as the specificity is provided to the assay by means of the polypeptide.

Nucleotide Probe Assays for Expression

The nucleic acid probes described above for use in screening gene libraries and selecting clones may also be used to detect mRNA transcripts in tumor cells that express a protein cross-reactive with the hpr gene product. These probes preferably correspond to a sequence which encodes portions of the distinct sequences of OA-519 (see FIG. 12D). The probe can be either single or double stranded DNA or RNA. The size of a probe can vary from less than approximately 20 nucleotides to hundreds of nucleotides. The most desirable nucleotide probes do not detect nucleotide sequences unrelated to their intended target, do not show significant homology with unrelated nucleotide sequences, and do not contain complementary sequences such that they would self-hybridize or fold upon themselves. The guanine and cytosine content of desirable probes is not so high as to promote non-specific hybridization with unrelated sequences rich in guanine and cytosine. Finally, the melting temperature and free energy of binding are generally favorably suited to the detection technique for which they are intended. The probe may be radio-labeled, labeled with a fluorescent material, a biotinylated nucleotide, or the like. Procedures for the preparation and labeling of nucleotide probes are well known in the art.

In situ hybridization of nucleotide probes to tissue sections is performed using standard methods, as described by, e.g., Baldino, et al., *Methods in Enzymol.*, 1989, vol. 168, p. 761–77; Emson, et al., *Methods in Enzymol.*, 1989, vol. 168, p. 753–61; Harper, et al., *Methods in Enzymol.*, 1987, vol. 151, p. 539–51; Angerer, et al., *Methods in Enzymol.*, 1987, vol. 152, p. 649–61; Wilcox, et al., *Methods in Enzymol.*, 1986, vol. 124, p. 510–33, incorporated herein by reference, using nucleotide probes described above. One preferred method for detecting mRNA associated with expression of the cross-reactive protein is in situ hybridization to tissue sections taken from tumors. Detection of hybridization by a probe having a nucleotide sequence corresponding to the amino acid sequence of OA-519 in the cytoplasm of tumor cells indicates expression by that cell of mRNA corresponding to a protein cross-reactive with the hpr gene product. Tissue sections are prepared as for immunohistochemistry.

Alternatively, extracts of RNA from tissue samples can be analyzed for the presence of sequences encoding the proteins of this invention. The diagnostic test employing a nucleotide probe will employ a biological sample from an individual. Nucleic acids are recovered from the sample employing standard techniques well known to those skilled in the art. The nucleic acid then is incubated with the probe and hybridization is thereafter detected. The presence of a nucleic acid whose sequence corresponds to that of the probe is preferably detected by Northern blot, or slot/dot blot.

Alternatively, a nucleic acid whose sequence corresponds to the sequence of OA-519 may be detected in the RNA extract of tumor tissue by nucleic acid amplification, using primers corresponding to the nucleic acid sequence of OA-519, (see methods reviewed in Van Brunt, BioTechnology, 8:291–294, 1990). Similar primers can be used to amplify genomic DNA sequences encoding OA-519. The preferred method of amplification uses the polymerase chain reaction (PCR). Primers can be constructed corresponding to unique portions of the nucleic acid sequence of OA-519, determined as described above for nucleic acid probes. Using these primers, RNA or DNA in a nucleic acid extract of tumor tissue will be amplified by PCR only if it contains the unique OA-519 sequences.

An elevated level of OA-519 mRNA in a cell corresponds to elevated FAS protein expression by the cell, and OA-519 mRNA can be quantitated in a number of ways. Using Northern blotting or dot hybridization, purified RNA samples of known concentration and integrity can be hybridized with labeled OA-519 probes. For each sample, the signal which is obtained can be compared ratiometrically to the signal obtained when the same sample is hybridized to a labelled probe for a constitutively expressed gene whose expression does not vary from cell to cell or sample to sample. Comparison of the ratios between different samples permits estimation of the differences in OA-519 levels.

Alternatively, the level of OA-519 mRNA expression can be estimated by quantitative polymerase chain reaction. Using primers whose sequences correspond to the OA-519 nucleotide sequence, cDNA can be synthesized initially using reverse transcriptase, then the resultant cDNA amplified according to the polymerase chain reaction. The reaction is run under conditions and terminated so as to produce amounts of amplified products in proportion to the amount of mRNA originally present in the sample. The amount of product can be quantitated by ethidium fluorescence in comparison to known standards following electrophoresis, or by dot hybridization with labeled probes. Expression of constitutively expressed genes can be measured as a control, permitting standardized comparison of results, such as with the previously described hybridization reactions. Treatment of samples with ribonuclease A or other RNAses in control samples prior to amplification verifies that the signal is derived soley from RNA.

Elevated levels of a protein cross-reactive with a peptide according to SEQ ID NO. 1 (e.g., OA-519) in a sample, such as the blood or other biological fluid, from a patient correlates with proliferation and likely metastasis of breast cancer as well as other solid tumors. Other tumors include lung cancer, genito-urinary tumors, and gastrointestinal tumors. The determination of elevated levels of a protein cross-reactive with a peptide according to SEQ ID NO. 1 is done relative to a patient with no detectable solid tumor. This may be the same patient or a different patient. For example, a first sample may be collected immediately following surgical removal of a solid tumor. Subsequent samples may be taken to monitor recurrence of tumor growth and/or tumor cell proliferation. Determination of the elevated level of cross-reactive protein may be done by direct detection of the protein or by indirect detection of its expression via measurement of mRNA encoding the protein. The detection may be in tissue sections by immunohistochemistry or in situ hybridization or it may be in extracts of tissue samples by solution immunoassay, or mRNA hybridization or amplification. In addition, the assay of a protein cross-reactive with a peptide according to SEQ ID NO. 1 in biological fluids can be used to distinguish between neoplastic and non-neoplastic fluid accumulations in patients carrying a malignant diagnosis.

The diagnostic methods of this invention are predictive of proliferation and metastatic potential in patients suffering from breast carcinomas including lobular and duct carcinomas, and other solid tumors, carcinomas, sarcomas, and cancers including carcinomas of the lung like small cell carcinoma, large cell carcinoma, squamous carcinoma, and adenocarcinoma, mesothelioma of the lung, colorectal adenocarcinoma, stomach carcinoma, prostatic adenocarcinoma, ovarian carcinoma such as serous cystadenocarcinoma and mucinous cystadenocarcinoma, ovarian germ cell tumors, testicular carcinomas, and germ cell tumors, pancreatic adenocarcinoma, biliary adenocarcinoma, heptacellular carcinoma, bladder carcinoma including transitional cell carcinoma, adenocarcinoma, and squamous carcinoma, renal cell adenocarcinoma, endometrial carcinomas including adenocarcinomas and mixed Mullerian tumors (carcinosarcomas), carcinomas of the endocervix, ectocervix, and vagina such as adenocarcinoma and squamous carcinoma, tumors of the skin like squamous cell carcinoma, basal cell carcinoma, melanoma, and skin appendage tumors, esophageal carcinoma, carcinomas of the nasopharynx and oropharynx including squamous carcinoma and adenocarcinomas, salivary gland carcinomas, brain and central nervous system tumors including tumors of glial, neuronal, and meningeal origin, tumors of peripheral nerve, soft tissue sarcomas and sarcomas of bone and cartilage. Cells of these tumors which express a protein cross-reactive with the hpr gene product but not with Hp1 or 2 are aggressive tumor cells and result in decreased survival, increased metastasis, increased rates of clinical recurrence and overall worsened prognosis.

The following examples are not intended to limit the invention, but merely provide specific embodiments which can be employed.

EXAMPLES

Example 1

This example describes the isolation and purification of Hpr protein from human pregnancy plasma, and the separation of the two subunits.

Maternal plasma from third trimester pregnancies was obtained from discarded EDTA-anticoagulated whole blood samples. The plasma was stored at −70° C. until use.

Proteins reactive with the whole IgG fraction of a rabbit antiserum to pregnancy-associated plasma protein A (PAPP- A) (Dako Laboratories, Santa Barbara, Calif.) were purified by successive chromatographic steps. The purification was monitored by optical density of chromatographic effluents at 280 nm, and analysis of fractions using Coomassie-stained Laemmli gels, and Western blotting. Initially, 80 ml of plasma was loaded onto a 2.5×30 cm CIBACRON BLUE F3G-A SEPHAROSE (Pharmacia) column equilibrated in 50 mM sodium phosphate, pH 6.8 at 4° C. The flow-through containing all the detectable immunoreactive material was dialyzed against 20 mM sodium phosphate, pH 6.8 at 4° C. with 1 mM $NAN_3$, and applied to 2.5×10 cm column of DE-52 DEAE-cellulose (Pierce Chemical Co.) equilibrated in the same buffer. The immunoreactive material was eluted with 0.2M NaCl in the starting buffer. The eluate was dialyzed against 20 mM Tris-HCl, pH 8.5 at 4° C. containing 0.15M NaCl, 1 mM beta-mercaptoethanol, and 1 mM $NAN_3$, then loaded onto a 2.5×60 cm column of FAST FLOW Q-SEPHAROSE (Pharmacia, Piscataway, N.J.) equilibrated in the same buffer. The column was eluted with a 500 ml linear gradient of 150 mM to 500 mM NaCl at a flow-rate of 100 ml/hr at 4° C. The immunoreactive protein species eluted in the range between 0.25 and 0.28M NaCl. The fractions containing immunoreactive protein were pooled and dialyzed against 200 mM Tris-acetate, pH 7.5 at 4° C. with 1 mM beta-mercaptoethanol and 1 mM $NaN_3$ and applied to a 5×90 cm SEPHAROSE CL-4B (Pharmacia) column.

FIG. 1 summarizes the purification of the dominant immunoreactive bands recognized by the polyspecific anti-PAPP-A (Dako). The figure shows a Coomassie stained 10–15% Laemmli gel (Nature, vol 227, pp. 680–685, 1970) and corresponding Western blot. Western blotting was carried out essentially according to published procedures. Following $NaDodSO_4$ polyacrylamide gel electrophoresis, protein was transferred to 0.45 u nitrocellulose sheets (Schleicher & Schuell) in 96 mM glycine, 12.5 mM Tris, 0.1% $NaDodSO_4$, and 20% methanol at 40 V, 250–300 mA, at 4° C. for 6 hrs. After evaluating transfer efficiency by Ponceau S staining, the membranes were blocked with 3% bovine serum albumin, then incubated sequentially with anti-PAPP-A antibody for 2 h and protein A labeled with $^{125}I$ for 1 h (Gershoni, et al., Analyt. Biochem., vol. 131, pp. 1–15, 1983). Washes after each step were performed in Tris-saline containing 1 mM $NaN_3$.

Sequential chromatographic steps involved removal of albumin and additional protein species on CIBACRON BLUE F3GA SEPHAROSE, (Lane a), step elution from a DEAE cellulose column (Lane b), gradient elution from a FAST-FLOW Q SEPHAROSE anion exchange column (Lane c), and gel permeation chromatography on SEPHAROSE CL-4B (Lane d). Interestingly, gel filtration incompletely resolved the immunoreactive proteins into three consecutively-eluting species consisting of the 40 kDa species co-eluting with the weakly reactive 20 kDa species, the 40 kDa band co-eluting with a weakly immunoreactive 16.5 kDa species, and lastly, as a separate, albeit overlapping peak, the 40 kDa species co-eluting with strongly immunoreactive 16.5 kDa band. (Molecular weights reported herein generally refer to the molecular weight determined by SDS-PAGE.)

To separate the individual immunoreactive chains under denaturing conditions, fractions containing immunoreactive protein were pooled and dialyzed against 20 mM Tris-HCl, 6M urea, 10 mM beta-mercaptoethanol, pH 8.5 at 25° C. (dialysis was performed at 4° C., but the pH was adjusted to be 8.5 at the indicated temperature). The final purification step utilized HPLC on a Waters system with a 5×50 mm MONO Q HR5/5 (Pharmacia) column monitored at 280 nm. The sample was injected in the Tris-urea-mercaptoethanol starting buffer and following 10 ml of isocratic flow at 2 ml/min, a linear gradient of 30 ml over 15 min was applied to final conditions of starting buffer with 0.5M NaCl.

Figure 2:
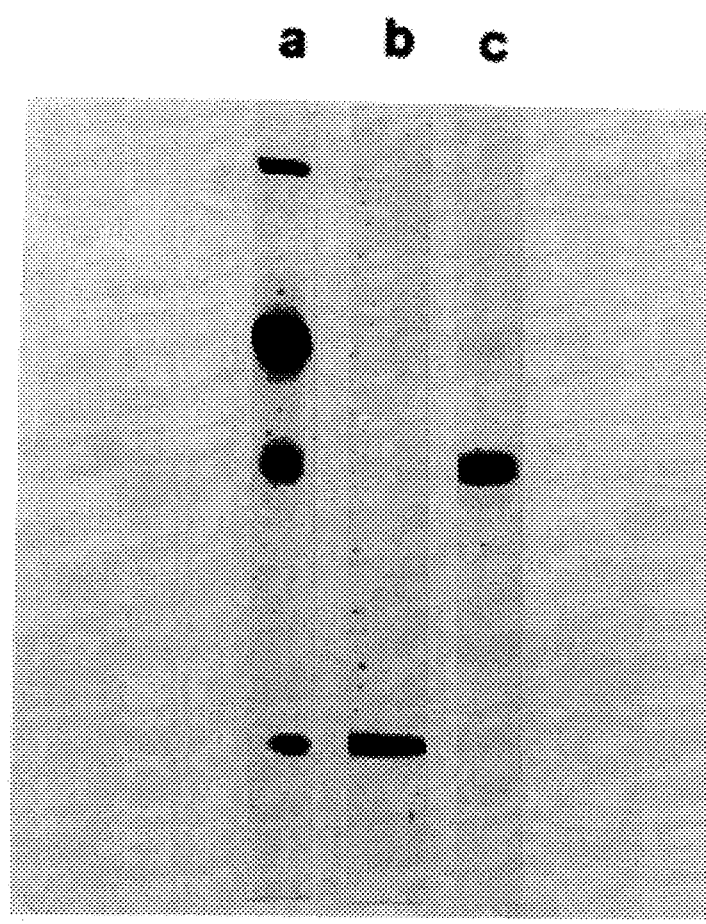
FIG. 2 shows a polyacrylamide gel electrophoretic separation of immunoreactive heavy and light chains by gradient anion exchange chromatography.

A Coomassie blue stained 10% Laemmli gel showing the separation of immunoreactive heavy and light chains by gradient anion exchange chromatography on MONO Q HR5/5 using HPLC is shown in FIG. 2. Lane a is 100 ug of purified immunoreactive protein. Lane b contains the alpha chains, which flowed through in the void volume, while lane c contains the immunoreactive 40 kDa chain which eluted in 0.85M NaCl. Fractions containing the 40 kDa species were pooled, dialyzed against 0.2M $NH_3HCO_3$ buffer and lyophilized.

Example 2

This example demonstrates that a 20-amino acid stretch of the heavy chain (beta chain) of Hpr protein is 100% homologous to the beta chains of haptoglobin 1 and 2.

The lyophilized samples of the 40 kDa species made according to Example 1 were dialyzed against three changes of 0.2M $NH_4HCO_3$ and lyophilized, then thrice re-lyophilized from HPLC-grade water. Gas phase sequencing was carried out. Samples of intact protein chains generally consisted of 100 ug of protein as determined by Lowry assay (J. Biol. Chem., vol. 193, pp 265–275, 1951). Peptide samples generally consisted of 0.5–2 nanomoles as quantitated by the sequencer. Protein was sequenced on an APPLIED BIOSYSTEMS MODEL 470A SEQUENATOR equipped with on-line phenylthiohydantoin (PTH) analysis using the regular program O3RPTH. The PTH derivatives were separated by reversed phase HPLC over an APPLIED BIOSYSTEM 200×21 mm C-18 column.

N-terminal sequencing yielded twenty residues shown in FIG. 3. Using the protein sequence database of the National Biomedical Research Foundation and the DFASTP alignment program three protein sequences showed 100% homology over the entire 20 amino acid stretch: the beta-chain of human haptoglobin 1; the beta-chain of human haptoglobin 2; and the predicted beta-chain of haptoglobin-related protein precursor.

Example 3

This example demonstrates that the haptoglobin-type protein isolated from pregnancy serum according to Example 1 differs from Hp1 and 2 in its 16.5 kDa chain.

Figure 4:
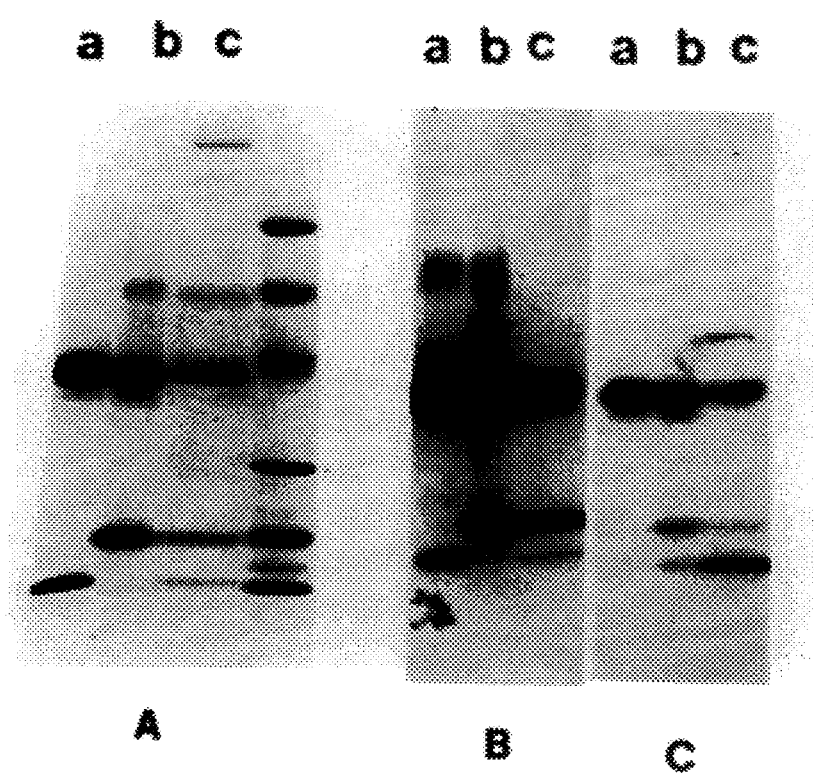
FIG. 4, parts A–C shows a polyacrylamide gel electrophoretic separation of haptoglobin 1, haptoglobin 2 and purified pregnancy associated protein (hpr gene product), as well as the corresponding immunoblots with anti-haptoglobin, and anti-PAPP-A.

Although sequence analysis placed the pregnancy plasma protein unequivocally in the haptoglobin (Hp) gene family, more specific assignments could not be made, since the N-terminal sequence for the beta-chains of all species is identical. FIG. 4 shows the results of an immunologic analysis performed with purified Hp1 and 2 standards, the haptoglobin-type protein purified from pregnancy Serum, rabbit anti-haptoglobin and the anti-PAPP-A. Panel A shows a 10–15% Coomassie stained Laemmli gel of Hp1, Hp2, and the haptoglobin-type protein purified from pregnancy serum (lanes a-c, respectively). Panel B is a corresponding immunoblot with anti-haptoglobin, 1:50; panel C is an immunoblot with anti-PAPP-A, 1:50.

Anti-haptoglobin reacts strongly with all the 40 kDa beta chains, and Hp1 and 2 alpha chains; the 16.5 kDa band from lane c containing the purified protein is only weakly reactive. In contrast, anti-PAPP-A, while strongly labeling the 40 kDa beta chains, reacts weakly with Hp2 alpha chain and is only slightly reactive with Hp1 alpha chain. The 16.5 kDa band from the purified protein in lane C is disproportionately intense in comparison to its Coomassie staining, particularly when compared to the disproportionately weak relative immunoreactivity of the Hp1 alpha chain shown in lane a. Thus, the alpha chain isolated from pregnancy plasma is immunologically distinct, containing epitopes seen by the anti-PAPP-A which are not present in either the Hp1 or Hp2 alpha chains.

Example 4

This example demonstrates that there are sequence differences between the alpha chain of Hpr protein and those of Hp1 and Hp2. In addition, the difference seen is consistent with the assignment of the haptoglobin from pregnancy serum as being the hpr gene product.

Peptide mapping was performed using the Elder technique (Speicher, et al. Proc. Natl. Acad. Sci. USA, vol. 77, pp 5673–5677, 1980; and Elder, et al., J. Biol. Chem., vol. 252, pp 6510–6515, 1977). Briefly, slices containing the desired proteins were exercised from Coomassie-stained gels, exhaustively radioiodinated, and enzymatically digested with trypsin. The resultant limit peptides were then subjected to high-voltage electrophoresis along one dimension of a cellulose sheet, followed by ascending partition thin layer chromatography in the perpendicular dimension.

Figure 5:
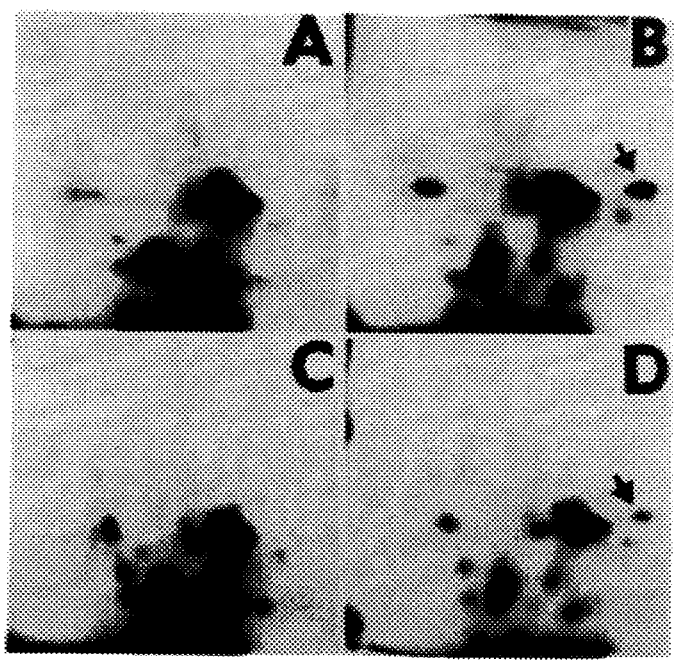
FIG. 5, parts A–D shows tryptic peptide maps of haptoglobin alpha chains of haptoglobin 1, hpr gene product, haptoglobin 2, and a mixture of haptoglobins.

Peptide mapping by this technique detects only tyrosine-containing peptides. Using the published amino acid sequences, the family of tryptic peptides from the chains of Hp1 and Hp2 should each be similar, since Hp2 resulted from a partial reduplication of Hp1 (FIGS. 5a and 5c). The principal differences in amino acid sequence between Hpr protein, Hp1 and Hp2 lie in the alpha chains. Within the alpha chains, these differences cluster principally at the N-termini. With reference to peptide mapping, using the deduced hpr gene alpha chain sequence one would predict the same tryptic peptides as obtained from Hp1 plus one additional tyrosine-containing peptide. FIG. 5b shows the peptide map of the purified protein alpha chain with an arrow highlighting the one additional peptide obtained experimentally. These results thus suggest that the unique haptoglobin-type protein purified from pregnancy plasma is the hpr gene product. FIG. 5d is a mixing experiment where Hp1 and the purified protein alpha chain were mixed before mapping. Again, the additional peptide is present but with less relative intensity, while the shared peptides all co-migrate.

Example 5

This example demonstrates that the alpha chain of the haptoglobin-type protein from pregnancy serum shares epitopes with a synthetic peptide made according to the deduced Hpr protein sequence.

A synthetic peptide corresponding to the 34 N-terminal residues of the predicted hpr gene product (Maeda et al., Proc. Natl. Acad. Sci. USA, vol. 83 pp.7395–7399, 1986) was synthesized on an Applied Biosystems Model 43A peptide synthesizer by the solid phase method of Merrifield (J. Am. Chem. Soc., vol. 85, pp. 2149–2154, 1968). Because histidine coupling can be inefficient, lysine was conservatively substituted for the histidine in position 28.

Two separate columns were made using beads coupled to: haptoglobin 1, and the 34-mer synthetic peptide. Haptoglobin 1 (Hp1) and the Hpr synthetic peptide were immobilized using agarose beads derivatized with 1,1-carbonyldimidazole (Reacti-Gel 6X, Pierce) which results in a stable N-alkylcarbamate linkage. 5ml of gel was washed with 0.1M borate and 0.15M NaCl, pH 8.5, at room temperature (RT) to remove the acetone. 4 mg of Hp1 (Sigma) diluted to 1 mg/ml in borate buffer, and 50 mg Hpr synthetic peptide diluted to 12.5 mg/ml in borate buffer were each added to 5 ml of gel and incubated with agitation at 4° C. for 30 hr. After incubation, the supernate was decanted and an equal volume of 0.2M Tris was added to quench any remaining reactivity. The gels were then extensively washed with Tris-saline buffer. The Hpr peptide column was then denatured with 100 ml of 0.1% $NaDodSO_4$ in Tris-saline buffer.

Anti-Hpr antibodies reactive with the Hpr peptide were isolated from the crude anti-PAPP-A serum by means of sequential affinity chromatographic steps. First, 100 ul of crude anti-PAPP-A antibody in 10 ml Tris-saline buffer was incubated with the Hp1 gel overnight at 4° C. with agitation. The gel was next washed extensively with Tris-saline and the flow-through collected over a 5 ml hydroxyapatite column. Antibodies reactive with the Hp1 column were eluted with 20 ml of acetate buffer (0.05M sodium acetate, 0.15M NaCl, pH 3.5, at room temperature). The antibodies which flowed through the column were eluted from the hydroxyapatite column with 20 ml of 0.4M sodium phosphate. Both sets of antibodies were dialyzed against 2 l of Tris-saline buffer.

The antibodies unreactive with the Hp1 column were then incubated with the denatured Hpr peptide gel overnight at 4° C. with agitation. Antibodies reactive with the Hpr peptide were eluted with 20 ml of acetate buffer and dialyzed against Tris-saline. Each of these antibody fractions were used to label immunoblots of 10–15% gradient Laemmli gels on which the subunits of haptoglobin 1 and the haptoglobin-type protein from pregnancy serum (according to Example 1) were separated by electrophoresis.

Figure 6:
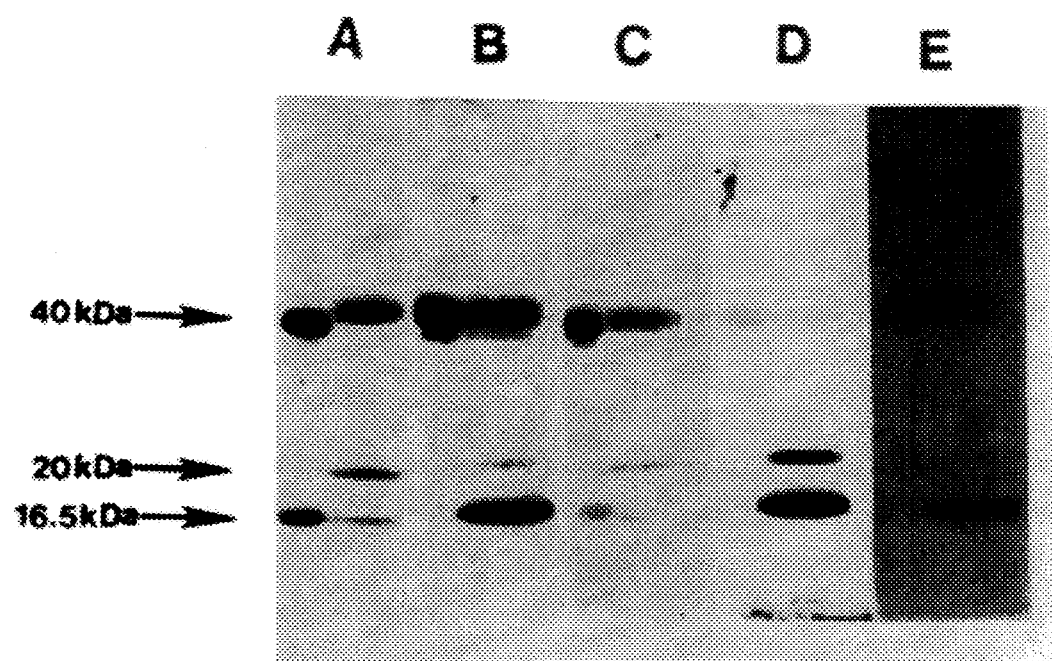
FIG. 6, parts A–E shows polyacrylamide gel electrophoresis of haptoglobin 1 and hpr gene product. Panels B–E are immunoblots of the same proteins with various antibody preparations.

FIG. 6, panel A shows a Coomassie stained 10–15% gradient Laemmli gel of 25 ug Hp1 in the left lane, and 100 ug Hpr protein on the right. Panels B–E are immunoblots of the same protein loads. Panel B was incubated with unabsorbed anti-PAPP-A antibody, 1:50. Panel C was incubated with the subset of anti-PAPP-A antibodies which bound to immobilized Hp1; panel D was incubated with the unreactive antibodies which flowed through. Note the enrichment for antibodies to the 40 kDa beta chains which bound to the Hp1 gel in panel C; while antibodies to the unique immunoreactive alpha-chain were unreactive with immobilized Hp1 and flowed through (panel D). Panel E was incubated with the subset of antibodies seen in panel D which reacted with immobilized, denatured, synthetic Hpr peptide. Note that these antibodies, which bound to the synthetic Hpr peptide, react only with the 16.5 kDa alpha chain of the pregnancy serum associated haptoglobin-type protein. This demonstrates that the unique alpha-chain of this protein contains Hpr epitopes.

Example 6

This example shows that Hpr epitopes are identified in the cytoplasm of human breast carcinoma.

Paraffin embedded human breast carcinoma specimens were obtained from the files of the Department of Pathology of the Johns Hopkins Hospital. Buffered 10% formalin-fixed, paraffin embedded 6 u tissue sections were deparaffinized in xylene, and rehydrated in alcohol-water baths, then incubated in Tris-saline at pH 7.6, followed by blocking of endogenous peroxidase activity with 3% $H_2O_2$ for 15 min. After Tris-saline washes, sections were blocked with normal swine serum diluted 1/100 (Dako) for 30 min, followed by incubation with specific antibody or non-immune serum overnight at 4° C. After washing in Tris-saline, swine-anti-rabbit immunoglobin IgG fraction (Dako), 1/100 in 0.5M tris buffer was applied for 30 min, followed by a peroxidase-rabbit-anti-peroxidase complex (Dako). After final washing, the slides were incubated with diaminobenzidine (Sigma) substrate for 6 min, counterstained in Mayer's hematoxylin, coverslipped, and examined.

Antibodies were raised against Hpr protein by immunization of rabbits with the 34-mer synthetic peptide described above in Example 5. For purposes of immunization, the peptide was conjugated to keyhole limpet hemocyanin (KLH) (Boehringer Mannheim) essentially as described (Lerner, et al., Proc. Natl. Acad. Sci. USA, vol. 78, pp. 3403–3407, 1981). 8 ul of an 8.75 mM solution of malemidobenzoyl-hydroxysuccinimide (MBS) (Pierce Chemical Co. ) in dimethyl formamide were added to 14.8 mg of KLH in phosphate-buffered saline and incubated at room temperature for 30 min. The KLH-MBS conjugate was separated from unreacted MBS by gel filtration on a Pharmacia PD-10 column. 1.2 mg of Hpr peptide was added directly to the KLH-MBS and mixture incubated a further 30 min at room temperature. To estimate coupling efficiency, a 35 ul sample of the unfractionated 3.0 ml reaction volume was chromatographed on a Pharmacia Superose 12 column using a Waters HPLC at 1 ml/min in PBS and the effluent monitored at 214 nm. Unreacted peptide was quantified by peak integration and comparison to standards of peptide run alone. This method yielded an approximate substitution ratio of 4.6 peptides per KLH molecule.

Two Pasteurella-free New Zealand White rabbits (Dutchland) were each inoculated on Day 0 with 200 ug of antigen in 1 ml of an emulsion comprised of equal parts of phosphate buffers saline (PBS) and complete Freund's adjuvant; the inoculae were divided among 3–4 subcutaneous and intramuscular sites. On Day 14, the animals were boosted with similar mounts of antigen in incomplete Freund's adjuvant. The rabbits were test bled on Day 32; serum from the positive rabbit was collected over the ensuing month.

Bovine serum albumin was derivatized with the synthetic Hpr peptide as described above. An enzyme-linked immunosorbent assay was performed as described by (Voller et al., J. Clin. Pathol., vol. 31, pp. 507–520, 1978) using 2 ug of BSA-peptide per well which was tested against dilutions of rabbit serum and developed with protein A-horseradish peroxidase conjugate and o-phenylene-diamine substrate.

To purify the antibody, a 10 cm×5 mm SELECTISPHER-10 activated tresyl column HPLC affinity column (Pierce Chemical Co.) was derivatized with the Hpr synthetic peptide. The column was washed with 30 ml PBS at a flow rate of 2 ml/min, then 27 mg of peptide dissolved in 4.5 ml of PBS was passed through the column at a flow rate of 1 ml/min. Unreacted tresyl groups were capped by passing 30 ml of 0.2M Tris HCl, pH 8.0 through the column. For antibody purification, the column was equilibrated in 300 mM NaCl, 20 mM sodium phosphate, pH 7.5 at room temperature. 10–20 ml serum were loaded onto the column at a flow rate of 0.5 ml/min. After loading, the column was washed with buffer until the optical density of the effluent at 280 nm returned to zero. Antibody was then eluted with 6M urea in the same buffer, and the antibody-containing fractions immediately dialyzed into Tris-buffered saline containing 1 mM $NaN_3$.

Figure 7:
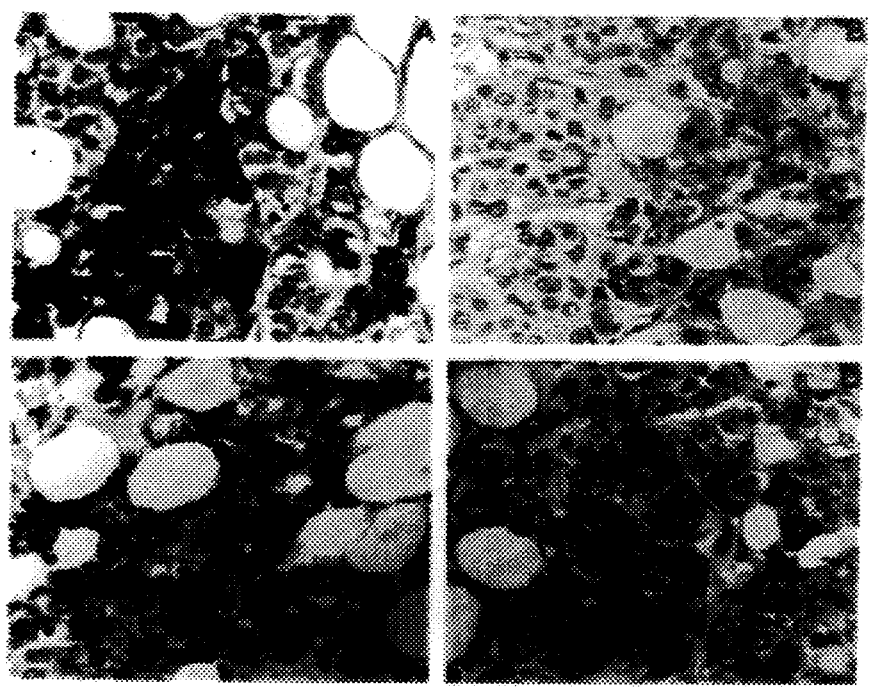
FIG. 7, parts A–D Panel A shows immunohistochemical staining of human breast cancer cells using antibodies raised against a synthetic peptide whose sequence corresponds to the hpr gene. Panel B shows the same experiment except that the antibody was pre-incubated with purified Hpr protein from pregnancy serum. Panel C shows staining with anti-CEA, which was not abolished by preincubation with Hpr protein (Panel D).

FIG. 7 illustrates immunoperoxidase staining of a primary breast adenocarcinoma with both anti-Hpr antibody (Panel 7a) and anti-CEA antibody (Panel 7c); note the intense cytoplasmic positivity of anti-Hpr staining. When anti-Hpr antibody was incubated for 2 hr at 4° C. with native Hpr protein, positive cytoplasmic staining was abolished (Panel 7b). To establish specificity of the immunoabsorption, anti-carcinoembryonic antigen (CEA) antibodies were incubated under similar conditions with native Hpr protein. The cytoplasmic CEA positivity was not abolished by such pre-incubation with Hpr protein (Panel 7d). Together with the failure of Hp1 and Hp2 to inhibit staining, this establishes that epitopes derived from the N-terminus of the predicted alpha chain of the hpr gene product can be detected in human breast carcinoma. Thus Hpr protein, a modified form of Hpr, or a highly cross-reactive protein must be present in human breast carcinoma cells.

Example 7

This example demonstrates that there is a correlation between expression of a protein cross-reactive with the hpr gene product by human breast cancer and the time interval that a patient remains disease-free.

Sixty-one cases of human breast cancer were available for concurrent evaluation of cancer-related antigen expression and immunoreactivity with anti-PAPP-A antiserum. Expression of a protein cross-reactive with the hpr gene product was evaluated by immunohistochemical staining of paraffin-embedded material using affinity-purified polyclonal antibody to a synthetic peptide whose sequence was derived from the hpr gene sequence. PAPP-A positivity was similarly evaluated using anti-PAPP-A antiserum. Of the 61 patients, 40 had Stage I disease (tumor less than 5 cm, negative lymph nodes) and 21 had Stage II disease (tumor less than 5 era, positive axillary lymph nodes). Data were analyzed in a life table format using the BMDP Statistical Program. Two statistical tests, the Generalized Wilcoxon (Breslow), and the Generalized Savage (Mantel-Cox) were used to determine the significance of the differences between curves.

Figure 8:
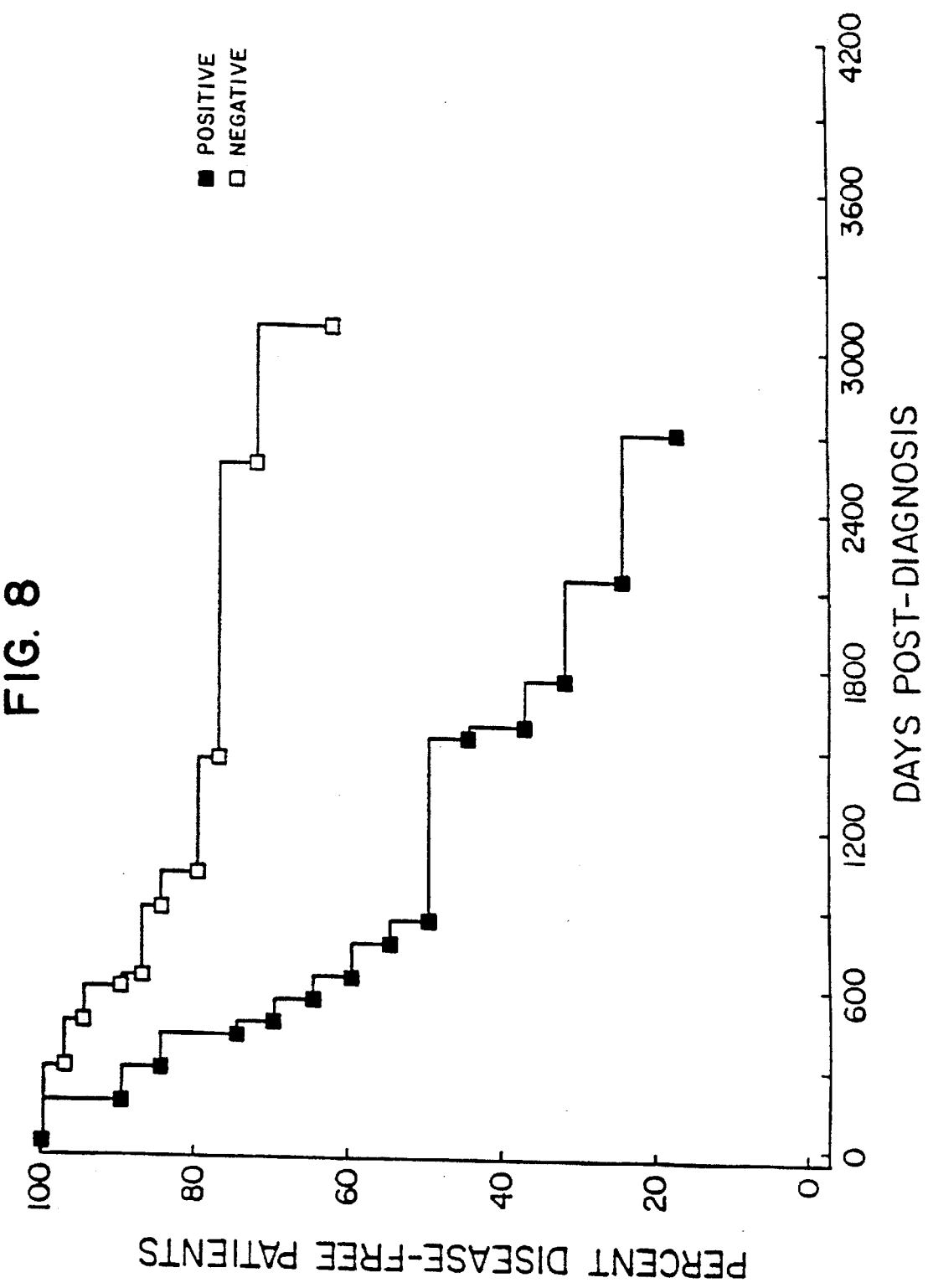
FIG. 8 shows the correlation of immunochemical staining using Hpr-specific antibodies with relapse of breast cancer.

The results are shown in FIG. 8. The ordinate shows the percentage of patients remaining disease-free, while the abscissa shows the time interval since diagnosis. The differences between the curves are highly significant, with p less than 0.0005 (Wilcoxon) and p less than 0.0003 (Savage).

Example 8

This example demonstrates that cultured breast cancer cells express a protein cross-reactive with the hpr gene product.

Although fresh human breast carcinoma can be used as a source of a protein cross-reactive with the hpr gene product, the quantities are generally small, and availability is irregular. For these reasons, a series of human breast carcinoma cell lines were obtained from the American Type Culture Collection (Rockville, Md.) and screened for expression of a protein cross-reactive with the hpr gene product by an immunohistochemical procedure. FIG. 9 shows the results of this approach in one such line, MDA-MB-231, an estrogen receptor negative cell line (Anderson, J. Submicroscop. Cytol., vol. 16, pp 673–690, 1984).

Briefly, cells were grown on chamber slides in L-15 medium supplemented with 10% fetal bovine serum and antibiotics, fixed in paraformaldehyde, permeabilized with Triton X-100, incubated with anti-Hpr 40 ug/ml, or controls overnight at 4° C., and developed sequentially with a biotinylated secondary antibody, avidin-peroxidase, and aminoethyl-carbazole-peroxide substrate solution.

Figure 9A:
FIGS. 9A and B show the staining of a breast cancer cell line with antibody raised against a synthetic peptide made according to the sequence of the hpr gene.
Figure 9B:

FIG. 9A shows granular cytoplasmic staining by the specific antibody, while FIG. 9B shows the control without primary antibody; unrelated affinity-purified antibodies stain with appropriate distributions when used as unrelated positive primary antibody controls in this method. Thus, it can be readily seen that these cultured cells can produce a protein which is cross-reactive with the hpr gene product.

Example 9

This example shows that decidua tissue synthesizes a protein which is cross-reactive with the hpr gene product under physiologic conditions.

Because a protein which is cross-reactive with a peptide according to SEQ ID No. 1 is purified from pregnancy serum, pregnancy-specific tissues were screened immunohistochemically for expression. Fresh decidua was obtained from tissues otherwise to be discarded following elective abortions and was formalin-fixed. Buffered 10% formalin-fixed, paraffin embedded 6 u tissue sections were deparaffinized in xylene, and rehydrated in alcohol-water baths, then incubated in Tris-saline at pH 7.6, followed by blocking of endogenous peroxidase activity with 3% $H_2O_2$ for 15 min. After Tris-saline washes, sections were blocked with normal swine serum diluted 1/100 (Dako) for 30 min, followed by incubation with specific antibody made as described above in Example 6, or for control, with nonimmune serum overnight at 4° C. and developed sequentially with a biotinylated secondary antibody, avidin-peroxidase, and aminoethyl-carbazole-peroxide substrate solution. The slides were incubated with diaminobenzidine (Sigma) substrate for 60 min, counterstained in Mayer's hematoxylin, coverslipped, and examined.

The results of decidual staining are seen in FIG. 10. FIG. 10A shows the prominent cytoplasmic staining with the anti-Hpr antibody, while FIG. 10B shows a control where the primary antibody was omitted. This experiment suggests that decidua synthesizes a protein cross-reactive with the hpr gene product under physiologic conditions.

Example 10

This example demonstrates that a protein cross-reactive with the hpr gene product expressed by decidua is synthesized as a larger polypeptide than Hpr protein isolated from pregnancy serum.

Figure 11:
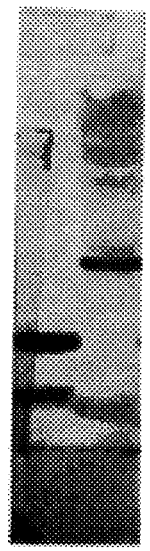
FIG. 11 depicts a Western blot analysis of reactive proteins in human decidua using polyclonal antibodies raised against the synthetic peptide made according to the predicted sequence from the hpr gene.

FIG. 11 shows that anti-Hpr recognizes an unexpectedly heavy alpha chain in lysates of decidua. Briefly, 1 g of frozen decidua was homogenized in 10 ml of lysis buffer (10 mM Tris HCl, pH 7.5 at 4°, 1 mM EDTA, 1% TRITON X-100 (a polyoxyethylene ether non-ionic surfactant) 0.5 mM diisopropylfluorophosphate) using a Brinkmann polytron. Insoluble material was removed by centrifugation at 1200 x g for 5 min at 4° C., and the resultant supernate mixed with Laemmli solubilizing buffer. A 50 ul aliquot was electrophoresed on a 10–15% polyacrylamide gel, then transferred to nitrocellulose using a semi-dry blotting apparatus (Polyblot, American Bionetics). The blot was blocked for 2 h at room temperature with 3% BSA in Tris-saline, then incubated overnight in anti-Hpr, 40 ug/ml in Tris-saline. Following incubation, the blot was then sequentially washed in PBS with 0.05% TRITON X-100, incubated with biotinylated goat-anti-rabbit IgG, washed, incubated with avidin-horseradish peroxidase complex, washed, and incubated in aminoethylcarbazole substrate solution.

The blot shows that decidual lysate contains a unique alpha chain species. The left-hand lane shows a partially-purified preparation which is contaminated with haptoglobin 2; the anti-Hpr used in this experiment cross-reacts with haptoglobin 2 alpha chain, the uppermost band, but fails to react with haptoglobin 1 alpha chain. The lower band in the left-hand lane represents Hpr alpha chain from a protein cross-reactive with the hpr gene product. The right-hand lane shows that the decidual lysate contains a prominent immunoreactive band in the approximately 30 kDa range.

In liver, haptoglobins are synthesized as a single, contiguous polypeptide chain which is proteolytically cleaved to form the alpha and beta chains. Reaction of the blot with a polyvalent anti-haptoglobin antibody detected a single 45 kDa species. No mature alpha or beta chain was detected.

Example 11

Purification of OA-519 Protein from Cell Lysates

Figure 12A:
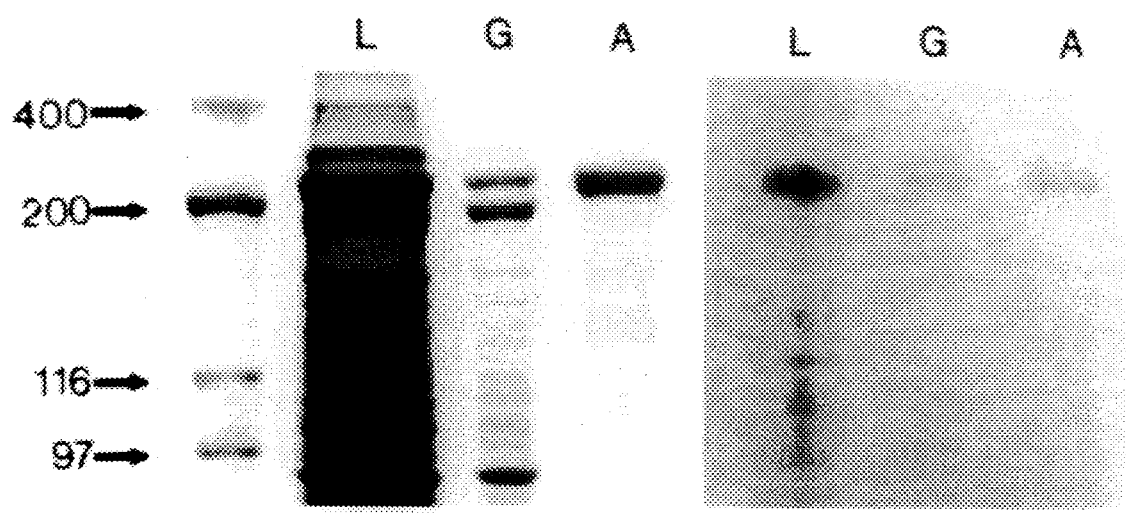
FIG. 12A depicts progressive purification of OA-519 from breast carcinoma. Polyacrylamide gel electrophoresis and corresponding Western blots are shown of sequential chromatographic purification of cytoplasmic proteins reactive with purified polyclonal anti-Hpr antibodies.

Purification of a protein which is cross-reactive with the hpr gene product from breast cancer cells is demonstrated in FIG. 12A. The Figure shows 4–8% gradient gel SDS PAGE of a protein preparation in various stages of purification. The right hand panel is stained with Coomassie Blue, and the left hand panel is a Western blot using anti-Hpr polyclonal affinity purified antibody.

ZR-75-1 human breast carcinoma cells were grown to near confluence in medium. Confluent monolayers were rinsed with phosphate-buffered saline, then scraped free, harvested by centrifugation, and stored frozen.

To each aliquot of approximately $1.5 \times 10^7$ cells, 10 ml of purification buffer (20 mM Tris HCl, pH 7.5 at 4°, 1 mM EDTA, 0.1 mM diisopropylfluorophosphate, 0.1 mM phenylmethylsulfonyl fluoride) was added. Cells were homogenized with 10 strokes of a Dounce homogenizer, then clarified supernate was obtained by centrifugation at 16,000 x g for 30 min. at 4° C. (Lane L of FIG. 12A was loaded with clarified ZR-75-1 hypotonic lysate.)

A Sephacryl S-200 (Pharmacia) gel filtration column, 2.5×90 era, was pre-equilibrated with purification buffer, pH=8.0, containing 1 mM b-mercaptoethanol and 100mm KCl. ZR-75 lysate was filtered through 0.45 mM filter, then loaded onto column at 25 ml/h. Fractions were analyzed for presence of 270,000 Da polypeptide by SDS-PAGE using a 4% Coomassie-stained gel. Presence of the polypeptide may optionally be confirmed by using Western blotting with either polyclonal antibody specific for peptide according to SEQ ID NO. 1 or anti-270 kDa protein, developing the blots with $^{125}$I-protein A. (Lane G of FIG. 12A was loaded with pooled fractions from the gel filtration column.)

Positive fractions from the Sephacryl column were pooled, diluted with an equal volume of purification buffer plus 1 mM B-mercaptoethanol then loaded onto a pre-equilibrated Mono-Q HR 5/5 anion exchange HPLC column (Pharmacia). At a flow rate of 1 ml/min., the column was washed with 15 ml of purification buffer plus 1 mM B-mercaptoethanol, eluted with linear 60 ml gradient over 60 min. to a final 1M KCl concentration, then washed with 5 ml of 1M KCl-containing purification buffer plus 1 mM b-mercaptoethanol. Fractions containing the polypeptide were selected by SDS-PAGE using Coomassi-stained 4% gels. (Lane A in FIG. 12A was loaded with pooled fractions from the anion exchange column.) Fractions containing purified polypeptide, designated OA-519, were pooled and further processed according to downstream experimental needs. Characteristic yields were roughly 1 mg of OA-519 per $2 \times 10^7$ cells with purity of 98% or greater.

Example 12

Sequences of Peptide Fragments from 270 kDa Cytoplasmic Protein

Sequences were obtained by: (1) purification of 270 kDa polypeptide according to Example 11; (2) dialysis into 100 mM ammonium bicarbonate, pH 7.8 and proteolytic cleavage by endoproteinase Glu-C (Staphylococcal V8 protease); (3) isolation of peptides by reversed phase chromatography in a 20 mM potassium phosphate, pH 7.8, buffer system with elution by linear gradient to 60% $CH_3CN$/40% phosphate buffer; (4) rechromatography on reversed phase using 0.1%. trifluoroacetic acid in water and 0.1% trifluoroacetic acid in $CH_3CN$ to elute peptides; (5) quantitation and estimation of purity through amino acid analysis; and (6) determination of peptide sequence through automated Edman degradation on an Applied BioSystems gas phase sequencer. Sequences from five separate peptides are provided in the following Table 1:

TABLE 1

Peptide Sequences for OA-519 Fragments

| Peptide Sequences | Peptide Identifier |
|---|---|
| faalqee | OA51901.SEQ, May 22, 1991 Peptide C |
| hpesptpnpteplflaqae | OA51902.SEQ PEPTIDE K |
| havvle | OA51903.SEQ, June 12, 1991 PEPTIDE F |
| raalqe | OA51904.SEQ, June 12, 1991 PEPTIDE B2 MAJOR SEQUENCE |

A final hydroxyapatite chromatography step was added to achieve more than 99% purity using a Bio-Rad MAPS Analytical HPHT Cartridge. Using a 0–600 millimolar phosphate gradient, OA-519 elutes in one peak at 200 millimolar phosphate.

Purified OA-519 was dialyzed into 50 millimolar ammonium bicarbonate, pH 8.0 and proteolytically cleaved with a 1:50 dilution of endoproteinase glutamate C (V8 protease) for 15 minutes at 37° C. The peptides were subjected to SDS-PAGE on 4% Laemmli gels and transferred to PVDF membranes (BioRad), and were sequenced directly from the PVDF membrane using automated Edman degradation on an Applied BioSystems gas phase sequencer (Matsudaira, P. T., "A Practical Guide To Protein and Peptide Purification for Micro-Sequencing", Academic Press, New York, 1989).

Limited proteolytic cleavage generated two major peptides of approximately 150 and 134 kD. The 150 kD peptide had a blocked N-terminus and thus represented the N-terminal OA-519 peptide. N-terminal sequence was obtained from the 134 kD internal peptide which demonstrated 84.6% homology with rat fatty acid synthase over 13 amino acids as seen in FIG. 12B. Thus, OA-519 has structural homology with fatty acid synthase, also an approximately 270 kD molecule.

Example 12A

OA-519 has Fatty Acid Synthase Activity

Purified OA-519 from the ZR-75-1 human breast carcinoma cell line has fatty acid synthase activity based on its ability to incorporate acetyl coenzyme A and malonyl coenzyme A into fatty acids in the presence of NADPH. This reaction is specific for fatty acid synthase. (Wakil, S. J., Biochemistry, 28:4523–4530, 1989). Fatty acid synthesis by OA-519 was demonstrated by incorporation of $^{14}C$ malonyl coenzyme A into fatty acids, subsequent esterification of the fatty acids, and analysis by reversed-phase thin layer chromatography.

Incorporation of $^{14}C$ malonyl coenzyme A into fatty acids by OA-519:

OA-519 was purified as in Example 12 except that protease inhibitors were omitted as they interfere with the final step of the synthase assay. 4.2 ug of OA-519 in 20 ul of 20 millimolar Tris HCl, 270 millimolar KCl, 1 millimolar EDTA, 1 millimolar DTF, pH 7.5 at 25° C. was added to the following reaction mixture: 75 nanomoles NADPH; 25 nanomoles acetyl coenzyme A; 16.6 ul of 1 molar potassium phosphate, pH 6.6 at 25° C.; and 97 ul HPLC grade water to a total volume of 150 uL. The reaction mixture was vortexed and 5 ul of $^{14}C$ malonyl coenzyme A (20 uCi/ml; 51 mCi/millimolar) and 25 nanomoles malonyl coenzyme A were added. Following vortexing, the reaction mixture was incubated at 37° C. for 20 minutes and stopped by the addition of 1 ml of 1:1 chloroform:methanol.

Methyl esterification of $^{14}C$ fatty acids:

Prior to thin layer chromatographic separation of the $^{14}C$ fatty acid mixture, methyl esters of the $^{14}C$ fatty acids were prepared using the method of methanolic sulphuric acid. The chloroform:methanol:reaction mixture was vortexed then agitated for 30 minutes. Following centrifugation, the supernatant was dried under $N_4$. The dried lipids were extracted twice in 400 ul of hydrated n-butanol:HPLC water (1:1) pooled, washed, and dried under $N_2$. To synthesize the methyl esters, 0.75 ml of 2% sulfuric acid in methanol was added to the dried fatty acids, gassed with $N_2$, and incubated for 2 h at 70° C. Following the addition of 0.75 ml of HPLC grade water, $^{14}C$ fatty acid methyl esters were extracted twice with 1.5 ml of pentane, washed with 0.5 ml HPLC water and dried.

$^{14}C$ fatty acid methyl esters were separated and identified using reversed phase thin layer chromatography as follows. Reversed-phase thin layer chromatographic plates (20×20 cm, Analtech) were baked in a vacuum oven at 80° C. for 20 minutes. Dried $^{14}C$ fatty acid methyl esters and standards were resuspended in 20 ul chloroform:methanol (9: 1), spotted, and chromatographed in chloroform: methanol:water (5:15:3). Non-radioactive standards were visualized with cyclodextrin spray in iodine vapor. $^{14}C$ fatty acid methyl esters were detected using a Bioscan System 2000 imaging scanner with Autochanger 3000.

Results:

OA-519 synthesized 85% palmitate (16 carbon saturated fatty acid), with approximately 6% myristate and 8% stearate (14 and 18 carbon saturated fatty acids, respectively) (FIG. 12C). These data demonstrate that OA-519 has fatty acid synthase activity by showing generation of complete fatty acids from $^{14}C$-labeled malonyl-CoA. The ratios among product fatty acids is similar to fatty acid synthase from human liver, but markedly different than that for fatty acid synthase from lactating human breast (34% stearate, 33% palmitate, 16% myristate).

Kinetic Characterization of OA-519 Fatty Acid Synthase

The specific activity of purified OA-519 was determined spectrophotometrically by following the oxidation of NADPH at 340 nm in the presence of acetyl coenzyme A and malonyl coenzyme A. OA-519 has a specific activity of 586 nanomoles NADPH oxidized/min/mg protein which compares favorably with the value of 404 obtained for human liver.

Spectrophotometric studies with OA-519$_{FAS}$ demonstrated that the apparent $K_m$ of 86.2×10$^{-5}$ M for malonyl-CoA was higher than the literature values reported for rat or rabbit mammary gland (1.3×10$^{-5}$ M or 2.9×10$^{-5}$ M, respectively) (Smith, et al., Methods Enzymol., 35:65–74, 1975; Dils, et al., Methods Enzymol., 35:74–83, 1975) or for the synthase from the human breast cancer cell line SKBR3 (1.8×10$^{-5}$M) (Thompson, et al., Biochem. Biophys. Acta, 662:125–130, 1981). The $K_m$ for the purified synthase from normal human tissues has not been reported. In contrast to the $K_m$ values, the specific activity of 624 nmol NADPH oxidized/min/mg protein was similar to the reported specific activities of fatty acid synthases purified from a variety of sources including human liver (Roncari, *Methods Enzymol.*, 71:73–39, 1981).

Example 12B

Cloning of OA-519 and Determination of the Sequence of Human Fatty Acid Synthase The strategy for cloning human fatty acid synthase took advantage of the high degree of conservation among previously cloned fatty acid synthases, including rat, chicken, and murine forms, to generate probes likely to hybridize with human fatty acid synthase cDNA. Sequences were aligned by the GCG PILEUP program, similar to that described by Higgins and Sharp (*CABIOS*, 5:151–153, 1989). The aligned sequences identified an oligonucleotide probe with the sequence: 5'- ggg act gga gtc tat cat caa cat cat cca cag ctc cct ggc tga gcc tcg agt gag t -3' from a region of high homology in the c-terminal third of the aligned fatty acid synthase sequences.

Initial screening used a commercial (Stratagene) oligo-dT-primed library in lambda gt1 1 prepared using RNA from ZR-75-1 human breast carcinoma cells, a line which produces moderately high levels of fatty acid synthase protein. Probing this commercial (Stratagene) library with an end-labeled probe having the above oligonucleotide sequence identified a 1.6 kb clone, pFAS 1.6, which contained an open reading frame corresponding by homology to the c-terminus and 3' untranslated regions of fatty acid synthase mRNA. Analysis of the pFAS 1.6 sequence identified an oligonucleotide probe from its 5' region with the sequence: 5'- aac aac cac cct ctg ggc atg gcc ate ttc ttg aa -3'. Reprobing the ZR-75-1 library with an end-labeled probe having this second oligonucleotide sequence yielded an overlapping clone, pFAS 3.0, which by homology to known sequences encoded in its open reading frame a further portion of the fatty acid synthase molecule.

Analysis of the 5' regions of pFAS 3.0 identified a third oligonucleotide with the sequence: 5'- aga act cca tac cta gca ggc tgt c -3' which was used to construct a specifically primed cDNA library. This third oligonucleotide primed reverse transcriptase-catalyzed cDNA synthesis from poly-A RNA from SKBr3 human breast carcinoma cells, a line which synthesizes extremely high levels of fatty acid synthase. The resultant cDNA was cloned into lambda Ziplox (BRL) and screened with a 1.4 kb BamHI restriction fragment from the 5' end of pFAS 3.0 labeled by random priming; a 2.2 kb cDNA clone, pFAS 2.2, was identified. The ends of pFAS 2.2 encoded open reading frames homologous to further 5' regions of known fatty acid synthases. Rescreening of the specifically primed library with pFAS 2.2 labeled by random priming yielded two additional clones of 3.1 ,and 4.6 kb, designated pFAS 3.1 and pFAS 4.6, respectively.

All clones were subcloned into pBluescript and sequenced along both strands by the $^{35}$S/dideoxynucleotide method using the USB sequenase kit. Sequences were extended by standard methods including nested deletions and use of synthetic oligonucleotide sequencing primers. Together, these overlapping clones encode the complete human fatty acid synthase coding region as well as most of the 5' and 3' untranslated regions.

Figure 12D:
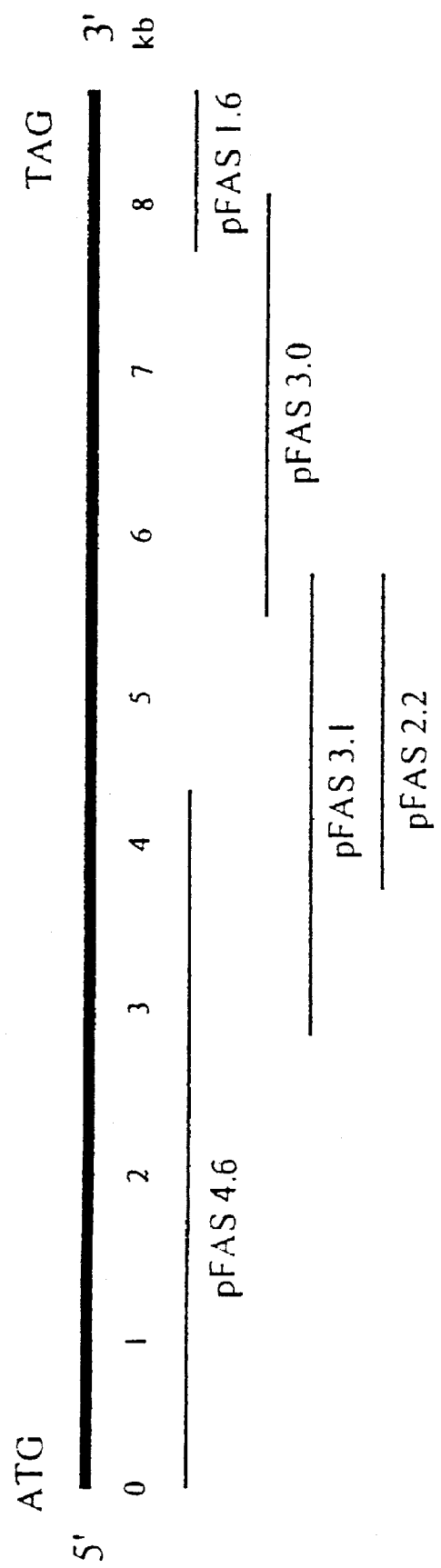
FIG. 12D shows the clone map of OA-519.

A clone map of the various clones which together encode OA-519 is shown in FIG. 12D. Cloned plasmids pFAS 1.6, pFAS 3.0, pFAS 2.2, and pFAS 4.6 were deposited with the American Type Culture Collection (ATCC), 12301 Parklawn Drive Rockville, Md. 20852, U.S.A. on Jan. 21, 1994, under ATCC Accession Nos. 75643, 75645, 75644, and 75646, respectively. A DNA molecule encoding the entire sequence of OA-519 can be assembled from these clones using standard techniques, and RNA molecules encoding all or part of the sequence prepared from expression vectors containing all or part of the DNA sequence.

Example 13

Purification of Anti-OA-519 Polyclonal Antibody

Polyclonal Antibody Production

Rabbits were inoculated subcutaneously on day 0 with 200 μg of OA-519, produced as described in Example 11, in an emulsion composed of equal parts OA-519 in buffered saline and Freund's complete adjuvant. On day 14, the rabbits received booster inoculations containing the same amount of antigen in a similar mixture prepared with incomplete Freund's adjuvant. Serum was obtained on day 30 with a similar schedule maintained thereafter. reparation of OA-519 Affinity Column 2.5 mg of purified OA-519 at approximately 0.83 mg/ml was dialyzed into 50 mM ammonium bicarbonate, 150 mM NaCl, pH 8.5 at 4° C. The OA-519 was coupled to 2 ml of Reacti-Gel 6X (Pierce) for 45 hrs., achieving 98% coupling efficiency by BCA protein microassay (Pierce). Excess reactive sites on the Reacti-Gel were blocked by incubation with 2 ml of 100 mM Tris-HCl, pH 8.2, at 4° C., overnight.

Affinity Purification of Polyclonal OA-519 Antibody

Before running, the affinity column was cycled sequentially with 10 column 10 volumes of phosphate buffered saline (PBS) with 1 mM sodium azide, pH 7.5, followed by the same buffer with 6M urea, and finally, PBS/1 mM sodium azide. For each run, 5 ml of serum was diluted 1:2 with PBS/1 mM sodium azide, and pumped on the column at 0.25 ml/min. The column was washed with PBS/1 mM sodium azide then eluted with PBS containing 6M urea. Eluted fractions were dialyzed exhaustively against PBS/1 mM sodium azide. Each run produces about 100–200 ug of antibody as determined by the BCA protein microassay (Pierce).

Example 14

Purified OA-519 Reacts with Anti-Peptide Antibody and Anti-OA-519

Figure 13:
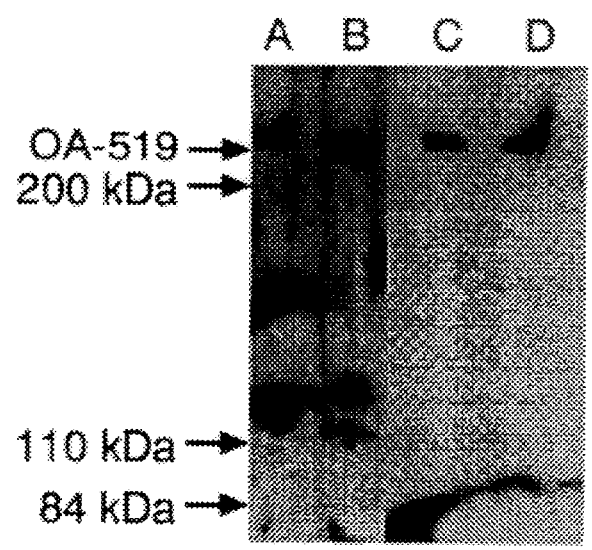
FIG. 13 depicts Western blot analysis of OA-519 using antibodies raised against the synthetic peptide (Lanes A-B) or antibodies raised against purified OA-519 (Lanes C–D).
Figure 14A:
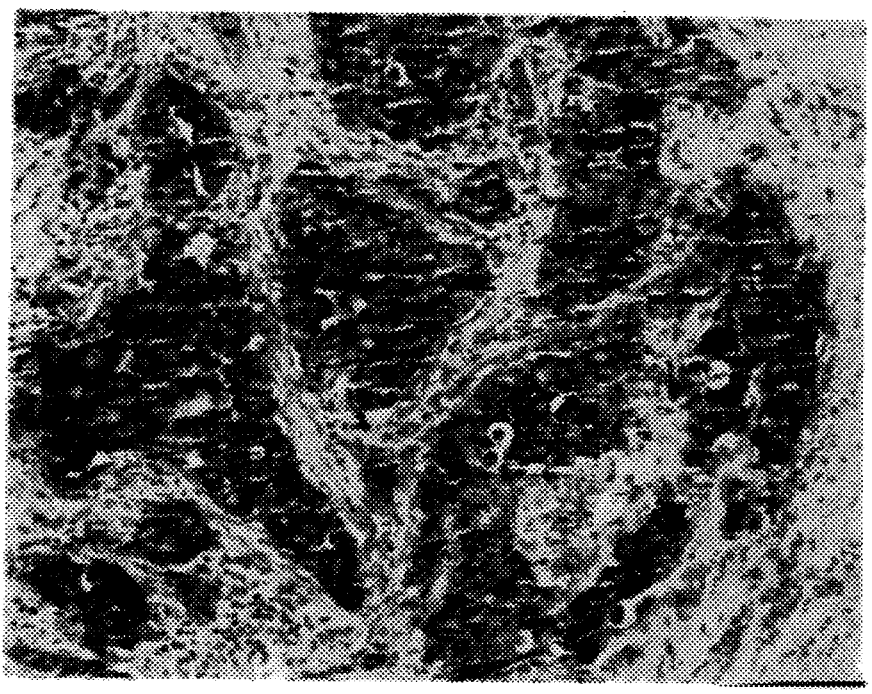
FIG. 14 shows immunohistochemical staining of human breast carcinoma using antibodies raised against purified OA-519.
Figure 14B:
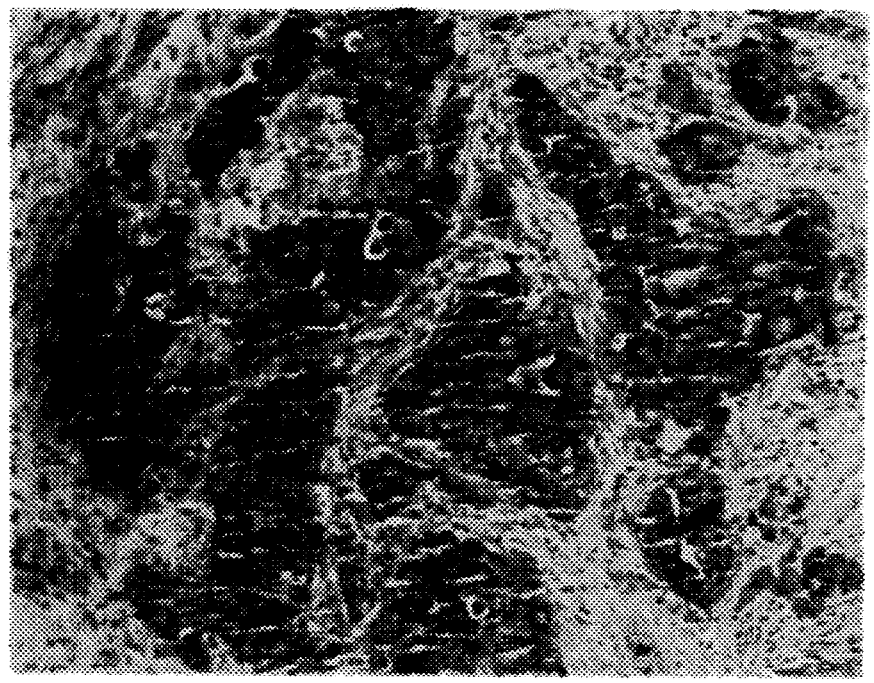

FIG. 13 represents a Western blot of a 4% Laemmli gel containing 10 ug of OA-519, purified according to Example 11, in each lane. Each lane was incubated with the indicated antibody at the specified concentration, then developed using $^{125}$I-protein A. Lane A was developed with 10 ug/ml of affinity-purified rabbit polyclonal anti-Hpr peptide antibody prepared by immunizing rabbits with a peptide according to SEQ ID NO. 1; Lane B was developed with 17 ug/ml of affinity-purified rabbit polyclonal anti-peptide antibody; Lane C was developed with 13 ug/ml of affinity-purified rabbit polyclonal anti-OA-519, according to Example 13; Lane D was developed with 20 ug/ml of affinity-purified rabbit polyclonal anti-OA-519. The dark splotches of MW below 200 kDa represent artifact.

Example 15

Identification of OA-519 in Human Breast Carcinoma Extracts

Fresh human breast carcinoma tissue was homogenized in 20 mM Tris HCl, pH 7.5 at 4°, 1 mM EDTA, 0.1 mM diisopropylfluorophosphate, 0.1 mM phenylmethylsulfonyl fluoride, then fractionated on a Sephacryl S-200 (Pharmacia) gel filtration column, 2.5×90 cm, with 20 mM Tris HCl, pH 8.0, 100 mM KCl, 1 mM b-mercaptoethanol. Fractions were analyzed by SDS-PAGE for the presence of 270 kDa species. Fractions were normalized to contain amounts of the 270 kDa species equivalent to that in a preparation of purified OA-519 according to Example 11. The normalized fractions were electrophoresed on a 4% Lammeli gel side by side with purified OA-519 and analyzed by Western blotting using either affinity-purified rabbit polyclonal anti-Hpr antibody (according to Example 6), or affinity-purified rabbit polyclonal anti-OA-519 (according to Example 13). The blot was developed with $^{125}$I-protein A. The developed blot showed that anti-Hpr peptide antibodies and anti-OA-519 antibodies both detect the equivalent 270 kDa species in an OA-519 preparation purified from a breast cancer cell line and in an extract of breast carcinoma tissue.

Example 16

Monoclonal Antibodies Against OA-519

Monoclonal antibodies were prepared according to a modification of the method described by Zola (Monoclonal Antibodies, a Manual of Techniques, Boca Raton, Fla., CRC Press, 1987, pp. 29–75). These BALB/c mice were immunized using an Hpr-derived synthetic peptide-keyhole-limpet hemocyanin conjugate (Kuhajda, et al., Proc. Natl Acad., Sci. USA, 1989, 86:1188–92; Kuhajda, et al., N. Engl. J. Med., 1989, 321:63641), and their spleens fused with the SP2 murine myeloma cell line. Only antibodies that reacted with tumor sections known to be positive with the polyclonal antibody were finally selected. The monoclonal antibody was purified from ascites by protein A-Sepharose affinity chromatography with elution by 6M urea in phosphate buffered saline (PBS). The eluate was collected and dialyzed against PBS overnight in the cold, aliquoted and stored frozen at –80° C. or lyophilized.

Hybridoma cells from this fusion, designated OA-519-M1 or HPR-2, were deposited with the American Type Culture Collection, 12301 Parklawn Drive, Rockville, Md. 20852, on Jul. 26, 1991, as ATCC Accession No. 10853.

Example 17

Staining Paraffin Tissue Sections

Antibody Solution

Monoclonal antibodies according to Example 16 were recovered from hybridoma supernate, purified by Protein A affinity chromatography and lyophilized. Deionized water was added to lyophilized antibody, to prepare 0.125 mg/ml stock antibody solution. The stock antibody should be kept frozen in aliquots at –70° C. Bovine serum albumin was not added to solutions. An appropriate volume of stock antibody was diluted 1/25 with a rinse buffer, pH=7.5, (preferably 1x Automation buffer, Biomeda #M30 buffer) for a working solution.

Tissue Slide Preparation

Tissue sections were deparaffinized and hydrated to water, and endogenous peroxidase activity was blocked with 3% $NH_2O_2$ in methanol for 20 minutes. Then the slide was rinsed 5 minutes in rinse buffer and incubated in 10% normal rabbit serum in rinse buffer for 30 minutes at room temperature.

Reaction with Monoclonal Antibody and Stain

Excess rabbit serum solution was removed, and working antibody (diluted 1/25 in rinse buffer) was added. The slide was incubated for 1 hour at 37° C., then drained and rinsed in rinse buffer. The slide was incubated in 1/200 biotinylated rabbit anti-mouse antibody (DAKO E-354) for 1 hour at 37° C. and rinsed in rinse buffer. Then the slide was incubated with avidin-linked horse radish peroxidase (Vectastain Elite Standard #PK6100) for 1 hour at 37° C. and rinsed in rinse buffer for 1 hour at 37° C. After the avidin-biotin complex formation, the slide was incubated in amino ethyl carbazole. for 7 min. (Biomeda #501) and rinsed with deionized water. Counter stain was applied (Biomeda's M-10 Aqueous Hematoxylin) and a coverslip, and the slide was observed by light microscopy.

Staining Pattern Observed by Light Microscopy.

The following is a general description of the staining patterns observed for patients whose tumor was positive for the presence of OA-519. Tumor staining was visible at the "low power objective", i.e., 100–150x. This method is roughly equivalent to reactivity in 10% or greater of the tumor cells. Patients whose breast cancers have reactivity identified only at higher magnifications or in less than 10% of the cells are not considered positive.

The pattern for positive staining was strictly cytoplasmic and often had a distinctive granular appearance. While light diffuse cytoplasmic reactivity occurred occasionally, a granular staining pattern was often visible in the setting of diffuse staining. Positive staining occasionally occurred without clear granularity. Nuclear reactivity has not been observed; if found it is indicative of artifact and must not be interpreted as a positive result.

Staining is preferably assessed in infiltrating carcinoma. Reactivity usually S varies from cell-to-cell and region-to-region of the tumor, reflecting heterogeneity. If all of the cells in a tumor show identical levels of reactivity, the result is probably not positive. When this type of diffuse staining occurs, granular staining will often not be identified and the case should not be considered positive. Some diffuse background reactivity has been noted in smooth muscle of the nipple, in some blood vessels, and in dense collagen. This nonspecific staining should not be confused with reactivity in breast carcinoma.

Anti-OA-519 Reactivity in Human Breast Carcinoma.

Figure 16A:
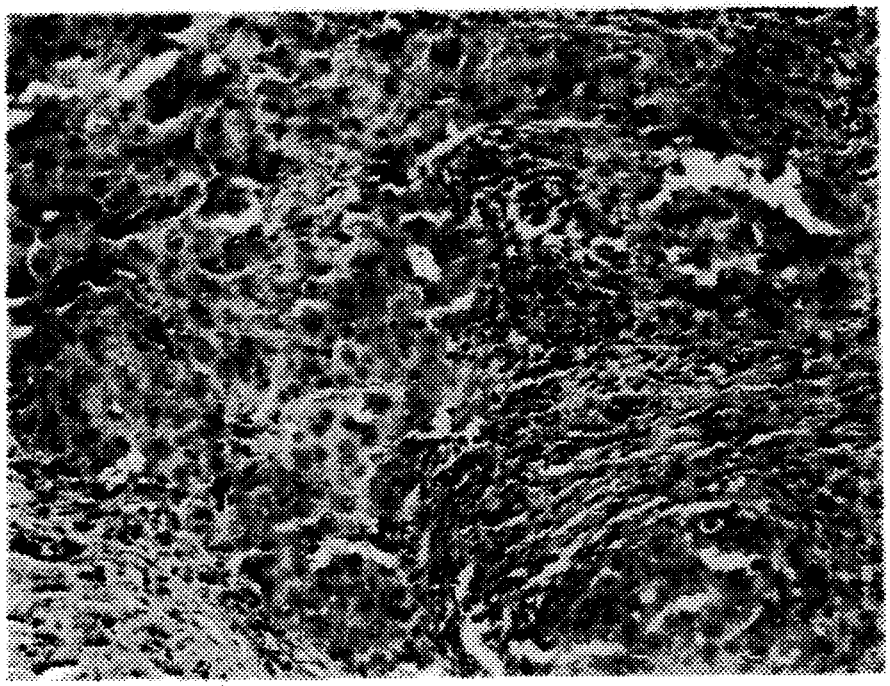
FIG. 16 shows the same experiment as FIG. 15 except the antibodies were pre-incubated with purified OA-519.
Figure 16B:
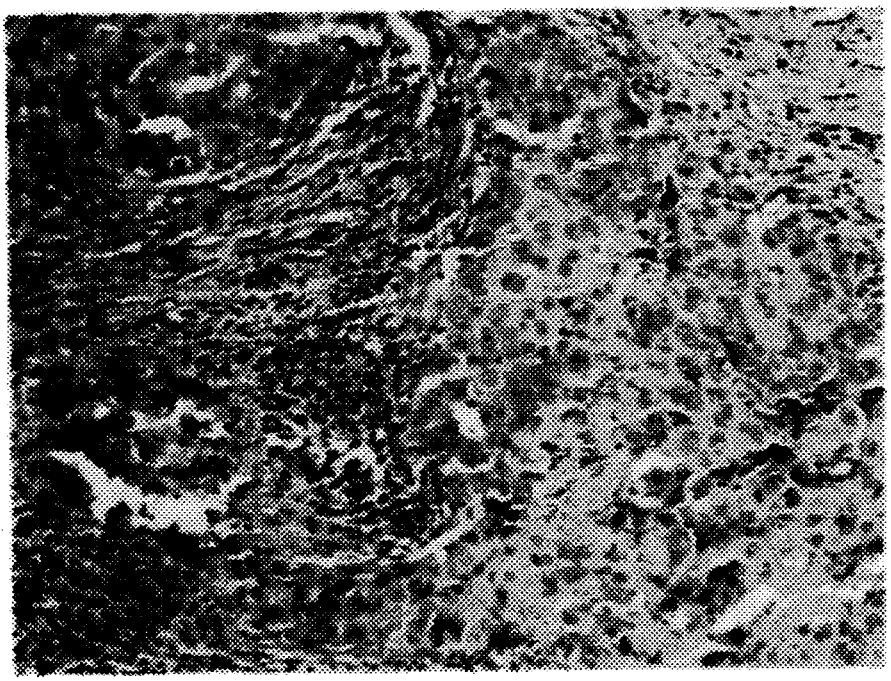
Figure 17A:
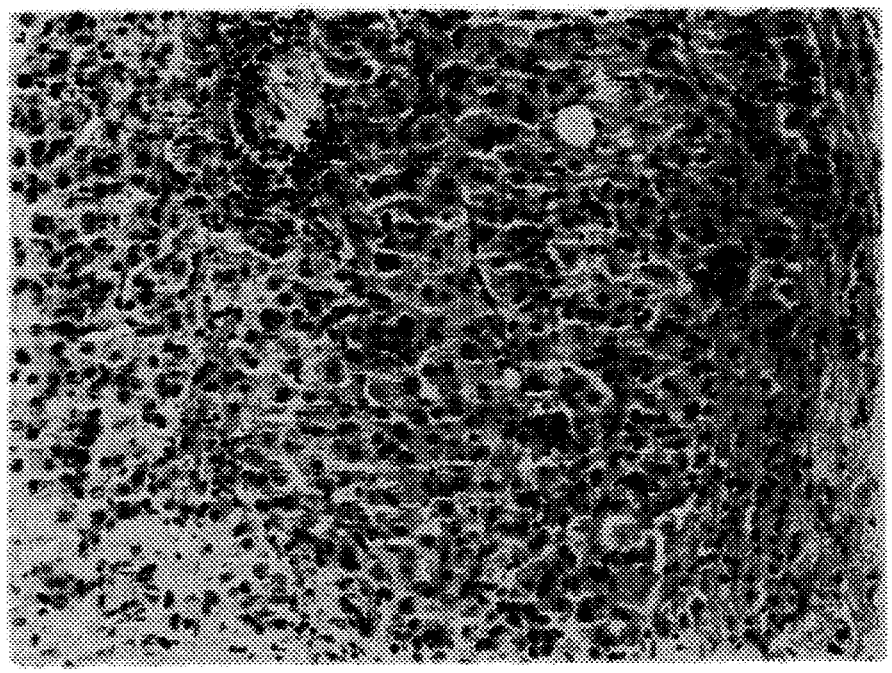
FIG. 17 is a control slide of breast carcinoma in which the primary antibody was omitted from the staining protocol.
Figure 17B:
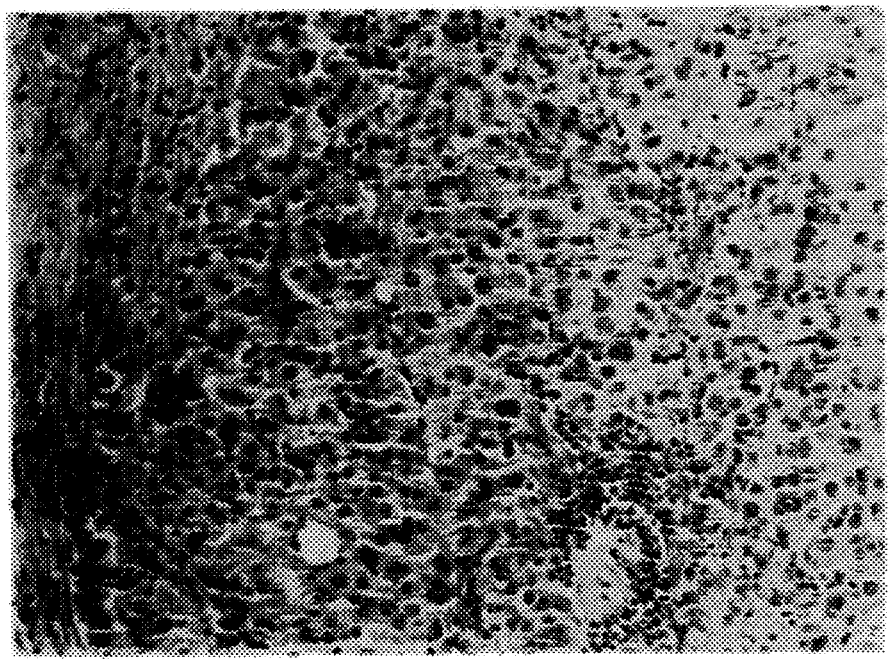

FIGS. 14–17 show histologic sections of human breast carcinoma immunohistochemically stained as described in Example 17 with various S antibodies: affinity-purified rabbit polyclonal anti-OA-519 antibody according to Example 13 (FIG. 14), affinity-purified rabbit polyclonal anti-Hpr peptide antibody according to Example 6 pre-incubated with bovine serum albumin (FIG. 15), affinity-purified rabbit polyclonal anti-Hpr peptide antibody pre-incubated with a 33-fold molar excess of OA-519 (FIG. 16), and a control slide omitting primary antibody (FIG. 17). The dark cytoplasmic staining represents immunohistochemical detection of OA-519, shown in both FIG. 14 and FIG. 15. FIG. 16 shows that pre-incubation with OA-519 ablates staining with the anti-Hpr peptide antibody, indicating the presence of a shared epitope. Pre-incubation of the anti-Hpr peptide antibody with unrelated protein (bovine serum albumin) had no effect (FIG. 15).

Example 18

OA-519 Expression is Associated with Decreased Survival in Breast Carcinoma

Breast Cancer Patient Population:

An inception cohort (patients entered into the study at the time of initial surgical treatment) of one hundred and thirtyfive women with breast cancer were identified by the Norton Hospital tumor registry, all of whom were treated with mastectomy for primary infiltrating ductal breast carcinoma. The average patient age was 52 and ranged from 32 to 72 years. The average follow-up was 12.3 years and ranged from 10 to 16 years. Patients were admitted to the study when post-surgical treatment records, cause of death, survival time, and paraffin blocks of primary tumor were available for each patient. Estrogen and progesterone receptor information was determined immunohistochemically. In addition, patient age, dose and type of chemotherapy, radiotherapy, and hormonal therapy were documented. Type of infiltrating tumor and nuclear grade were also assessed using the criteria of Fisher et al (Fisher, et al, *Cancer,* 46:908–918, 1980).

Immunohistochemical Staining for OA-519:

Immunohistochemical staining used monoclonal anti-OA-519 antibodies from hybridoma cells designated OA-519-M1 or HPR-2, which were deposited with the American Type Culture Collection, 12301 Parklawn Drive, Rockville, Md. 20852, on Jul. 26, 1991, under ATCC Accession No. HB 10853. Subsequently, additional slides from the same patients were stained with affinity-purified polyclonal antibodies prepared by immunizing rabbits with OA-519, yielding substantially equivalent results.

Briefly, the primary anti-OA-519 monoclonal antibody was incubated on the deparaffinized tissue sections at 2.5 ug/ml for 1 hour at 37° C. Following rinsing in rinse buffer, the slides were then incubated in 1/400 rabbit anti-mouse antibody (DAKO) for 1 hour. Following another rinse, the slides were incubated with avidin-linked horseradish peroxidase (Vectastain® ABC kit) for 1 hour. After the avidin-biotin complex formation, the slides were incubated in aqueous hematoxylin, coverslipped and observed.

OA-519 Immunoreactivity and Criteria for Positivity:

Positive staining was finely granular, cytoplasmic, and heterogeneous. Additionally, staining either had to be visible at 100 X magnification, or label at least 10% of tumor cells for a case to be scored positive.

Prognostic Significance of OA-519 Immunoreactivity:

Patients whose tumor-stained positively for OA-519 had a markedly increased risk of dying of breast carcinoma. FIG. 18 is a life table which shows the fate of OA-519 positive and negative patients. For example, after 12 years, about 37% of the OA-519 negative patients were dead compared to approximately 85% of the OA-519 positive patients.

The following table shows the significance of OA-519 reactivity by stage:

|         | STAGE 1<br>% dead | STAGE 2<br>% dead | STAGE 3<br>% dead |
|---------|-------------------|-------------------|-------------------|
| OA-519 + | 9/13 (70%)        | 27/31 (87%)       | 9/9 (100%)        |
| OA-519 – | 3/20 (15%)        | 16/41 (39%)       | 12/21 (57%)       |
| p-value | 0.002             | <0.0001           | 0.019             |

Comparison with Other Prognostic Markers

OA-519 expression was strongly prognostic in early breast cancer, as shown in Example 1. This prognostic potential was independent of the prognostic power of estrogen and progesterone receptors. Increased expression of OA-519 in human breast carcinoma conferred a significantly worsened prognosis as measured either by disease recurrence or overall survival. In a clinical study of 135 patients with Stage I–III breast carcinoma (Martin, et al., manuscript in preparation), Cox multi-variate proportional hazard analysis demonstrated that OA-519 and progesterone receptor expression were most strongly and independently associated with adverse survival regardless of stage (univariate relative risk 4.860, 0.070; multi-variate relative risk 2.567, 0.153, respectively).

Figure 19:
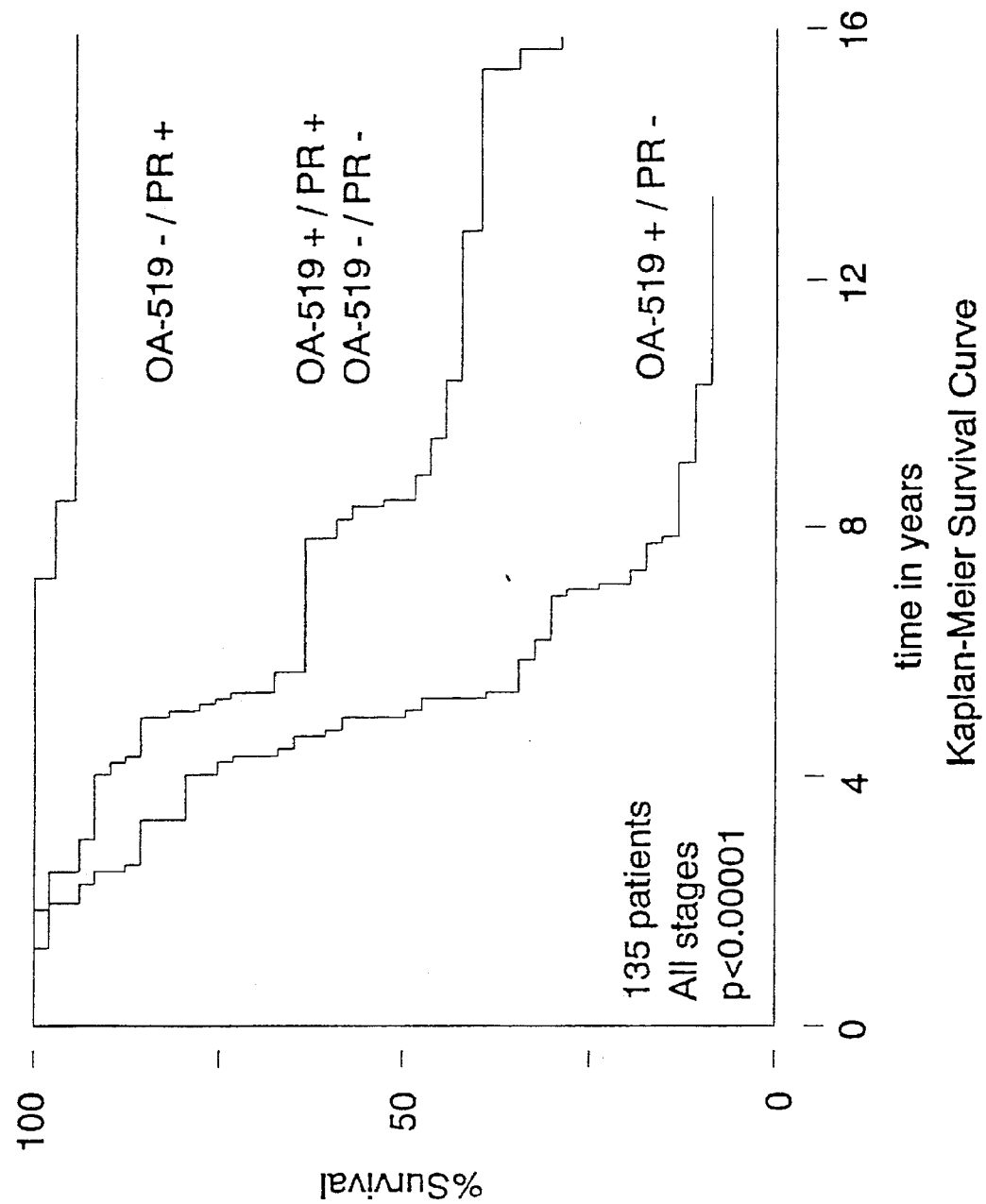
FIG. 19 shows the prognostic correlation between expression of OA-519 and progesterone receptor (PR) in breast cancer.

The prognostic power of OA-519 expression is further illustrated by the accompanying Kaplan-Meier plots (FIGS. 18 and 19). FIG. 18 demonstrates that about 10% of OA-519 positive patients survived for 15 years as compared to about 50% of OA-519 negative patients. FIG. 19 graphically demonstrates the improved prognostic stratification when the two independent prognostic markers, OA-519 and progesterone receptor, are combined. This allowed stratification of patients into an OA-519 positive, progesterone receptor negative high risk group (88% dead), an OA-519 negative/progesterone receptor positive low risk group (5.4% dead), and an intermediate risk group (63% dead).

Among other markers included in this study, OA-519 was independent of $p185^{neu}$ and cathepsin D expression. Interestingly, OA-519 expression was not associated with tumor cell proliferation as measured by proliferating cell nuclear antigen. In a separate study of OA-519 expression and S-phase determined by flow cytometry, OA-519 expression also showed no association with the S-phase fraction (Shurbaji, et al., *Lab Invest.,* 68:69A, 1993). Therefore, OA-519 expression could be utilized with the aforementioned, or any other independent prognostic marker to improve stratification of the patient population.

Example 19A

Expression of Hpr-epitopes by Prostatic Adenocarcinoma

Forty-two consecutive cases of prostate adenocarcinoma were selected from the files of the Mountain Home VA Medical Center. The specimens consisted of 23 transurethral resections (TUR), 14 needle biopsies, and five prostatectomy specimens.

Clinical Stage information was obtained from the tumor registry abstracts or by review of the clinical records.

Histopathologic Studies

Tumor grading: All slides were reviewed and a Gleason score was determined by adding the numbers for the two most predominant patterns (Gleason, in Tannenbaum M (ed): Urologic pathology: The prostate. Philadelphia, 1988, Lea & Febiger, pp. 171–198.). Gleason scores 24 were assigned Grade I, scores 5–7 were assigned grade II, and scores 8–10 were assigned Grade III.

Tumor volume estimation in TUR specimens: The method of Humphrey and Vollmer (*Hum. Pathol.,* 19:411–418, 1988) was used, and the ratio of "chips" with cancer to the total number of chips was determined, expressed as a percentage and used as a measure of tumor volume in TUR specimens.

Immunohistochemical Studies

A single representative tissue block was selected from each cancer for immunohistochemical staining.

An affinity purified polyclonal anti-Hpr peptide antibody was used in this study. This antibody was raised against a synthetic peptide corresponding to the 34 N-terminal residues of the predicted gene product (see Example 6). Staining was performed on routinely processed, formalin fixed, paraffin embedded tissue. The Avidin-Biotin Complex (ABC) immunoperoxidase technique utilizing unlabeled primary antibody was used. In brief, 6mm deparaffinized and rehydrated tissue sections were incubated in 3% hydrogen peroxide in methanol for 15 minutes to block endogenous peroxidase activity, and then in a 1:20 dilution of normal goat serum in phosphate-buffered saline (PBS) for 30 minutes. Slides were then incubated with affinity-purified polyclonal anti-Hpr peptide at 5 ug/ml in 1% bovine serum albumin (BSA) in PBS at pH 7.2 for one hour at room temperature. Alternatively, an overnight incubation at 4° C. can be used with comparable results. With intervening washes with PBS, the sections were successively incubated with biotinylated goat anti-rabbit immunoglobulin diluted 1:500 in 1% BSA in PBS (Vector Laboratories) and avidin-horseradish peroxidase complex (Vectastain®, Vector Laboratories), both for 30 minutes at 22° C. Aminoethylcarbazole (AEC) (Vector Laboratories) was used as the chromogen with Mayer's hematoxylin counterstain. For negative controls, PBS was substituted for primary antibody for each case. A known anti-Hpr positive case was used as a positive control with every run.

Staining was defined as positive for Hpr epitopes if (1) immunoreactivity was discernible at lower power (100x) (2) granular cytoplasmie staining was present without observable nuclear staining, and (3) staining was heterogeneous (i.e., the level of reactivity varied from cell to cell or from region to region. Tumors were scored as positive or negative.

Hpr Epitope Expression and Tumor Grade

Twenty (48%) of the 42 prostate cancers were positive for Hpr epitopes, while 22 (52%) were negative. No staining was noted in normal or hyperplastic prostate tissue. Hpr epitope expression occurred in 6 (67%) of nine Grade III, 14 (61%) of 23 Grade II, and in none (0%) of ten Grade I cases. The differences in the proportion of the positive staining cases was highly statistically significant when Grade I was compared to Grade II or Grade III (Fisher exact probability: p<0.002, p<0.006, p<0.0009, respectively). The difference in the proportion of positive staining cases between Grades II and III was not statistical significant.

Hpr Epitope Expression and Tumor Volume

Twenty-three TUR specimens were included in this study. Of these, eleven (48%) stained positive for Hpr epitopes, while 12 (52%) were negative. The similarity of the proportion of positive cases to that of the entire group was striking, and provided further assurance that this is representative group. Tumor volume was estimated in all of these TUR specimens by the ratio of chips with cancer to the total number of chips examined (Humphrey and Vollmer). The mean percent of "chips" with tumor in the positive group was 57% (range:2–100), while that in the negative group was 15% (range:1–75%). The difference between the two means was highly statistically significant (t=2.9, p=0.004).

Hpr Epitope Expression and Clinical Stage

The specimens examined in this study consisted of 12 Stage A, 13 Stage B, five Stage C, and 12 Stage D cancers. A clear trend towards a higher proportion of positive cases with advancing clinical stage was observed. Only 25% of Stage A cases expressed Hpr epitopes with 46%, 60% and 67% for Stages B, C, and D, respectively. These differences were not, however, statistically significant.

Hpr epitopes are expressed by some prostate cancers, and expression of these epitopes is not seen in normal or benign hyperplastic prostate tissues. There is a statistically significant correlation between Hpr-epitope expression and higher tumor grades and larger tumors. In addition, the proportion of tumors expressing Hpr-epitopes tends to increase with advancing clinical stage. Since high tumor grades, large tumor volumes, and advanced stage are proven indicators of poor prognosis, Hpr-expression is potentially of prognostic significance in prostate cancer.

Example 19B

Expression of OA-519 by Prostatic Adenocarcinoma

OA-519 expression in prostate cancer was also found to be associated with disease recurrence. Patients having been diagnosed and treated for prostate adenocarcinoma were selected from the fries of the Mountain Home VA Medical Center. The study population included 99 patients with prostate cancer in American Urologic System (AUS) stages A through D1. Clinical Stage information was obtained from the tumor registry abstracts or by review of the clinical records. Patients were excluded from the study is they had distant metastasis at the time of presentation (AUS stage D2), their status at last follow up was unknown, or if the total follow up was less than two years.

Immunohistochemical Studies

A single representative tissue block was selected from each cancer for immunohistochemical staining. An affinity purified polyclonal antibody raised in rabbits against purified OA-519 was used in this study. Staining was performed on routinely processed, formalin fixed, paraffin embedded tissue. The Avidin-Biotin Complex (ABC) immunoperoxidase technique utilizing unlabeled primary antibody was used. In brief, 6mm deparaffinized and rehydrated tissue sections were incubated in 5% nonfat dry milk in phosphate buffered saline (PBS) including 3% hydrogen peroxide for 20 minutes to block endogenous peroxidase activity as well as non-specific protein interactions. Slides were then incubated with affinity-purified polyclonal anti-OA-519 at 2.7 ug/ml in PBS at pH 7.2 for one hour at room temperature. With intervening washes with PBS, the sections were successively incubated with biotinylated goat anti-rabbit immunoglobulin diluted 1:200 in PBS (Vector Laboratories) and avidin-horseradish peroxidase complex (Vectastain®, Vector Laboratories), both for 30 minutes at 22° C. Aminoethylcarbazole (AEC) (Vector Laboratories) was used as the chromogen with Mayer's hematoxylin counterstain. For negative controls, PBS was substituted for primary antibody for each case. A known anti-OA-519 positive case was used as a positive control with every run.

Staining was defined as positive for OA-519 epitopes if (1) immunoreactivity was discernible at lower power (100x) (2) granular cytoplasmic staining was present without observable nuclear staining, and (3) staining was heterogeneous (i.e., the level of reactivity varied from cell to cell or from region to region. Tumors were scored as positive or negative. Positive staining for OA-519 was seen in 56 (57%) of the 99 primary prostate cancers examined.

The mean total follow up time was 4.17 years (range, 2.01–9.33). Prostate cancer recurred or progressed in 19 (19%) of the patients. Progression was defined as the appearance of local or metastatic disease after "curative" treatment, such as radical prostatectomy or radiation, or advance in the stage of disease in patients treated with hormonal therapy or expectantly managed. The average time to progression of disease was 2.54 years (range 0.67–5.85).

Figure 20:
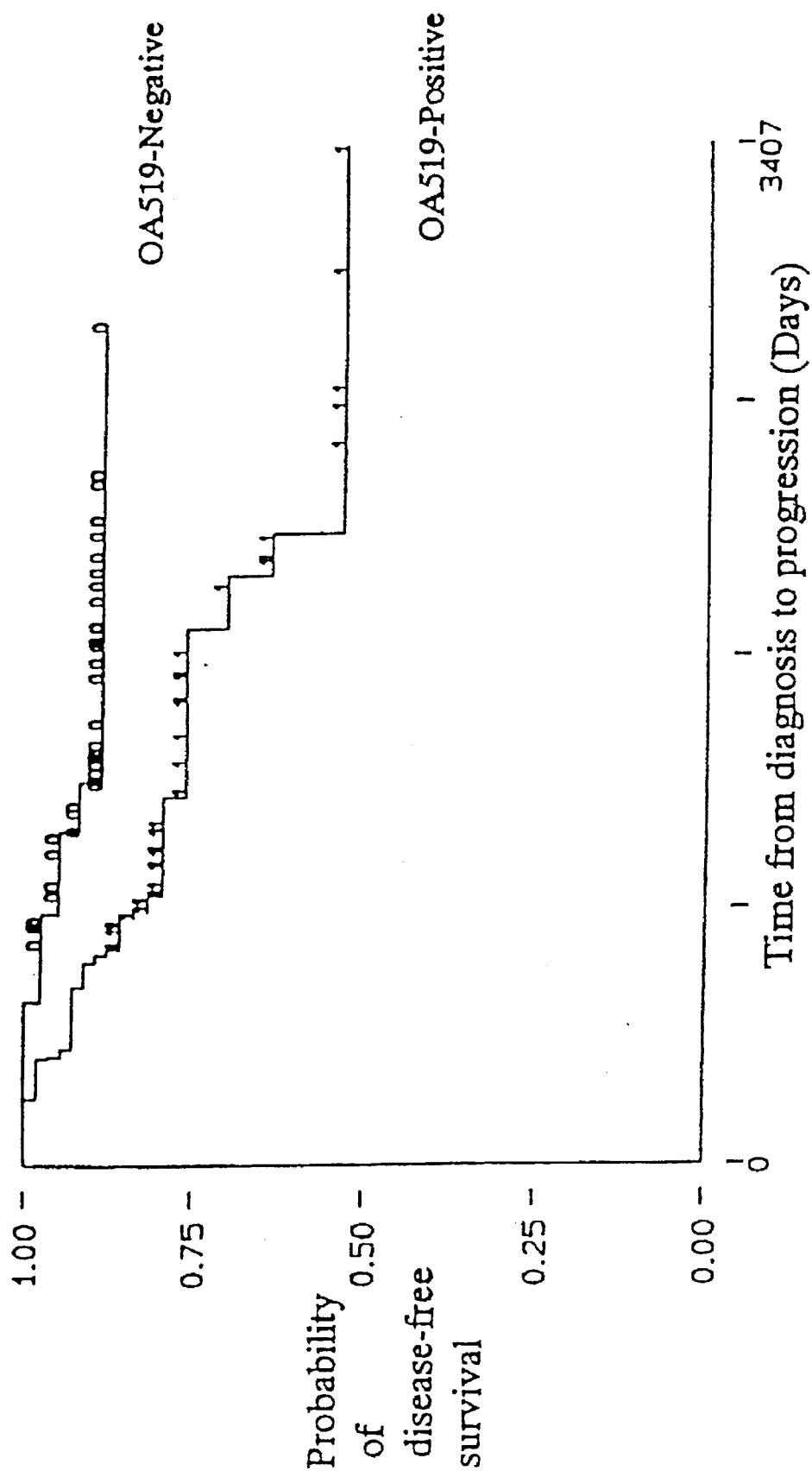
FIG. 20 shows the correlation between OA-519 expression and disease free survival in prostate cancer.

There were four (9%) cases of disease progression among the OA-519-negative group compared to 15 (27%) in the OA-519-positive group (Kaplan-Meier plot shown in FIG. 20). The difference between these groups in the proportion of cancers that progressed was statistically significant (Wilcoxon and log rank tests (P<0.009) and Fisher exact test (P<0.04)). OA-519 was a particularly valuable prognostic indicator among the low and intermediate grade prostate cancers, where the histologic grade by Gleason score was not a significant prognostic indicator (data not shown).

Example 20

Tissue Stains of Various Carcinomas

The following carcinomas have been tested for immunoreactivity using the polyclonal affinity purified anti-Hpr antibody:

breast
colon
lung (non-small cell)
prostate
ovary
endometrium
stomach
pancreas
esophagus (squamous carcinoma)
larynx (squamous carcinoma)
renal cell carcinoma (kidney)

All of these tumors show cytoplasmic reactivity with anti-Hpr antibody. Colon, lung, prostate, ovary, stomach, and kidney have all shown differential staining (some tumors have positive staining and samples from other tumors are negative).

Ovarian Carcinoma

An ovarian carcinoma study by Kacinski et al. is in progress using the same antibody, staining procedure, and interpretation that was used in the above breast carcinoma study. However, based on analysis of 34 patients completed so far, there is an association of OA-519 expression with reduced disease-free and overall survival, which is demonstrated in FIG. 21.

Example 21

Serum Assay for OA-519

OA-519 can also be detected in the serum of a patient having a tumor which expresses the antigen. A serum sample is obtained from a patient suspected of having a metastatic tumor and clarified by centrifugation. A high molecular weight fraction of the serum sample is electrophoresed on a 4% Lammeli gel and analyzed by Western blotting using purified polyclonal anti-OA-519 antibody according to Example 13. The blot is developed with $^{125}$I-protein A. A band at the level of 270 kDa in the Western blot indicates the presence of OA-519.

Example 22

Enzyme Linked Immunosorbent Assay (ELISA) To Circulating OA519™

Monoclonal antibodies reactive with OA519® were produced by immunizing female Balb/C mice with purified OA519, isolating antibody producing B-cells from the spleen and fusing them to F/0 mouse myeloma cells using polyethylene glycol. Hybridomas which produced antibodies reactive with OA519 were selected using a plastic microtiter plate which had OA519 adsorbed to it. Selected hybridomas were cloned by limiting dilution and subcloned three times by limiting dilution to ensure monoclonality. Monoclonal antibodies which were able to react with OA519-in blood were selected for use in the ELISA assay. Their specificity was confirmed by evaluation of purified OA519 on Wester blots and by detection of circulating OA519 in blood samples containing elevated OA519 by Western blots.

Polyclonal anti-OA519® antibodies were generated in rabbits by immunizing them with purified OA519 in Freunds complete adjuvant followed by booster injections in Freunds incomplete adjuvant. After test bleeds showed a response, assessed by antibody binding to OA519 adsorbed to plastic microtiter plates, a volume of blood was removed. The antibodies were separated by ion exchange chromatography or affinity chromatography and conjugated with biotin for use as the secondary antibody in the ELISA format.

The assay of soluble OA519® was performed as follows: Calibrators containing known amounts of OA519 or unknown specimens were added to microtiter plate wells which have been coated with monoclonal anti-OA519 antibodies and incubated for two hours at room temperature (15°–30° C.). The calibrator or specimen was removed and the wells were washed with a phosphate buffered saline-Tween solution. The antibody bound the OA519 present in the calibrators and specimens and retained it in the microtiter plate well. The secondary anti-OA519 (rabbit) antibody which has been biotinylated was then added to the washed wells. If OA519 was present, the secondary antibody reacted with the bound antigen and formed a "sandwich". After a two-hour, room temperature incubation, the unreacted secondary antibody was washed away as above.

To detect the presence of the biotinylated antibody, streptavidin conjugated with horseradish peroxidase (HRP) was added which binds to the biotin. After 1 hour room temperature incubation, the unreacted streptavidin-HRP was washed away. To detect the HRP bound to the rabbit anti-OA519, substrate (hydrogen peroxide and ortho-phenylene diamine) was added and allowed to react for 30 minutes at room temperature. Sulfuric acid was added to stop the enzyme reaction and fully develop the color. The intensity of the color was measured in an appropriate spectrophotometer at a wavelength of 490 nm. The intensity was directly proportional to the quantity of OA519 in the calibrator or unknown. The unknowns were quantitated by interpolation from the calibrator curve and correcting for any dilution factor used.

Calibrator curves generated by four different individuals fit a 3rd order polynomial equation, although point-to-point or other data reduction equations could be used. When each calibrator and unknown was assayed in duplicate and the absorbances averaged to generate the calibrator curve, the % C.V.'s (standard deviation divided by the mean times 100) were typically less than 10% (intra-assay). The day-to-day and person-to-person reproducibility (inter-assay) was assessed by quantitating a specimen containing OA519. This was assayed by five people on different days. The overall mean dose was 10.2 ng OA519/ml, the standard deviation was 1.2 ng OA519/ml which results in an interassay % C.V. of 12.1%

To confirm the specificity of the assay and verify the dose-response relationship, normal human serum and matched EDTA plasma samples were spiked with purified OA519. These were then serially diluted in the unspiked calibrator buffer and assayed. The dose response was linear for both serum and EDTA plasma, again supporting the specificity of the assay system.

Example 23

Diagnostic Use of ELISA assay for Circulating OA-519

ELISA determination of circulating OA-519 was performed for a number of individuals and correlated with the state of neoplastic disease in these individuals. Plasma specimens were obtained from individuals that were: normal (n=48); with benign breast disease (n=20); with diagnosed but treated breast cancer (no evidence of disease (NED) (n=45); with active breast cancer (n=57); with treated colon cancer (NED) (n=8); with active colon cancer (N=14); with active lung cancer (N=10); with active ovarian cancer (n=6); and with active prostate cancer (N=13). The mean OA519 values, determined as described in Example 22, are shown in FIGS. 22 and 23 for each of these categories, along with the standard error and range of values.

Figure 22:
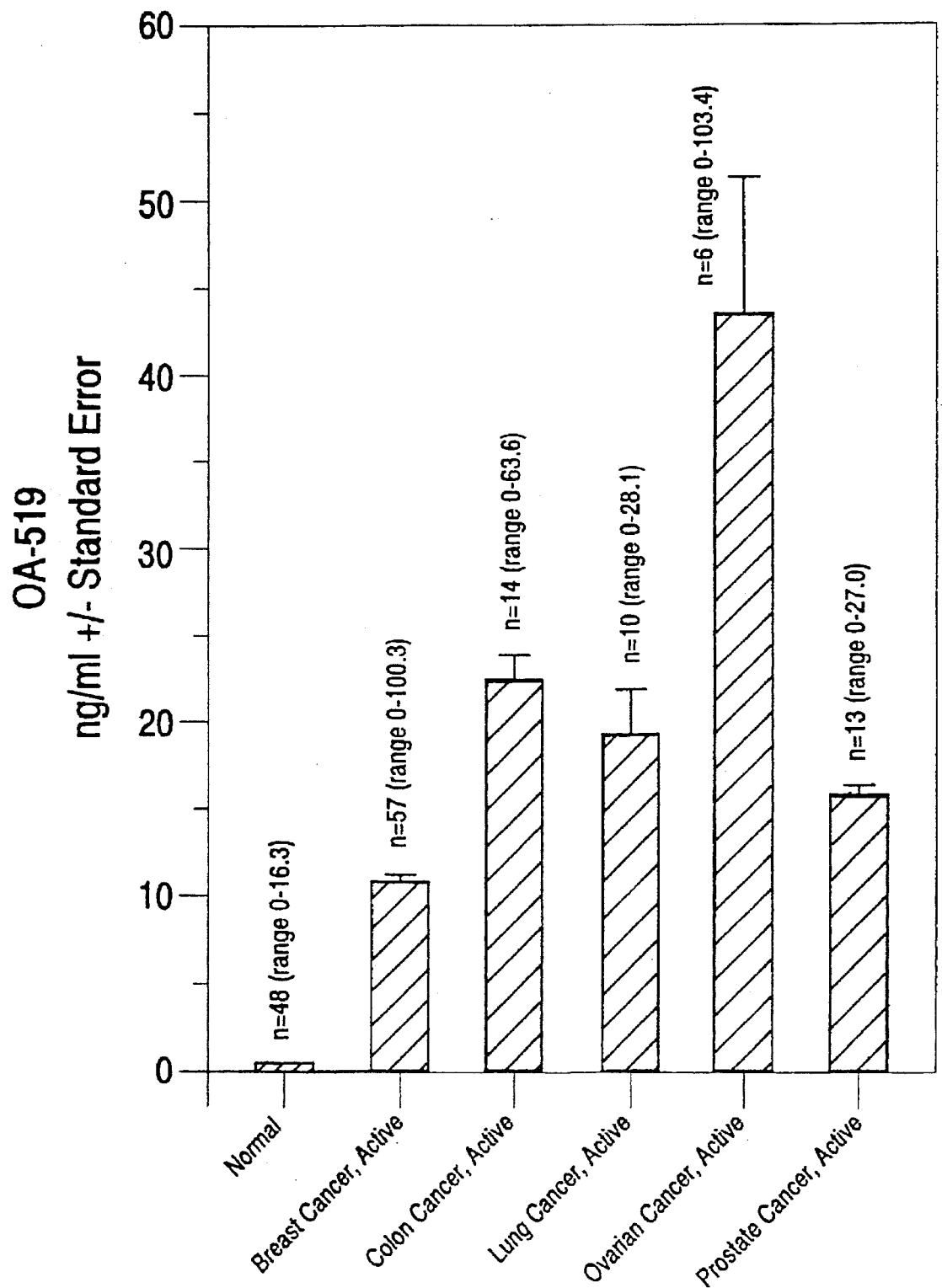
FIG. 22 shows the amount of OA-519 detected in the blood of patients diagnosed with different types of cancer.
Figure 23:
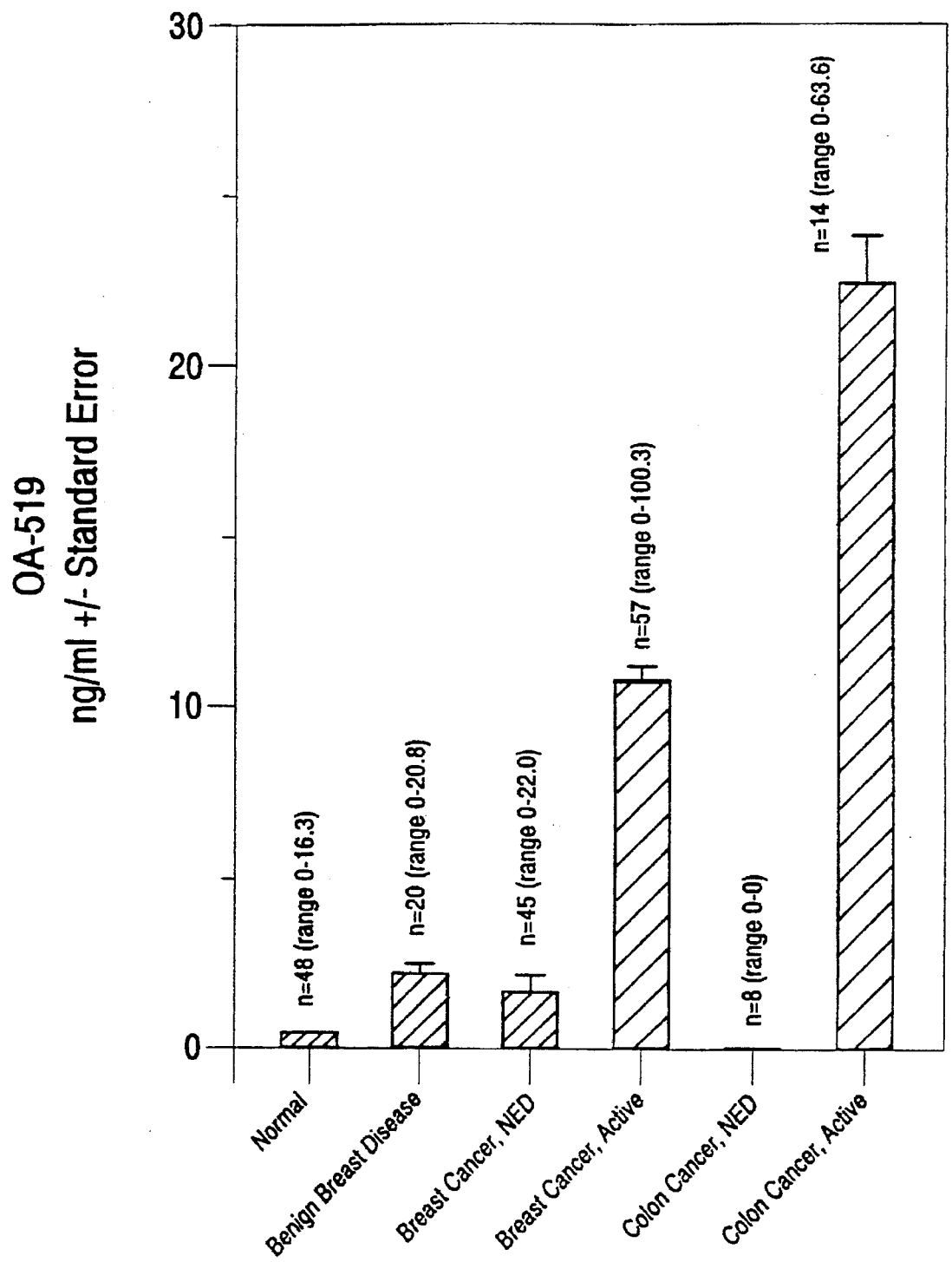
FIG. 23 shows the amount of OA-519 detected in the blood of cancer patients with active or inactive disease.

FIG. 22 summarizes the ELISA results for plasma samples from patients with breast, colon, lung, ovarian or prostate cancer, and compares the mean OA-519 level for these cancer patients to the mean OA-519 level in normal individuals. As shown in FIG. 22, OA-519 is elevated in the plasma of these cancer patients, compared to normal control individuals. In FIG. 23, the plasma level of OA-519 in patients with active cancer is compared to that of in individuals with no evidence of active disease. For both diseases tested (breast cancer and colon cancer) these data clearly shown that these cancer patients contain higher levels of OA519® in their blood than the normal or benign breast diseased individuals.

Example 24

Figure 24:
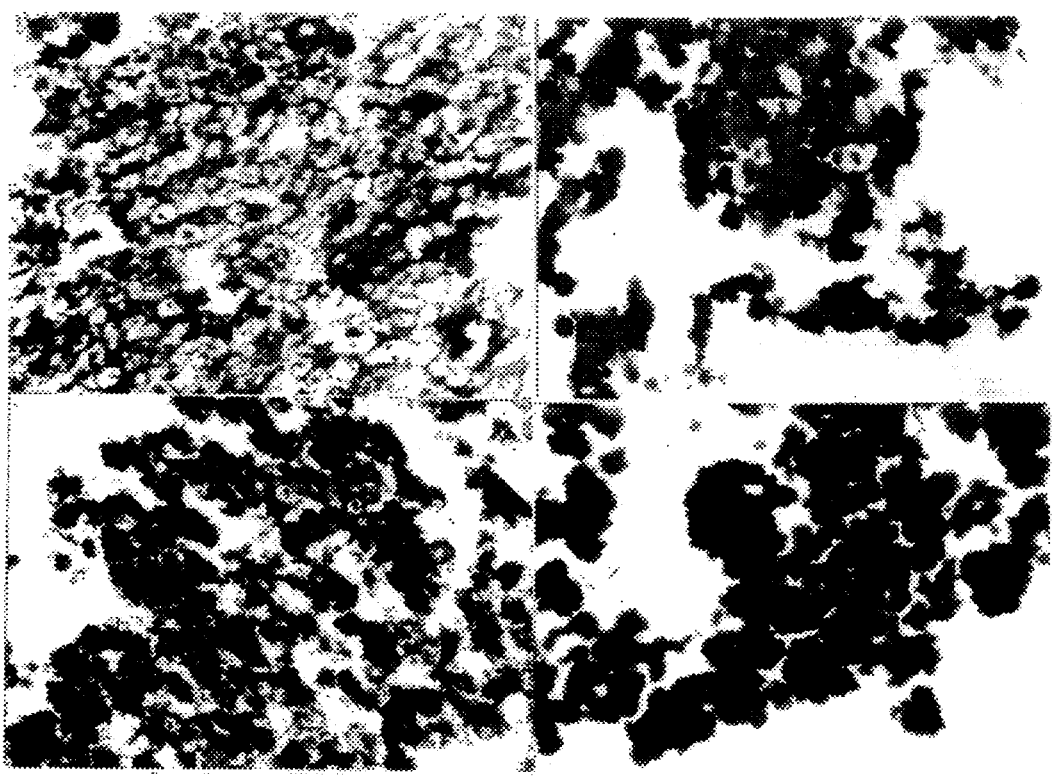
FIG. 24 shows detection of OA-519$_{FAS}$ expression in tumor cell lines by situ hybridization of riboprobes having FAS sequence.

OA-519 expression analyzed by in situ hybridization cDNA from a ZR-75-1 library yielded a 1.6 kb probe, pFAS 1.6, showing ~85% nucleotide identity with 3' sequences of rat fatty acid synthase cDNA. On Northern blots of total ZR-75-1 RNA, this probe hybridized with a single ~9.5 kb message (data not shown). In situ hybridization for OA-519 in formalin-fixed paraffin-embedded ZR-75-1 and DU-4475 human Breast cells using digoxigenin-labeled riboprobes derived from pFAS 1.6 in Bluescript II is shown in FIG. 24. The left panel is anti-sense, while the right panel is the sense control. Anti-sense riboprobes generated from pFAS 1.6 yielded a substantially stronger hybridization signal with ZR-75-1 cells than with DU-4475 cells (FIG. 24), showing that message levels and protein levels were concordant. Thus, cells that express OA-519 can be detected by either immunohistochemistry or in situ hybridization.

These data together suggest that OA-519 over-expression is from increased message levels, due either to increased transcriptional activation or to prolonged message stability. Increased OA-519 levels were not likely due to prolongation of OA-519 protein half-life since OA-519 protein over-expression was accompanied by OA-519 message over-expression. Similarly, experiments finding equivalent pFAS 1.6 hybridization signals among Southern blots of cell lines differing widely in OA-519 expression indicated that over-expression was not likely from gene amplification.

It will be understood that while the invention has been described in conjunction with specific embodiments thereof, the foregoing description and examples are intended to illustrate, but not limit the scope of the invention. Other aspects, advantages and modifications will be apparent to those skilled in the art to which the invention pertains, and these aspects and modifications are within the scope of the invention, which is limited only by the appended claims.

We claim:

1. A nucleic acid molecule produced by recombinant methods, containing a nucleotide sequence comprising inserts from clones pFAS 1.6, pFAS3.0, pFAS2.2 and pFAS4.6 deposited under ATCC accession Nos. 75643, 75645, 75644 and 75646, respectively, assembled in accordance with a Clone Map shown in FIG. 12D.

2. A nucleic acid molecule produced by recombinant methods, wherein said nucleic acid molecule encodes the amino acid sequence of SEQ ID NO:10.

3. An isolated nucleic acid probe comprising at least 20 contiguous nucleotides selected from or complementary to one strand of a double stranded nucleic acid molecule according to SEQ ID NO:9.

4. The nucleic acid molecule according to claim 2, wherein said nucleic acid molecule is an expression vector which expresses said amino acid sequence.

5. A recombinant cell containing the nucleic acid molecule of claim 4.

6. An isolated nucleic acid probe which specifically hybridizes to a single band which comprises a nucleic acid molecule comprising SEQ ID NO:9 but not to other mRNA molecules from ZR-75-1 breast cancer cells on Northern blots.

7. A pair of nucleic acid primers comprising at least 10 contiguous nucleotides selected from or complementary to a sequence of SEQ ID NO:9, wherein nucleic acid amplification using the pair of nucleic acid primers will produce an amplified nucleic acid comprising at least a portion of the sequence of SEQ ID NO:9.

8. The nucleic acid molecule according to claim 1, wherein the nucleic acid molecule is an expression vector which expresses the nucleic acid sequence.

9. A recombinant cell containing the nucleic acid molecule of claim 8.

10. The pair of nucleic acid primers of claim 7 where the primers are at least 14 contiguous nucleotides selected from or complementary to SEQ ID NO:9.

\* \* \* \* \*